(12) United States Patent
Skelton et al.

(10) Patent No.: US 9,050,471 B2
(45) Date of Patent: Jun. 9, 2015

(54) POSTURE STATE DISPLAY ON MEDICAL DEVICE USER INTERFACE

(75) Inventors: Dennis M. Skelton, Bloomington, MN (US); Jon P. Davis, St. Michael, MN (US); Rajeev Sahasrabudhe, Maple Grove, MN (US); Shyam Gokaldas, New Brighton, MN (US); Joseph J. Nolan, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 938 days.

(21) Appl. No.: 12/433,103

(22) Filed: Apr. 30, 2009

(65) Prior Publication Data

US 2010/0010584 A1    Jan. 14, 2010

Related U.S. Application Data

(60) Provisional application No. 61/080,008, filed on Jul. 11, 2008.

(51) Int. Cl.
*A61N 1/37* (2006.01)
*A61N 1/36* (2006.01)
(Continued)

(52) U.S. Cl.
CPC ............... *A61N 1/36132* (2013.01); *A61B 5/11* (2013.01); *A61B 5/6846* (2013.01);
(Continued)

(58) Field of Classification Search
CPC .............. A61N 1/362; A61N 1/36535; A61N 1/37235; A61N 1/37258
USPC ........ 607/3, 6, 42, 43, 48–50, 144, 19, 60, 62
See application file for complete search history.

(56) References Cited

U.S. PATENT DOCUMENTS

| 4,297,685 A | 10/1981 | Brainard, II |
| 4,365,633 A | 12/1982 | Loughman |

(Continued)

FOREIGN PATENT DOCUMENTS

| DE | 19831109 | 1/2000 |
| DE | 10024103 | 11/2001 |

(Continued)

OTHER PUBLICATIONS

"Analysis of heart rate dynamics by methods derived from non-linear mathematics: Clinical applicability and prognostic significance," http://herkules.oulu.fi.isbn9514250133/html, 4 pp., 2004.

(Continued)

*Primary Examiner* — Christopher D Koharski
*Assistant Examiner* — Michael Carey
(74) *Attorney, Agent, or Firm* — Shumaker & Sieffert, P.A.

(57) ABSTRACT

The disclosure provides a system that displays a posture state indication to a user. A posture state indication represents the current posture state of the patient, which may be a combination of patient posture and activity. As a patient changes posture and activity throughout a daily routine, a posture state detector may generate a posture state value that may be used to categorize the patient's posture or posture and activity level as one of multiple posture states used to adjust therapy. The posture state may be associated with one of multiple posture state indications that may be presented to the patient. The posture state indication shows the patient the posture state currently detected by the posture state detector. The posture state indication may help the patient to effectively monitor therapy changes due to automatic, semi-automatic or patient-directed therapy adjustments made as a function of posture state.

40 Claims, 26 Drawing Sheets

(51) Int. Cl.
*A61B 5/00* (2006.01)
*A61N 1/372* (2006.01)
*G06F 19/00* (2011.01)
*A61B 5/11* (2006.01)
*A61N 1/365* (2006.01)

(52) U.S. Cl.
CPC ...... *A61B 5/7445* (2013.01); *A61B 2562/0219* (2013.01); *A61N 1/36071* (2013.01); *A61N 1/36535* (2013.01); *A61N 1/37247* (2013.01); *G06F 19/3406* (2013.01); *G06F 19/3418* (2013.01); *G06F 19/345* (2013.01); *A61N 1/36135* (2013.01)

(56) References Cited

U.S. PATENT DOCUMENTS

| | | |
|---|---|---|
| 4,543,955 A | 10/1985 | Schroeppel |
| 4,550,736 A | 11/1985 | Broughton et al. |
| 4,566,456 A | 1/1986 | Koning et al. |
| 4,771,780 A | 9/1988 | Sholder |
| 4,776,345 A | 10/1988 | Cohen et al. |
| 4,846,180 A | 7/1989 | Buffet |
| 4,846,195 A | 7/1989 | Alt |
| 5,031,618 A | 7/1991 | Mullett |
| 5,040,534 A | 8/1991 | Mann et al. |
| 5,040,536 A | 8/1991 | Riff |
| 5,058,584 A | 10/1991 | Bourgeois |
| 5,125,412 A | 6/1992 | Thornton |
| 5,154,180 A | 10/1992 | Blanchet et al. |
| 5,158,078 A | 10/1992 | Bennett et al. |
| 5,167,229 A | 12/1992 | Peckham et al. |
| 5,233,984 A | 8/1993 | Thompson |
| 5,275,159 A | 1/1994 | Griebel |
| 5,312,446 A | 5/1994 | Holschbach et al. |
| 5,335,657 A | 8/1994 | Terry, Jr. et al. |
| 5,337,758 A | 8/1994 | Moore et al. |
| 5,342,409 A | 8/1994 | Mullett |
| 5,354,317 A | 10/1994 | Alt |
| 5,425,750 A | 6/1995 | Moberg |
| 5,469,861 A | 11/1995 | Piscopo et al. |
| 5,476,483 A | 12/1995 | Bornzin et al. |
| 5,487,755 A | 1/1996 | Snell et al. |
| 5,513,645 A | 5/1996 | Jacobson et al. |
| 5,514,162 A | 5/1996 | Bornzin et al. |
| 5,558,640 A | 9/1996 | Pfeiler et al. |
| 5,562,707 A | 10/1996 | Prochazka et al. |
| 5,593,431 A | 1/1997 | Sheldon |
| 5,622,428 A | 4/1997 | Bonnet |
| 5,628,317 A | 5/1997 | Starkebaum et al. |
| 5,643,332 A | 7/1997 | Stein |
| 5,645,053 A | 7/1997 | Remmers et al. |
| 5,674,258 A | 10/1997 | Henschel et al. |
| 5,711,316 A | 1/1998 | Elsberry et al. |
| 5,720,770 A | 2/1998 | Nappholz et al. |
| 5,732,696 A | 3/1998 | Rapoport et al. |
| 5,741,310 A | 4/1998 | Wittkampf |
| 5,782,884 A | 7/1998 | Stotts et al. |
| 5,814,093 A | 9/1998 | Stein |
| 5,832,932 A | 11/1998 | Elsberry et al. |
| 5,833,709 A | 11/1998 | Rise et al. |
| 5,836,989 A | 11/1998 | Shelton |
| 5,851,193 A | 12/1998 | Arikka et al. |
| 5,865,760 A | 2/1999 | Lidman et al. |
| 5,885,471 A | 3/1999 | Ruben et al. |
| 5,893,883 A | 4/1999 | Torgerson et al. |
| 5,895,371 A | 4/1999 | Levitas et al. |
| 5,904,708 A | 5/1999 | Goedeke |
| 5,911,738 A | 6/1999 | Sikorski et al. |
| 5,913,727 A | 6/1999 | Ahdoot |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,957,957 A | 9/1999 | Sheldon |
| 5,984,368 A | 11/1999 | Cain |
| 6,027,456 A | 2/2000 | Feler et al. |
| 6,038,475 A | 3/2000 | Sikorski et al. |
| 6,044,297 A | 3/2000 | Sheldon et al. |
| 6,045,513 A | 4/2000 | Stone et al. |
| 6,059,576 A | 5/2000 | Brann |
| 6,095,991 A | 8/2000 | Krausman et al. |
| 6,099,479 A | 8/2000 | Christopherson et al. |
| 6,102,874 A | 8/2000 | Stone et al. |
| 6,120,467 A | 9/2000 | Schallhorn |
| 6,128,534 A | 10/2000 | Park et al. |
| 6,134,459 A | 10/2000 | Roberts et al. |
| 6,152,890 A | 11/2000 | Kupfer et al. |
| 6,157,857 A | 12/2000 | Dimpfel |
| 6,165,143 A | 12/2000 | Van Lummel |
| 6,216,537 B1 | 4/2001 | Henschel et al. |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,308,099 B1 | 10/2001 | Fox et al. |
| 6,315,740 B1 | 11/2001 | Singh |
| 6,327,501 B1 | 12/2001 | Levine et al. |
| 6,341,236 B1 | 1/2002 | Osorio et al. |
| 6,351,672 B1 | 2/2002 | Park et al. |
| 6,368,284 B1 | 4/2002 | Bardy |
| 6,381,496 B1 | 4/2002 | Meadows et al. |
| 6,393,325 B1 | 5/2002 | Mann et al. |
| 6,438,408 B1 | 8/2002 | Mulligan et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,507,757 B1 | 1/2003 | Swain et al. |
| 6,514,218 B2 | 2/2003 | Yamamoto |
| 6,516,749 B1 | 2/2003 | Salasidis |
| 6,539,249 B1 | 3/2003 | Kadhiresan et al. |
| 6,547,755 B1 | 4/2003 | Lippe et al. |
| 6,572,557 B2 | 6/2003 | Tchou et al. |
| 6,574,507 B1 | 6/2003 | Bonnet |
| 6,605,038 B1 | 8/2003 | Teller et al. |
| 6,609,031 B1 | 8/2003 | Law et al. |
| 6,611,783 B2 | 8/2003 | Kelly, Jr. et al. |
| 6,620,151 B2 | 9/2003 | Blischak et al. |
| 6,625,493 B2 | 9/2003 | Kroll et al. |
| 6,635,048 B1 | 10/2003 | Ullestad et al. |
| 6,641,542 B2 | 11/2003 | Cho et al. |
| 6,658,292 B2 | 12/2003 | Kroll et al. |
| 6,659,968 B1 | 12/2003 | McClure |
| 6,662,047 B2 | 12/2003 | Sorensen |
| 6,665,558 B2 | 12/2003 | Kalgren et al. |
| 6,668,188 B2 | 12/2003 | Sun et al. |
| 6,687,538 B1 | 2/2004 | Hrdlicka et al. |
| 6,731,984 B2 | 5/2004 | Cho et al. |
| 6,740,075 B2 | 5/2004 | Lebel et al. |
| 6,748,276 B1 | 6/2004 | Daignault, Jr. et al. |
| 6,752,766 B2 | 6/2004 | Kowallik et al. |
| 6,773,404 B2 | 8/2004 | Poezevera et al. |
| 6,782,315 B2 | 8/2004 | Lu et al. |
| 6,817,979 B2 | 11/2004 | Nihtilä |
| 6,820,025 B2 | 11/2004 | Bachmann et al. |
| 6,829,507 B1 | 12/2004 | Lidman et al. |
| 6,832,113 B2 | 12/2004 | Belalcazar |
| 6,834,436 B2 | 12/2004 | Townsend |
| 6,853,863 B2 | 2/2005 | Carter et al. |
| 6,878,121 B2 | 4/2005 | Krausman et al. |
| 6,884,596 B2 | 4/2005 | Civelli et al. |
| 6,890,306 B2 | 5/2005 | Poezevera |
| 6,895,341 B2 | 5/2005 | Barrey et al. |
| 6,922,587 B2 | 7/2005 | Weinberg |
| 6,923,784 B2 | 8/2005 | Stein |
| 6,928,324 B2 | 8/2005 | Park et al. |
| 6,937,899 B2 | 8/2005 | Sheldon et al. |
| 6,937,900 B1 | 8/2005 | Pianca et al. |
| 6,945,934 B2 | 9/2005 | Bardy |
| 6,964,641 B2 | 11/2005 | Cho et al. |
| 6,975,904 B1 | 12/2005 | Sloman |
| 6,997,882 B1 | 2/2006 | Parker et al. |

(56) References Cited

U.S. PATENT DOCUMENTS

| | | |
|---|---|---|
| 6,999,817 B2 | 2/2006 | Park et al. |
| 7,016,730 B2 | 3/2006 | Ternes |
| 7,031,772 B2 | 4/2006 | Condie |
| 7,043,305 B2 | 5/2006 | KenKnight et al. |
| 7,054,687 B1 | 5/2006 | Andersen |
| 7,066,910 B2 | 6/2006 | Bauhahn et al. |
| 7,082,333 B1 | 7/2006 | Bauhahn |
| 7,092,759 B2 | 8/2006 | Nehls et al. |
| 7,095,424 B2 | 8/2006 | Satoh et al. |
| 7,110,820 B2 | 9/2006 | Tcheng et al. |
| 7,117,036 B2 | 10/2006 | Florio |
| 7,123,967 B2 | 10/2006 | Weinberg |
| 7,130,681 B2 | 10/2006 | Gebhardt et al. |
| 7,130,689 B1 | 10/2006 | Turcott |
| 7,141,026 B2 | 11/2006 | Aminian et al. |
| 7,142,921 B2 | 11/2006 | Mattes et al. |
| 7,149,579 B1 | 12/2006 | Koh et al. |
| 7,149,584 B1 | 12/2006 | Koh et al. |
| 7,151,961 B1 | 12/2006 | Whitehurst et al. |
| 7,155,279 B2 | 12/2006 | Whitehurst et al. |
| 7,160,252 B2 | 1/2007 | Cho et al. |
| 7,162,304 B1 | 1/2007 | Bradley |
| 7,167,743 B2 | 1/2007 | Heruth et al. |
| 7,167,751 B1 | 1/2007 | Whitehurst et al. |
| 7,181,281 B1 | 2/2007 | Kroll |
| 7,189,204 B2 | 3/2007 | Ni et al. |
| 7,207,947 B2 | 4/2007 | Koh et al. |
| 7,210,240 B2 | 5/2007 | Townsend et al. |
| 7,212,862 B2 | 5/2007 | Park et al |
| 7,214,197 B2 | 5/2007 | Prass |
| 7,218,964 B2 | 5/2007 | Hill et al. |
| 7,218,968 B2 | 5/2007 | Condie et al. |
| 7,221,979 B2 | 5/2007 | Zhou et al. |
| 7,231,254 B2 | 6/2007 | DiLorenzo |
| 7,242,983 B2 | 7/2007 | Frei et al. |
| 7,252,640 B2 | 8/2007 | Ni et al. |
| 7,266,412 B2 | 9/2007 | Stypulkowski |
| 7,308,311 B2 | 12/2007 | Sorensen et al. |
| 7,313,440 B2 | 12/2007 | Miesel |
| 7,317,948 B1 | 1/2008 | King et al. |
| 7,330,760 B2 | 2/2008 | Heruth et al. |
| 7,366,569 B2 | 4/2008 | Belalcazar |
| 7,366,572 B2 | 4/2008 | Heruth et al. |
| 7,387,610 B2 | 6/2008 | Stahmann |
| 7,389,147 B2 | 6/2008 | Wahlstrand et al. |
| 7,395,113 B2 | 7/2008 | Heruth |
| 7,403,820 B2 | 7/2008 | DiLorenzo |
| 7,406,351 B2 | 7/2008 | Wesselink |
| 7,415,308 B2 | 8/2008 | Gerber et al. |
| 7,447,545 B2 | 11/2008 | Heruth et al. |
| 7,471,290 B2 | 12/2008 | Wang et al. |
| 7,471,980 B2 | 12/2008 | Koshiol |
| 7,489,970 B2 | 2/2009 | Lee et al. |
| 7,491,181 B2 | 2/2009 | Heruth et al. |
| 7,505,815 B2 | 3/2009 | Lee et al. |
| 7,519,431 B2 | 4/2009 | Goetz et al. |
| 7,542,803 B2 | 6/2009 | Heruth et al. |
| 7,548,786 B2 | 6/2009 | Lee et al. |
| 7,559,901 B2 | 7/2009 | Maile |
| 7,572,225 B2 | 8/2009 | Stahmann |
| 7,577,479 B2 | 8/2009 | Hartley et al. |
| 7,580,752 B2 | 8/2009 | Gerber et al. |
| 7,584,808 B2 | 9/2009 | Dolgin et al. |
| 7,590,453 B2 | 9/2009 | Heruth |
| 7,590,455 B2 | 9/2009 | Heruth et al. |
| 7,590,481 B2 | 9/2009 | Lu et al. |
| 7,591,265 B2 | 9/2009 | Lee et al. |
| 7,603,170 B2 | 10/2009 | Hatlestad et al. |
| 7,623,919 B2 | 11/2009 | Goetz et al. |
| 7,634,379 B2 | 12/2009 | Noble |
| 7,664,546 B2 | 2/2010 | Hartley et al. |
| 7,672,806 B2 | 3/2010 | Tronconi |
| 7,717,848 B2 | 5/2010 | Heruth et al. |
| 7,769,464 B2 | 8/2010 | Gerber et al. |
| 7,792,583 B2 | 9/2010 | Heruth et al. |
| 2002/0038137 A1 | 3/2002 | Stein |
| 2002/0091308 A1 | 7/2002 | Kipshidze et al. |
| 2002/0107553 A1 | 8/2002 | Hill et al. |
| 2002/0115939 A1 | 8/2002 | Mulligan et al. |
| 2002/0151824 A1 | 10/2002 | Fischer |
| 2002/0165586 A1 | 11/2002 | Hill et al. |
| 2002/0169485 A1 | 11/2002 | Pless et al. |
| 2002/0170193 A1 | 11/2002 | Townsend et al. |
| 2003/0004423 A1 | 1/2003 | Lavie et al. |
| 2003/0036783 A1 | 2/2003 | Bauhahn et al. |
| 2003/0045910 A1 | 3/2003 | Sorensen et al. |
| 2003/0065370 A1 | 4/2003 | Lebel et al. |
| 2003/0088185 A1 | 5/2003 | Prass |
| 2003/0149457 A1 | 8/2003 | Tcheng et al. |
| 2003/0171791 A1 | 9/2003 | KenKnight et al. |
| 2003/0181960 A1 | 9/2003 | Carter et al. |
| 2003/0204211 A1 | 10/2003 | Condie et al. |
| 2004/0015103 A1 | 1/2004 | Aminian et al. |
| 2004/0049132 A1 | 3/2004 | Barron et al. |
| 2004/0088020 A1 | 5/2004 | Condie et al. |
| 2004/0102814 A1 | 5/2004 | Sorensen et al. |
| 2004/0133248 A1 | 7/2004 | Frei et al. |
| 2004/0138716 A1 | 7/2004 | Kon et al. |
| 2004/0147975 A1 | 7/2004 | Popovic et al. |
| 2004/0199215 A1 | 10/2004 | Lee et al. |
| 2004/0199216 A1 | 10/2004 | Lee et al. |
| 2004/0199217 A1 | 10/2004 | Lee et al. |
| 2004/0199218 A1 | 10/2004 | Lee et al. |
| 2004/0215286 A1 | 10/2004 | Stypulkowski |
| 2004/0220621 A1 | 11/2004 | Zhou et al. |
| 2004/0225332 A1 | 11/2004 | Gebhardt et al. |
| 2004/0257693 A1 | 12/2004 | Ehrlich |
| 2005/0042589 A1 | 2/2005 | Hatlestad et al. |
| 2005/0043767 A1 | 2/2005 | Belalcazar |
| 2005/0060001 A1 | 3/2005 | Singhal et al. |
| 2005/0061320 A1 | 3/2005 | Lee et al. |
| 2005/0107722 A1 | 5/2005 | Ozaki et al. |
| 2005/0113710 A1 | 5/2005 | Stahmann et al. |
| 2005/0113887 A1 | 5/2005 | Bauhahn |
| 2005/0126026 A1 | 6/2005 | Townsend et al. |
| 2005/0137627 A1 | 6/2005 | Koshiol et al. |
| 2005/0145246 A1* | 7/2005 | Hartley et al. ........... 128/203.14 |
| 2005/0172311 A1 | 8/2005 | Hjelt et al. |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222638 A1 | 10/2005 | Foley et al. |
| 2005/0228455 A1 | 10/2005 | Kramer et al. |
| 2005/0234514 A1 | 10/2005 | Heruth et al. |
| 2005/0234518 A1 | 10/2005 | Heruth et al. |
| 2005/0240242 A1 | 10/2005 | DiLorenzo |
| 2005/0245988 A1 | 11/2005 | Miesel |
| 2005/0283210 A1 | 12/2005 | Blischak et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0195051 A1 | 8/2006 | Schnapp et al. |
| 2006/0206167 A1 | 9/2006 | Flaherty et al. |
| 2006/0212080 A1 | 9/2006 | Hartley et al. |
| 2006/0213267 A1 | 9/2006 | Tronconi et al. |
| 2006/0235289 A1 | 10/2006 | Wesselink et al. |
| 2006/0235472 A1 | 10/2006 | Goetz et al. |
| 2006/0241513 A1 | 10/2006 | Hatlestad et al. |
| 2006/0247732 A1 | 11/2006 | Wesselink |
| 2006/0247739 A1 | 11/2006 | Wahlstrand et al. |
| 2006/0259099 A1 | 11/2006 | Goetz et al. |
| 2006/0262120 A1 | 11/2006 | Rosenberg |
| 2006/0265025 A1 | 11/2006 | Goetz et al. |
| 2006/0287686 A1 | 12/2006 | Cullen et al. |
| 2007/0015976 A1* | 1/2007 | Miesel et al. ................. 600/301 |
| 2007/0038265 A1 | 2/2007 | Tcheng et al. |

(56) References Cited

U.S. PATENT DOCUMENTS

| | | |
|---|---|---|
| 2007/0050715 A1 | 3/2007 | Behar |
| 2007/0073355 A1 | 3/2007 | DiLorenzo et al. |
| 2007/0115277 A1 | 5/2007 | Wang et al. |
| 2007/0118056 A1 | 5/2007 | Wang et al. |
| 2007/0123758 A1 | 5/2007 | Miesel et al. |
| 2007/0129622 A1 | 6/2007 | Bourget et al. |
| 2007/0129641 A1 | 6/2007 | Sweeney |
| 2007/0129769 A1 | 6/2007 | Bourget et al. |
| 2007/0129774 A1 | 6/2007 | Bourget et al. |
| 2007/0150026 A1 | 6/2007 | Bourget et al. |
| 2007/0150029 A1 | 6/2007 | Bourget et al. |
| 2007/0213789 A1 | 9/2007 | Nolan et al. |
| 2007/0249968 A1 | 10/2007 | Miesel et al. |
| 2007/0250121 A1 | 10/2007 | Miesel et al. |
| 2007/0250134 A1 | 10/2007 | Miesel et al. |
| 2007/0255118 A1 | 11/2007 | Miesel et al. |
| 2007/0255154 A1 | 11/2007 | Lu et al. |
| 2007/0265664 A1 | 11/2007 | Gerber et al. |
| 2007/0265681 A1 | 11/2007 | Gerber et al. |
| 2007/0276439 A1 | 11/2007 | Miesel et al. |
| 2007/0293737 A1 | 12/2007 | Heruth et al. |
| 2007/0293917 A1 | 12/2007 | Thompson |
| 2008/0071150 A1 | 3/2008 | Miesel et al. |
| 2008/0071324 A1 | 3/2008 | Miesel et al. |
| 2008/0071326 A1 | 3/2008 | Heruth et al. |
| 2008/0071327 A1 | 3/2008 | Miesel et al. |
| 2008/0079444 A1 | 4/2008 | Denison |
| 2008/0081958 A1 | 4/2008 | Denison et al. |
| 2008/0114219 A1 | 5/2008 | Zhang et al. |
| 2008/0164979 A1 | 7/2008 | Otto |
| 2008/0177355 A1 | 7/2008 | Miesel et al. |
| 2008/0188901 A1 | 8/2008 | Sanghera et al. |
| 2008/0188909 A1 | 8/2008 | Bradley |
| 2008/0194998 A1 | 8/2008 | Holmstrom et al. |
| 2008/0204255 A1 | 8/2008 | Flexer et al. |
| 2008/0269812 A1 | 10/2008 | Gerber et al. |
| 2008/0269843 A1 | 10/2008 | Gerber |
| 2008/0281376 A1 | 11/2008 | Gerber et al. |
| 2008/0281379 A1 | 11/2008 | Wesselink |
| 2008/0281381 A1 | 11/2008 | Gerber et al. |
| 2008/0288200 A1 | 11/2008 | Noble |
| 2008/0300449 A1 | 12/2008 | Gerber et al. |
| 2008/0300470 A1 | 12/2008 | Gerber et al. |
| 2009/0030263 A1 | 1/2009 | Heruth et al. |
| 2009/0036951 A1 | 2/2009 | Heruth et al. |
| 2009/0046056 A1 | 2/2009 | Rosenberg et al. |
| 2009/0076343 A1 | 3/2009 | James et al. |
| 2009/0082829 A1 | 3/2009 | Panken et al. |
| 2009/0099627 A1 | 4/2009 | Molnar et al. |
| 2009/0105785 A1 | 4/2009 | Wei et al. |
| 2009/0118599 A1 | 5/2009 | Heruth et al. |
| 2009/0137933 A1 | 5/2009 | Lieberman et al. |
| 2009/0228841 A1 | 9/2009 | Hildreth |
| 2009/0233770 A1 | 9/2009 | Vincent et al. |
| 2009/0259216 A1 | 10/2009 | Drew et al. |
| 2009/0264789 A1 | 10/2009 | Molnar et al. |
| 2009/0270747 A1 | 10/2009 | van Dam et al. |
| 2009/0306740 A1 | 12/2009 | Heruth et al. |
| 2010/0010380 A1 | 1/2010 | Panken et al. |
| 2010/0010381 A1 | 1/2010 | Skelton et al. |
| 2010/0010382 A1 | 1/2010 | Panken et al. |
| 2010/0010383 A1 | 1/2010 | Skelton et al. |
| 2010/0010384 A1 | 1/2010 | Panken et al. |
| 2010/0010385 A1 | 1/2010 | Skelton et al. |
| 2010/0010386 A1 | 1/2010 | Skelton et al. |
| 2010/0010387 A1 | 1/2010 | Skelton et al. |
| 2010/0010388 A1 | 1/2010 | Panken et al. |
| 2010/0010389 A1 | 1/2010 | Davis et al. |
| 2010/0010390 A1 | 1/2010 | Skelton et al. |
| 2010/0010391 A1 | 1/2010 | Skelton et al. |
| 2010/0010392 A1 | 1/2010 | Skelton et al. |
| 2010/0010432 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |
| 2010/0010574 A1 | 1/2010 | Skelton et al. |
| 2010/0010575 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010583 A1 | 1/2010 | Panken et al. |
| 2010/0010585 A1 | 1/2010 | Davis et al. |
| 2010/0010586 A1 | 1/2010 | Skelton et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0010590 A1 | 1/2010 | Skelton et al. |
| 2010/0030286 A1 | 2/2010 | Goetz et al. |
| 2010/0121415 A1 | 5/2010 | Skelton et al. |
| 2010/0174155 A1 | 7/2010 | Heruth et al. |

FOREIGN PATENT DOCUMENTS

| | | |
|---|---|---|
| EP | 0564803 | 10/1993 |
| EP | 0845240 | 6/1998 |
| EP | 0849715 | 6/1998 |
| EP | 1195139 | 4/2002 |
| EP | 1291036 | 3/2003 |
| EP | 1308182 | 5/2003 |
| EP | 1331022 A2 | 7/2003 |
| EP | 1391846 | 2/2004 |
| EP | 1437159 | 7/2004 |
| EP | 1731088 | 12/2006 |
| EP | 1870128 | 12/2007 |
| EP | 1938862 | 7/2008 |
| EP | 2110067 A1 | 10/2009 |
| GB | 2330912 | 5/1999 |
| GB | 2408342 | 5/2005 |
| GB | 2447647 | 9/2008 |
| WO | 94/05371 | 3/1994 |
| WO | 96/29007 | 9/1996 |
| WO | 97/04705 | 2/1997 |
| WO | 97/49455 | 12/1997 |
| WO | 98/00197 | 1/1998 |
| WO | 99/56820 | 11/1999 |
| WO | 01/37930 | 5/2001 |
| WO | 02/28282 | 4/2002 |
| WO | 02/41771 | 5/2002 |
| WO | 02/087433 | 11/2002 |
| WO | 02/096512 | 12/2002 |
| WO | 02/100267 | 12/2002 |
| WO | 03/051356 | 6/2003 |
| WO | 03/065891 | 8/2003 |
| WO | 2005/028029 | 3/2005 |
| WO | 2005/035050 | 4/2005 |
| WO | 2005/079487 | 9/2005 |
| WO | 2005/089646 | 9/2005 |
| WO | 2005/089647 | 9/2005 |
| WO | 2005/089860 | 9/2005 |
| WO | 2005/102499 | 11/2005 |
| WO | 2005/120348 | 12/2005 |
| WO | 2007/009088 | 1/2007 |
| WO | 2007/051196 | 5/2007 |
| WO | 2007/064682 | 6/2007 |
| WO | 2007/064936 | 6/2007 |
| WO | 2007127455 A2 | 11/2007 |
| WO | 2008/026970 | 3/2008 |

OTHER PUBLICATIONS

"Design Competition: Runners-Up for the Best Three Designs," EPN, vol. 26, No. 1, 1 pg., 2002.

IBM and Citizen Watch develop Linux-Based "WatchPad," http://wwwlinuxdevices.com/news/NS6580187845.html, 5 pp., 2006.

"MiniMitter® Physiological and Behavioral Monitoring for Humans and Animals," http://www.minimitter.com/Products/Actiwatch, 3 pp., 2006.

"Watch," Wikipedia, 6 pp., http://en.wikipedia.org/wiki/Watch, 2006.

Aminian et al., "Physical Activity Monitoring Based on Accelerometry: Validation and Comparison with Video Observa-

(56) References Cited

OTHER PUBLICATIONS tion," Medical & Biological Engineering and Computing, vol. 37, No. 2, pp. 304-308,1999.
Amzica, "Physiology of Sleep and Wakefulness as it Relates to the Physiology of Epilepsy," Journal of Clinical Neurophysiology, American Clinical Neurophysiology Society, 19(6)1, pp. 488-503, 2002.
Ang et al., "Physical model of a MEMS accelerometer for low-g motion tracking applications," 2004 IEEE International Conference on Robotics and Automation, vol. 2, pp. 1345-1351, 2004.
Buchser et al., "Improved Physical Activity in Patients Treated for Chronic Pain by Spinal Cord Stimulation," Neuromodulation, vol. 8, Issue 1, pp. 40-48, Mar. 2005.
Crago et al., "An Elbow Extension Neuroprosthesis for Individuals with Tetraplegia," IEEE Transactions on Rehabilitation Engineering, vol. 6, No. 1, pp. 1-6, Mar. 1998.
Dejnabadi et al., "Estimation and Visualization of Sagittal Kinematics of Lower Limbs Orientation Using Body-Fixed Sensors," IEEE Transactions on Biomedical Engineering, vol. 53, No. 7, pp. 1385-1393, Jul. 2006.
Dinner, "Effect of Sleep on Epilepsy," Journal of Clinical Neurophysiology, American Clinical Neurophysiology Society, 19(6), pp. 504-513, 2002.
Foerster et al., "Motion Pattern and Posture: Correctly Assessed by Calibrated Accelerometers," Forschungsgrupe Psychophysiologie, Universität Freiburg, Germany, Mar. 2000, 28 pp.
Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, 2002.
Fourcade et al., "Modeling Phase Transitions in Human Posture," Studies in Perception and Action VII, Sheena Rogers & Judith Effken (eds), Lawrence Erlbaum Associated, Inc., pp. 99-103, 2003.
Giansanti et al., "The development and test of a device for the reconstruction of 3-D position and orientation by means of a kinematic sensor assembly with rate gyroscopes and accelerometers," IEEE Transactions on Biomedical Engineering, v. 52, No. 7, pp. 1271-1277, Jul. 2005.
Goodrich et al., "The Prediction of Pain Using Measures of Sleep Quality," Pain Digest, 8:23-25, 1998.
Heinz et al., "Using Wearable Sensors for Real-time Recognition Tasks in Games of Martial Arts—An Initial Experiment," Institute for Computer Systems and Networks (CSN), UMIT—University of Health Systems, Medical Informatics and Technology Hall in Tyrol, Austria, 2006, 5 pp., http://eis.comp.lancs.ac.uk/fileadmin/relate/publication/2006-WearableSensors.pdf.
Hendelman et al., "Validity of Accelerometry for the Assessment of Moderate Intensity Physical Activity in the Field," Medicine & Science in Sports & Exercise, pp. S442-S449, 2000.
Hinckley, K., Pierce, J., Sinclair, M., Horvitz, E., *Sensing Techniques for Mobile Interaction*, ACM UIST 2000 Symposium on User Interface Software & Technology, CHI Letters 2 (2), pp. 91-100.
Husak, "Model of Tilt Sensor Systems, "ICECS 2002, 9$^{th}$ IEEE International Conference on Electronics, Circuits and Systems, vol. 1, pp. 227-230, 2002.
Karantonis et al., "Implementation of a Real-Time Human Movement Classifier Using a Triaxial Accelerometer for Ambulatory Monitoring," IEEE Transactions on Information Technology in Biomedicine, vol. 10, No. 1, pp. 156-167, Jan. 2006.
Kassam, "2005 EDP Topic "MK4": Tremor Data-Logger for Parkinson's Disease Patients," http://www.ee.ryerson.ca/~courses/edp2005/MK4.html, 3 pp., 2005.
Kerr et al., "Analysis of the sit-stand-sit movement cycle in normal subjects," Clinical Biomechanics, vol. 12, No. 4, pp. 236-245, 1977.
Kiani et al., "Computerized Analysis of Daily Life Motor Activity for Ambulatory Monitoring," Technology and Health Care 5, pp. 307-318, 1997.
Kitchin et al., "Compensating for the 0 g Offset Drift of the ADXL50 Accelerometer," Analog Devices Application Note AN-380, 2 pp.

Lau, "Strategies for Generating Prolonged Functional Standing Using Intramuscular Stimulation or Intraspinal Microstimulation," IEEE Transactions on Neural Systems and Rehabilitation Engineering, vol. 15 No. 2, pp. 273-285, Jun. 2007.
Leiper et al., "Sensory Feedback for Head Control in Cerebral Palsy," Physical Therapy, vol. 61, No. 4, pp. 512-518, Apr. 1981.
Lorussi, "Wearable, Redundant Fabric-Based Sensor Arrays for Reconstruction of Body Segment Posture," IEEE Sensors Journal, vol. 4, No. 6, pp. 808-817, Dec. 2004.
Mathie et al., "A Pilot Study of Long-Term Monitoring of Human Movements in the Home Using Accelerometer," Journal of Telemedicine and Telecare10:144-151, Jun. 2007.
Mathie et al., "Determining Activity Using a Triaxial Accelerometer," Proceedings of the Second Joint EMBS/BMES Conference, Houston, TX, pp. 2481-2482, Oct. 23-26, 2002.
Mattmann et al., "Recognizing Upper Body Postures Using Textile Strain Sensors," Proceedings Eleventh IEEE International Symposium on Wearable Computers, ISWC, pp. 29-36, 2007.
Mendez et al., "Interactions Between Sleep and Epilepsy," Journal of Clinical Neurophysiology, American Clinical Neurophysiology Society, 18(2), pp. 106-127, 2001.
Paraschiv-Ionescu et al., "Ambulatory System for the Quantitative and Qualitative Analysis of Patients Treated with Spinal Cord Stimulation," Gait and Posture, vol. 20, Issue 2, pp. 113-125, Oct. 2004.
Slyper et al., "Action Capture with Accelerometers," Eurographics/ACM SIGGRAPH Symposium on Computer Animation, Carnegie Mellon University, 7 pp., 2008.
Smith et al., "How do sleep disturbance and chronic pain inter-relate? Insights from the longitudinal and cognitive-behavioral clinical trials literature," Sleep Medicine Reviews, YSMRV 286, pp. 1-14, 2003.
Smith et al., "Presleep cognitions in Patients with Insomnia Secondary to Chronic Pain," Journal of Behavioral Medicine, vol. 24, No. 1, pp. 93-114, 2001.
Emmanuel Munguia Tapia, "Activity Recognition from Accelerometer Data for Videogame Applications," http://alumni.media.mit.edu/~emunguia/html/videogames.htm, 7 pp., Dec. 2, 2003, printed Oct. 1, 2009.
Trolier-Mckinstry et al., "Thin Film Piezoelectrics for MEMS," Journal of Electroceramics, v. 12, No. 1-2, pp. 7-17, Jan./Mar. 2004.
Tuck, "Implementing Auto-Zero Calibration Technique for Accelerometers," Freescale Semiconductor Application Note AN3447, 5 pp., Mar. 2007.
Tuisku, "Motor Activity Measured by Actometry in Neuropsychiatric Disorders," Department of Psychiatry, University of Helsinki, Helsinki, Finland, 115 pp., 2002.
Vega-Gonzalez, "Upper Limb Activity Monitoring," Arch Phys Med Rehabil, vol. 86, pp. 541-548, Mar. 2005.
Velten et al., "A New Three-Axis Accelerometer," Sensor '99—9$^{th}$ Int'l Traide Fair and Conference for Sensors/Transducers & Systems, Nürnberg, Germany, May 18-20, 1999, Sensor '99 Proceedings II, A 5.2, pp. 47-52, 1999.
PCT/US09/49005: Invitation to Pay Additional Fees dated Sep. 24, 2009, 7 pp.
U.S. Appl. No. 12/815,834, filed Jun. 15, 2010, Gerber et al.
U.S. Appl. No. 12/433,856, filed Apr. 30, 2009, Skelton et al.
U.S. Appl. No. 12/433,750, filed Apr. 30, 2009, Skelton et al.
U.S. Appl. No. 12/433,632, filed Apr. 30, 2009, Skelton et al.
U.S. Appl. No. 12/433,558, filed Apr. 30, 2009, Skelton et al.
U.S. Appl. No. 12/433,623, filed Apr. 30, 2009, Skelton et al.
U.S. Appl. No. 12/433,854, filed Apr. 30, 2009, Skelton et al.
U.S. Appl. No. 12/433,749, filed Apr. 30, 2009, Skelton et al.
U.S. Appl. No. 12/433,855, filed Apr. 30, 2009, Skelton et al.
U.S. Appl. No. 12/433,501, filed Apr. 30, 2009, Skelton et al.
U.S. Appl. No. 12/433,520, filed Apr. 30, 2009, Skelton.
U.S. Appl. No. 12/433,551, filed Apr. 30, 2009, Davis et al.
U.S. Appl. No. 12/433,588, filed Apr. 30, 2009, Skelton et al.
U.S. Appl. No. 12/433,599, filed Apr. 30, 2009, Skelton et al.
U.S. Appl. No. 12/433,442, filed Apr. 30, 2009, Skelton et al.
U.S. Appl. No. 12/433,756, filed Apr. 30, 2009, Panken et al.
U.S. Appl. No. 12/433,808, filed Apr. 30, 2009, Skelton et al.
U.S. Appl. No. 12/433,725, filed Apr. 30, 2009, Skelton et al.
U.S. Appl. No. 12/433,530, filed Apr. 30, 2009, Skelton et al.
U.S. Appl. No. 12/433,325, filed Apr. 30, 2009, Skelton et al.

(56) References Cited

OTHER PUBLICATIONS

U.S. Appl. No. 12/433,373, filed Apr. 30, 2009, Skelton et al.
U.S. Appl. No. 12/433,651, filed Apr. 30, 2009, Skelton et al.
U.S. Appl. No. 12/433,673, filed Apr. 30, 2009, Skelton et al.
U.S. Appl. No. 12/433,785, filed Apr. 30, 2009, Davis et al.
U.S. Appl. No. 12/433,827, filed Apr. 30, 2009, Skelton et al.
U.S. Appl. No. 12/433,848, filed Apr. 30, 2009, Skelton et al.
U.S. Appl. No. 12/433,840, filed Apr. 30, 2009, Skelton et al.
U.S. Appl. No. 12/433,839, filed Apr. 30, 2009, Skelton et al.
U.S. Appl. No. 12/433,803, filed Apr. 30, 2009, Skelton et al.
U.S. Appl. No. 12/433,815, filed Apr. 30, 2009, Skelton et al.
U.S. Appl. No. 12/433,684, filed Apr. 30, 2009, Skelton et al.
U.S. Appl. No. 12/771,854, filed Apr. 30, 2010, Skelton.
U.S. Appl. No. 12/433,017, filed Apr. 30, 2009, Skelton et al.
U.S. Appl. No. 12/433,004, filed Apr. 30, 2009, Panken et al.
U.S. Appl. No. 12/548,227, filed Aug. 26, 2009, Skelton et al.
U.S. Appl. No. 12/433,038, filed Apr. 30, 2009, Panken.
U.S. Appl. No. 12/433,029, filed Apr. 30, 2009, Panken et al.
U.S. Appl. No. 12/432,993, filed Apr. 30, 2010, Panken et al.
U.S. Appl. No. 12/769,461, filed Apr. 28, 2010, Sahasrabudhe et al.
U.S. Appl. No. 12/769,391, filed Apr. 28, 2010, Sahasrabudhe et al.
U.S. Appl. No. 12/769,484, filed Apr. 28, 2010, Panken et al.
Muhannad Quwaider, Subir Biswas: "Body Posture Identification using Hidden Markov Model with a Wearable Sensor Network," Bodynets '08 Proceedings of the ICST 3rd International Conference on Body Area Networks, XP002632420, 2008 (8 pgs.).
Office Action for U.S. Appl. No. 12/985,965, dated Dec. 18, 2012, 9 pp.
Exam Report from counterpart European Patent Application No. 09794975.4-1652, dated May 6, 2014, 4 pp.
Office Action from U.S. Appl. No. 12/985,127, dated Aug. 7, 2014, 13 pp.
Examination Report from counterpart European Application No. 09794975.4, dated May 6, 2014, 4 pp.
First Chinese Office Action from Chinese Counterpart Application No. 200980132522.4, dated Jan. 27, 2014, 16 pp.
Notice of Allowance from U.S. Appl. No. 12/985,965, dated Jul. 9, 2013, 9 pp.
Response to Office Action dated Aug. 7, 2014, from U.S. Appl. No. 12/985,127, filed Nov. 7, 2014, 11 pp.
Notice on the Second Office Action, and translation thereof, from Counterpart Chinese Patent Application No. 200980132522.4, dated Oct. 23, 2014, 17 pp.
Office Action from U.S. Appl. No. 14/076,702, dated Dec. 10, 2014, 6 pp.
Response to Communication dated May 6, 2014, from Counterpart European Patent Application No. 09794975.4, dated Sep. 2, 2014, 5 pp.
Office Action from U.S. Appl. No. 14/076,702, dated Dec. 10, 2014, 7 pp.
Hinckley, K., Pierce, J., Sinclair, M., Horvitz, E., Sensing Techniques for Mobile Interaction, ACM UIST 2000 Symposium on User Interface Software & Technology, CHI Letters 2 (2), pp. 91-100, Nov. 2000.
Kitchin et al., "Compensating for the 0 g Offset Drift of the ADXL50 Accelerometer," Analog Devices Application Note AN-380, 2 pp, May 1994.
Final Office Action from U.S. Appl. No. 12/985,127, dated Jan. 2, 2015, 12 pp.
Response to Office Action dated Dec. 18, 2012, from U.S. Appl. No. 12/985,965, filed Mar. 18, 2013, 12 pp.
Response to Office Action dated Dec. 10, 2014, from U.S. Appl. No. 14/076,702, filed Mar. 9, 2015, 13 pp.
Response to Final Office Action dated Jan. 2, 2015, from U.S. Appl. No. 12/985,127, filed Mar. 2, 2015, 19 pp.
Office Action from U.S. Appl. No. 14/076,702, dated Mar. 27, 2015, 9 pp.

\* cited by examiner

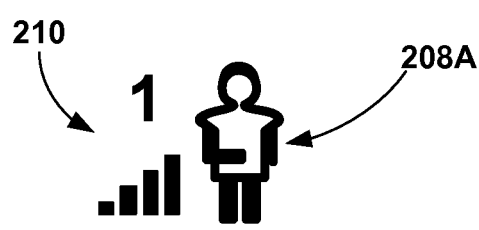
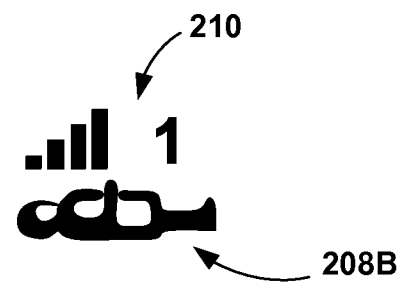
FIG. 11A FIG. 11B
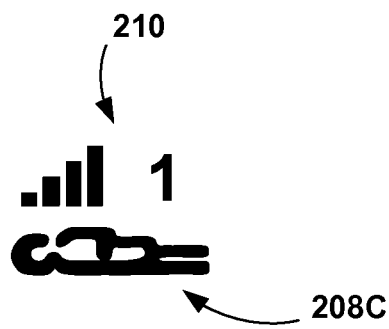
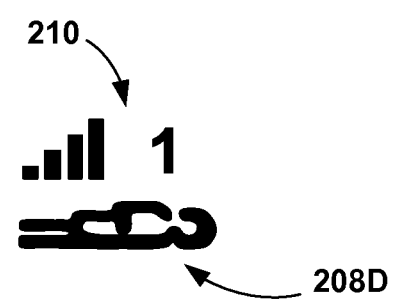
FIG. 11C FIG. 11D
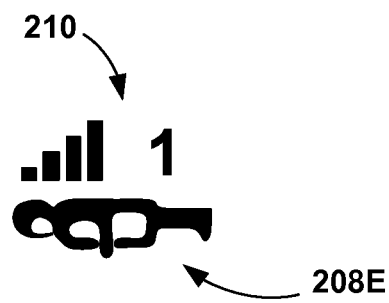
FIG. 11E

262A

262B

262C

262D

262E

262F

POSTURE STATE DISPLAY ON MEDICAL DEVICE USER INTERFACE

This application claims the benefit of U.S. Provisional Application No. 61/080,008, titled, "POSTURE STATE DISPLAY ON MEDICAL DEVICE USER INTERFACE" and filed on Jul. 11, 2008, the entire content of which is incorporated herein by reference.

TECHNICAL FIELD

The disclosure relates to medical devices and, more particularly, to programmable medical devices that deliver therapy.

BACKGROUND

A variety of medical devices are used for chronic, e.g., long-term, delivery of therapy to patients suffering from a variety of conditions, such as chronic pain, tremor, Parkinson's disease, epilepsy, urinary or fecal incontinence, sexual dysfunction, obesity, or gastroparesis. As examples, electrical stimulation generators are used for chronic delivery of electrical stimulation therapies such as cardiac pacing, neurostimulation, muscle stimulation, or the like. Pumps or other fluid delivery devices may be used for chronic delivery of therapeutic agents, such as drugs. Typically, such devices provide therapy continuously or periodically according to parameters contained within a program. A program may comprise respective values for each of a plurality of parameters, specified by a clinician.

In some cases, the patient may be allowed to activate and/or modify the therapy delivered by the medical device. For example, a patient may be provided with a patient programming device. The patient programming device communicates with a medical device to allow the patient to activate therapy and/or adjust therapy parameters. For example, an implantable medical device (IMD), such as an implantable neurostimulator, may be accompanied by an external patient programmer that permits the patient to activate and deactivate neurostimulation therapy and/or adjust the intensity of the delivered neurostimulation. The patient programmer may communicate with the IMD via wireless telemetry to control the IMD and/or retrieve information from the IMD.

SUMMARY

In general, the disclosure provides a system that displays a posture state indication to a user. A posture state represents the current posture state of the patient, e.g., as detected by a posture state detector. A posture state may refer to a patient posture or a combination of patient posture and patient activity. As a patient changes posture and activity throughout a daily routine, therapy may be adjusted to accommodate differences in the patient's response to the therapy during any particular posture state. For example, changes in posture and activity may cause therapy to become more or less effective in treating the patient's condition. An IMD may be configured to adjust therapy automatically, semi-automatically, or in response to patient input based on a patient posture state sensed by a posture state detector provided with the IMD or with another device that communicates with the IMD.

The posture state detector may generate a posture state value that may be used to categorize the patient's posture or posture and activity level as one of multiple posture states. Each posture state may be associated with one of multiple posture state indications that may be presented to the patient, e.g., by visible, audible or tactile user interface media associated with a patient programmer. Each posture state indication may be representative of a posture, an activity, or both, and indicates the posture state that is currently detected by the posture state detector for the patient. With the aid of the posture state indication, the patient may be able to more effectively monitor posture states with respect to automatic, semi-automatic or patient-directed therapy adjustments made as a function of the detected posture state.

In one example, the disclosure provides a method comprising receiving a detected posture state indicating a posture state currently occupied by a medical patient, and presenting a posture state indication representative of the detected posture state of the medical patient via a user interface of a medical device programmer.

In another example, the disclosure provides a system comprising an implantable medical device that detects a posture state currently occupied by a medical patient, and a medical device programmer that includes a user interface, wherein the programmer presents a posture state indication representative of the detected posture state of the medical patient via the user interface.

In a further example, the disclosure provides a programmer for an implantable medical device, the programmer comprising a memory that stores a plurality of posture state indications, a processor that receives a detected posture state indicating a posture state currently occupied by a medical patient, and obtains one of the posture state indications that is representative of the detected posture state of the medical patient, and a user interface that presents the posture state indication to a user.

In an additional example, the disclosure provides a computer-readable medium comprising instructions that causes a processor to receive a detected posture state indicating a posture state currently occupied by a medical patient, and present a posture state indication representative of the detected posture state of the medical patient via a user interface of a medical device programmer.

In another example, the disclosure provides a method comprising presenting an indication of electrical stimulation therapy selected for delivery to a patient on a user interface of a programmer for an implantable medical device that delivers the electrical stimulation therapy, and presenting an indication of whether the selected therapy is configured to be delivered according to a posture state of the patient via the user interface of the programmer.

In an additional example, the disclosure provides a programmer for an implantable medical device, the programmer comprising a processor that generates an indication of electrical stimulation therapy selected for delivery to a patient by the implantable medical device, and generates an indication of whether the selected therapy is configured to be delivered according to a posture state of the patient, and a user interface that presents the indications to a user.

The details of one or more aspects of the disclosure are set forth in the accompanying drawings and the description below. Other features, objects, and advantages will be apparent from the description and drawings, and from the claims.

BRIEF DESCRIPTION OF THE DRAWINGS

FIGS. 11A-11E are conceptual diagrams illustrating different posture state indications that may be displayed on a user interface.

DETAILED DESCRIPTION

Figure 1A:
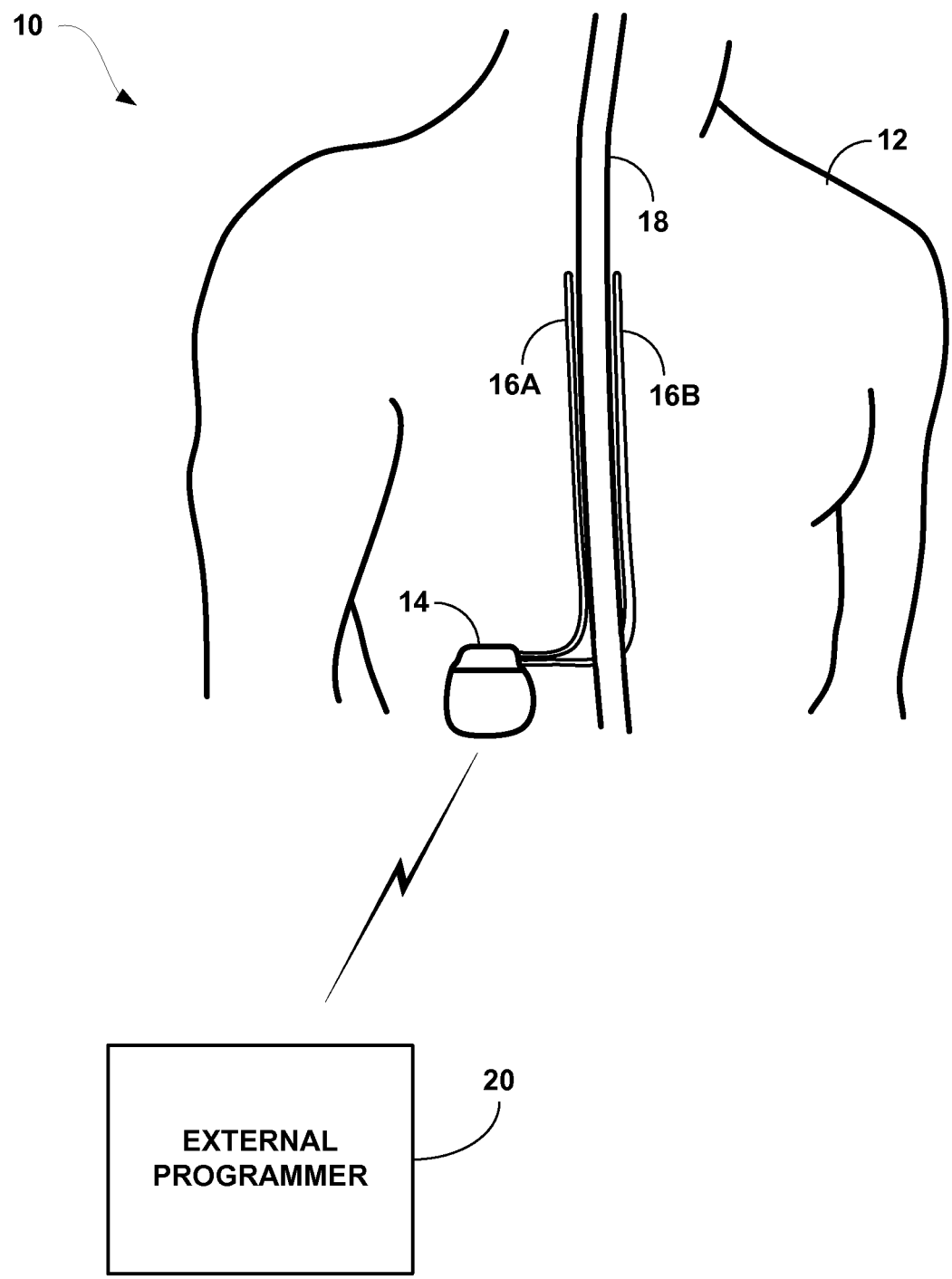
FIG. 1A is a conceptual diagram illustrating an implantable stimulation system including two implantable stimulation leads.

In some medical devices that deliver electrical stimulation therapy, therapeutic efficacy may change as the patient changes between different posture states. In general, a posture state may refer to a posture or a combination of posture and activity. Efficacy may refer, in general, to a combination of complete or partial alleviation of symptoms alone, or in combination with a degree of undesirable side effects.

Changes in posture state may cause changes in efficacy due to changes in distances between electrodes or other therapy delivery elements, e.g., due to temporary migration of leads or catheters caused by forces or stresses associated with different postures of the patient, or from changes in compression of patient tissue in different posture states. To maintain therapeutic efficacy, it may be desirable to adjust therapy parameters based on different postures and/or activities engaged by the patient to maintain effective stimulation therapy. Therapy parameters may be adjusted individually or by selecting different programs or groups of programs defining different sets of therapy parameters.

A change in efficacy due to changes in posture state may require the patient to continually manage therapy by manually adjusting certain therapy parameters, such as amplitude, pulse rate, pulse width, or electrode combination, or selecting different therapy programs to achieve more efficacious therapy throughout many different posture states. In some cases, a medical device may employ a posture state detector that detects the patient posture state. The medical device may subsequently adjust therapy parameters in response to different posture states.

Therapy adjustments in response to different posture states may be fully automatic, semi-automatic in the sense that a user may provide approval of proposed changes, or user-directed in the sense that the patient may manually adjust therapy based on the posture state indication. A user interface associated with an external programmer, e.g., a patient programmer or clinician programmer, may obtain and present a posture state indication that represents the patient posture state currently occupied by a patient. The patient posture state may be detected by a posture state module of an implantable medical device and communicated to the programmer. With the aid of the posture state indication, the patient may be able to more effectively monitor the detected posture state with respect to automatic, semi-automatic or patient-directed therapy adjustments made as a function of each detected posture state.

The posture state indication communicates the current posture state to the user, e.g., the patient. The user can then monitor the posture state indication to ascertain the therapy delivered for a particular posture state, and/or to ensure that therapy is correctly delivered. The posture state indication is generated by the IMD or external programmer and may be a visible, audible or tactile indication delivered via a user interface associated with a programmer. A visible indication may be a graphical representation of the patient's posture or activity, a symbolic icon, a word, a number, or even arrows. An audible indication may be spoken words stating a posture state, different audible tones, different numbers of tones, or other audible information generated by the programmer to indicate the posture state. A tactile indication may be different numbers of vibratory pulses delivered in sequence or vibratory pulses of different lengths, amplitudes, or frequencies.

In some implementations, a supplemental posture state indication may also be presented to the user. For example, the user interface may present the posture state indication as a graphical representation such as an icon and the supplemental posture state indication as a textual word describing the patient posture state. As another example, the user interface may present a visible posture state indication in combination with an audible or tactile posture state indication as a supplemental posture state indication. The supplemental posture state indication may, in some examples, provide a more detailed description of the patient posture state than the main posture state indication. In any case, the posture state indication may be presented alone or in combination with other therapy parameters that define the stimulation therapy delivered to the patient.

The posture state indication may allow the patient to change or confirm the sensed patient posture state represented by the posture state indication. If the posture state indication presented by the user interface does not correctly identify the current patient posture state, the patient may prompt the medical device to change the posture state indication to correctly indicate the current patient posture. The patient may select the correct posture state indication, e.g., from a drop-down menu or other list of posture state options, and the medical device may re-orient the posture state detector by associating a current posture state, e.g., a posture state detected by an IMD, with the newly selected posture state indication from the patient.

FIG. 1A is a schematic diagram illustrating an implantable stimulation system 10 including a pair of implantable electrode arrays in the form of stimulation leads 16A and 16B. Although the techniques described in this disclosure may be generally applicable to a variety of medical devices including external and implantable medical devices (IMDs), application of such techniques to IMDs and, more particularly, implantable electrical stimulators such as neurostimulators will be described for purposes of illustration. More particularly, the disclosure will refer to an implantable spinal cord stimulation (SCS) system for purposes of illustration, but without limitation as to other types of medical devices.

As shown in FIG. 1A, system 10 includes an IMD 14 and external programmer 20 shown in conjunction with a patient 12. In the example of FIG 1A, IMD 14 is an implantable electrical stimulator configured for spinal cord stimulation (SCS), e.g., for relief of chronic pain or other symptoms. Again, although FIG. 1A shows an implantable medical device, other embodiments may include an external stimulator, e.g., with percutaneously implanted leads. Stimulation energy is delivered from IMD 14 to spinal cord 18 of patient 12 via one or more electrodes of implantable leads 16A and 16B (collectively "leads 16"). In some applications, such as spinal cord stimulation (SCS) to treat chronic pain, the adjacent implantable leads 16 may have longitudinal axes that are substantially parallel to one another.

Although FIG. 1A is directed to SCS therapy, system 10 may alternatively be directed to any other condition that may benefit from stimulation therapy. For example, system 10 may be used to treat tremor, Parkinson's disease, anxiety, depression, epilepsy, urinary or fecal incontinence, sexual dysfunction, obesity, or gastroparesis. In this manner, system 10 may be configured to provide therapy taking the form of deep brain stimulation (DBS), peripheral nerve stimulation, pelvic floor stimulation, gastric stimulation, or any other stimulation therapy. Patient 12 is ordinarily a human patient.

Each of leads 16 may include electrodes (not shown in FIG. 1A), and the parameters for a program that controls delivery of stimulation therapy by IMD 14 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described for purposes of illustration. However, stimulation may be delivered in other forms such as continuous waveforms. Programs that control delivery of other therapies by IMD 14 may include other parameters, e.g., such as dosage amount, rate, or the like for drug delivery.

In the example of FIG. 1A, leads 16 carry one or more electrodes that are placed adjacent to the target tissue of the spinal cord. One or more electrodes may be disposed at a distal tip of a lead 16 and/or at other positions at intermediate points along the lead. Leads 16 may be implanted and coupled to IMD 14. Alternatively, as mentioned above, leads 16 may be implanted and coupled to an external stimulator, e.g., through a percutaneous port. In some cases, an external stimulator may be a trial or screening stimulation that used on a temporary basis to evaluate potential efficacy to aid in consideration of chronic implantation for a patient. In additional embodiments, IMD 14 may be a leadless stimulator with one or more arrays of electrodes arranged on a housing of the stimulator rather than leads that extend from the housing.

The stimulation may be delivered via selected combinations of electrodes carried by one or both of leads 16. The target tissue may be any tissue affected by electrical stimulation energy, such as electrical stimulation pulses or waveforms. Such tissue includes nerves, smooth muscle, and skeletal muscle. In the example illustrated by FIG. 1A, the target tissue is spinal cord 18. Stimulation of spinal cord 18 may, for example, prevent pain signals from traveling through the spinal cord and to the brain of the patient. Patient 12 may perceive the interruption of pain signals as a reduction in pain and, therefore, efficacious therapy results.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some embodiments, electrode arrays may include electrode segments, which may be arranged at respective positions around a periphery of a lead, e.g., arranged in the form of one or more segmented rings around a circumference of a cylindrical lead.

In the example of FIG. 1A, stimulation energy is delivered by IMD 14 to the spinal cord 18 to reduce the amount of pain perceived by patient 12. As described above, IMD 14 may be used with a variety of different pain therapies, such as peripheral nerve stimulation (PNS), peripheral nerve field stimulation (PNFS), DBS, cortical stimulation (CS), pelvic floor stimulation, gastric stimulation, and the like. The electrical stimulation delivered by IMD 14 may take the form of electrical stimulation pulses or continuous stimulation waveforms, and may be characterized by controlled voltage levels or controlled current levels, as well as pulse width and pulse rate in the case of stimulation pulses.

In some examples, IMD 14 may deliver stimulation therapy according to one or more programs. A program defines one or more parameters that define an aspect of the therapy delivered by IMD 14 according to that program. For example, a program that controls delivery of stimulation by IMD 14 in the form of pulses may define one or more therapy parameters such as a voltage or current pulse amplitude, a pulse width, a pulse rate, for stimulation pulses delivered by IMD 14 according to that program. Moreover, therapy may be delivered according to multiple programs, wherein multiple programs are contained within each of a multiple of groups.

Each program group may support an alternative therapy selectable by patient 12, and IMD 14 may deliver therapy according to the multiple programs. IMD 14 may rotate through the multiple programs of the group when delivering stimulation such that numerous conditions of patient 12 are treated. As an illustration, in some cases, stimulation pulses formulated according to parameters defined by different programs may be delivered on a time-interleaved basis. For example, a group may include a program directed to leg pain, a program directed to lower back pain, and a program directed to abdominal pain. In this manner, IMD 14 may treat different symptoms substantially simultaneously.

During use of IMD 14 to treat patient 12, movement of patient 12 among different posture states may affect the ability of IMD 14 to deliver consistent efficacious therapy. For example, leads 16 may migrate toward IMD 14 when patient 12 bends over, resulting in displacement of electrodes and possible disruption in delivery of effective therapy. For example, stimulation energy transferred to target tissue may be reduced due to electrode migration, causing reduced efficacy in terms of relief of symptoms such as pain. As another example, leads 16 may be compressed towards spinal cord 18 when patient 12 lies down. Such compression may cause an increase in the amount of stimulation energy transferred to target tissue. In this case, the amplitude of stimulation therapy may need to be decreased to avoid causing patient 12 additional pain or unusual sensations, which may be considered undesirable side effects that undermine overall efficacy.

Also, posture state changes may present changes in symptoms or symptom levels, e.g., pain level. In some examples, to avoid interruptions in effective therapy, IMD 14 may include a posture state module that detects the patient posture state. The IMD automatically adjusts stimulation according to the posture state detection, thereby providing posture-state responsive therapy. For example, the posture state module may include one or more accelerometers that detect when patient 12 occupies a posture state in which it is appropriate to decrease the stimulation amplitude, e.g., when patient 12 lies down. The IMD may automatically reduce stimulation amplitude so that patient 12 does not manually have to do so. Example posture states may include "Upright," "Upright and Active," "Lying Down," and so forth.

As will be described in greater detail below, in some examples, IMD 14 may be configured to automatically decrease stimulation amplitude when it detects that patient 12 lies down. The amplitude adjustment may be configured to be decreased at a rate suitable to prevent undesirable effects, e.g., such as the effects due to the compression of leads 16 towards spinal cord 18 when patient lies down. In some examples, IMD 14 may be configured to decrease the stimulation amplitude to a suitable amplitude value substantially immediately upon detection by IMD 14 that patient 12 is lying down. In other examples, the stimulation amplitude may not be decreased substantially immediately by IMD 14 upon detection of patient 12 lying down, but instead IMD 14 may decrease the stimulation amplitude to a suitable amplitude level at a rate of change that is suitable to prevent patient 12 from experiencing undesirable stimulation effects, e.g., due to increased transfer of stimulation energy. In some examples, IMD 14 may substantially instantaneously decrease the stimulation amplitude to a suitable amplitude value when IMD detects that patient 12 is lying down.

Many other examples of reduced efficacy due to increased coupling or decreased coupling of stimulation energy to target tissue may occur due to changes in posture and/or activity level associated with patient posture state. To avoid or reduce possible disruptions in effective therapy due to posture state changes, IMD 14 may include a posture state module that detects the posture state of patient 12 and causes the IMD 14 to automatically adjust stimulation according to the posture state detection. For example, a posture state module may include an activity sensor such as an accelerometer that detects when patient 12 lies down, stands up, or otherwise changes posture.

In response to a posture state detected by the posture state module, IMD 14 may change program group, program, stimulation amplitude, pulse width, pulse rate, and/or one or more other parameters, groups or programs to maintain therapeutic efficacy. When a patient lies down, for example, IMD 14 may automatically reduce stimulation amplitude so that patient 12 does not need to reduce stimulation amplitude manually. In other cases, IMD 14 may automatically increase stimulation amplitude based on posture state. In some cases, IMD 14 may communicate with external programmer 20 to present a proposed change in stimulation in response to a posture state change, and receive approval or rejection of the change from a user, such as patient 12 or a clinician, before automatically applying the therapy change. In some examples, posture state detection may also be used to provide notifications, such as providing notification via a wireless link to a care giver that a patient has potentially experienced a fall.

Referring still to FIG. 1A, a user, such as a clinician or patient 12, may interact with a user interface of external programmer 20 to program IMD 14. Programming of IMD 14 may refer generally to the generation and transfer of commands, programs, or other information to control the operation of IMD 14. For example, external programmer 20 may transmit programs, parameter adjustments, program selections, group selections, or other information to control the operation of IMD 14, e.g., by wireless telemetry. As one example, external programmer 20 may transmit parameter adjustments to support therapy changes due to posture changes by patient 12. As another example, a user may select programs or program groups. Again, a program may be characterized by an electrode combination, electrode polarities, voltage or current amplitude, pulse width, pulse rate, and/or duration. A group may be characterized by multiple programs that are delivered simultaneously or on an interleaved or rotating basis.

The user interface of external programmer 20 may indicate to the user the posture state in which the patient 12 currently resides. This patient posture state may be a static posture that does not take into account activity level, an activity level that does not take into account posture, or some combination of the posture and activity level that describes the physical position and movement of patient 12. As an example, posture may be characterized as one of the following postures: standing, sitting, lying down on back, lying down on front, lying down on left side, lying down on right side. Activity level may be characterized as one of: high, medium and low, or, e.g., walking, biking, running, or the like.

Posture state may indicate a combination of one of the above postures with one of the above activity levels. For some postures, such as lying down postures, the posture state may not need to consider activity level, as the patient may be less likely to undertake any significant activity in such postures. In other cases, all posture states may take into account posture and activity level, even if there is minimal activity in a particular posture. Posture state may be determined based on detected posture information and/or activity level information generated by a posture state module, which may include one or more accelerometers or other posture or activity level sensors.

The patient posture state may be represented by a posture state indication presented to patient 12 and generated by the user interface of programmer 20 as a visible, audible, or tactile indication. When presented as a visible indication, the posture state indication may be, for example, a graphical representation, a symbolic icon, a textual representation such as word or number, an arrow, or any other type of indication. The visible indication may be presented via a display, such as an a liquid crystal display (LCD), dot matrix display, organic light-emitting diode (OLED) display, touch screen, or the like. In other cases, the visible indication may be provided in a translucent area that is selectively backlit to indicate a posture. An audible indication may be produced by programmer 20 as spoken words stating a posture state, or different audible tones, different numbers of tones, or other audible information generated by the programmer to indicate posture state. A tactile indication may be produced by programmer 20 different numbers of vibratory pulses delivered in sequence or vibratory pulses of different lengths, amplitudes, or frequencies.

Programmer 20 may present multiple indications representative of different patient posture states. IMD 14 may communicate a patient posture state according to a posture state parameter value sensed by a posture state module to external programmer 20, e.g., by wireless telemetry. IMD 14 may communicate the detected posture state, i.e., posture state detection, or a posture state parameter value used to detect the posture state. For example, IMD 14 may transmit a posture state detection to programmer 20 on a periodic, intermittent or continuous basis or in response to a posture state change. Alternatively, programmer 20 may request a posture state detection from IMD 14 on a periodic, intermittent or continuous basis. The posture state detection provided from IMD 14 to programmer 20 may be a posture state value that is interpreted to determined posture state, or simply an indication of the detected posture state, e.g., upright, lying front, lying back, lying left, lying right, or the like. External programmer 20 then may select and present the associated posture state indication.

In some cases, external programmer 20 may be characterized as a physician or clinician programmer if it is primarily intended for use by a physician or clinician. In other cases, external programmer 20 may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use.

IMD 14 may be constructed with a biocompatible housing, such as titanium or stainless steel, or a polymeric material such as silicone or polyurethane, and surgically implanted at a site in patient 18 near the pelvis. IMD 14 may also be implanted in patient 12 at a location minimally noticeable to patient 12. Alternatively, IMD 14 may be external with percutaneously implanted leads. For SCS, IMD 14 may be located in the lower abdomen, lower back, upper buttocks, or other location to secure IMD 14. Leads 16 may be tunneled from IMD 14 through tissue to reach the target tissue adjacent to spinal cord 18 for stimulation delivery.

At the distal tips of leads 16 are one or more electrodes (not shown) that transfer the electrical stimulation from the lead to the tissue. The electrodes may be electrode pads on a paddle lead, circular (e.g., ring) electrodes surrounding the body of leads 16, conformable electrodes, cuff electrodes, segmented electrodes, or any other type of electrodes capable of forming unipolar, bipolar or multipolar electrode configurations for therapy. In general, ring electrodes arranged at different axial positions at the distal ends of leads 16 will be described for purposes of illustration.

Figure 1B:
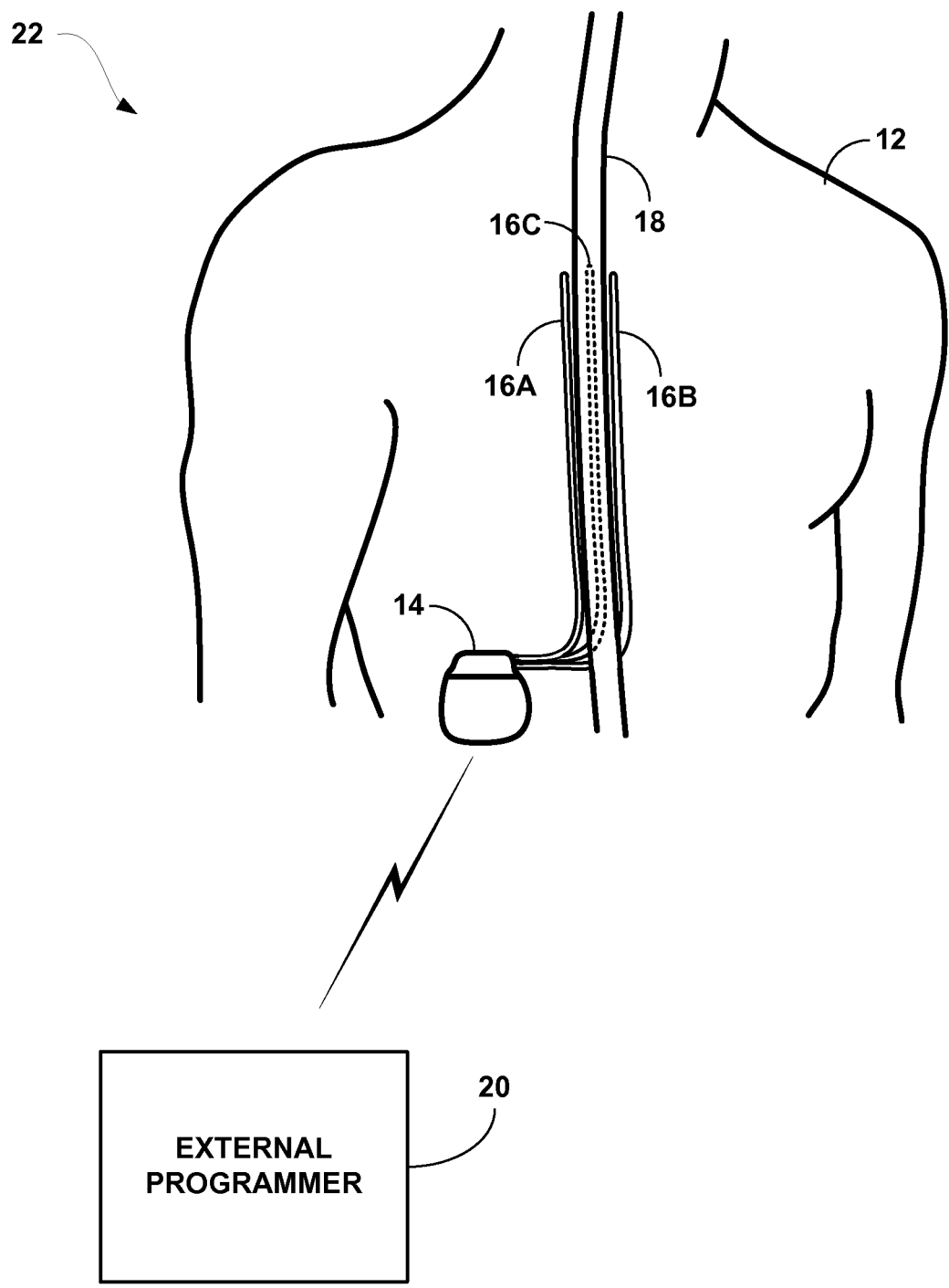
FIG. 1B is a conceptual diagram illustrating an implantable stimulation system including three implantable stimulation leads.

FIG. 1B is a conceptual diagram illustrating an implantable stimulation system 22 including three implantable stimulation leads 16A, 16B, 16C (collectively leads 16). System 22 generally conforms to system 10 of FIG. 1A, but includes a third lead. Accordingly, IMD 14 may deliver stimulation via combinations of electrodes carried by all three leads 16, or a subset of the three leads. The third lead, e.g., lead 16C, may include a greater number of electrodes than leads 16A and 16B and be positioned between leads 16A and 16B or on one side of either lead 16A or 16B. External programmer 20 may be initially told the number and configuration of leads 16 in order to appropriately program stimulation therapy.

For example, leads 16A and 16B could include four electrodes, while lead 16C includes eight or sixteen electrodes, thereby forming a so-called 4-8-4 or 4-16-4 lead configuration. Other lead configurations, such as 8-16-8, 8-4-8, 16-8-16, 16-4-16, are possible. In some cases, electrodes on lead 16C may be smaller in size and/or closer together than the electrodes of leads 16A or 16B. Movement of lead 16C due to changing activities or postures of patient 12 may, in some instances, more severely affect stimulation efficacy than movement of leads 16A or 16B. Patient 12 may further benefit from the ability of IMD 14 to detect posture states and associated changes and automatically adjust stimulation therapy to maintain therapy efficacy in a three lead system 22.

Figure 1C:
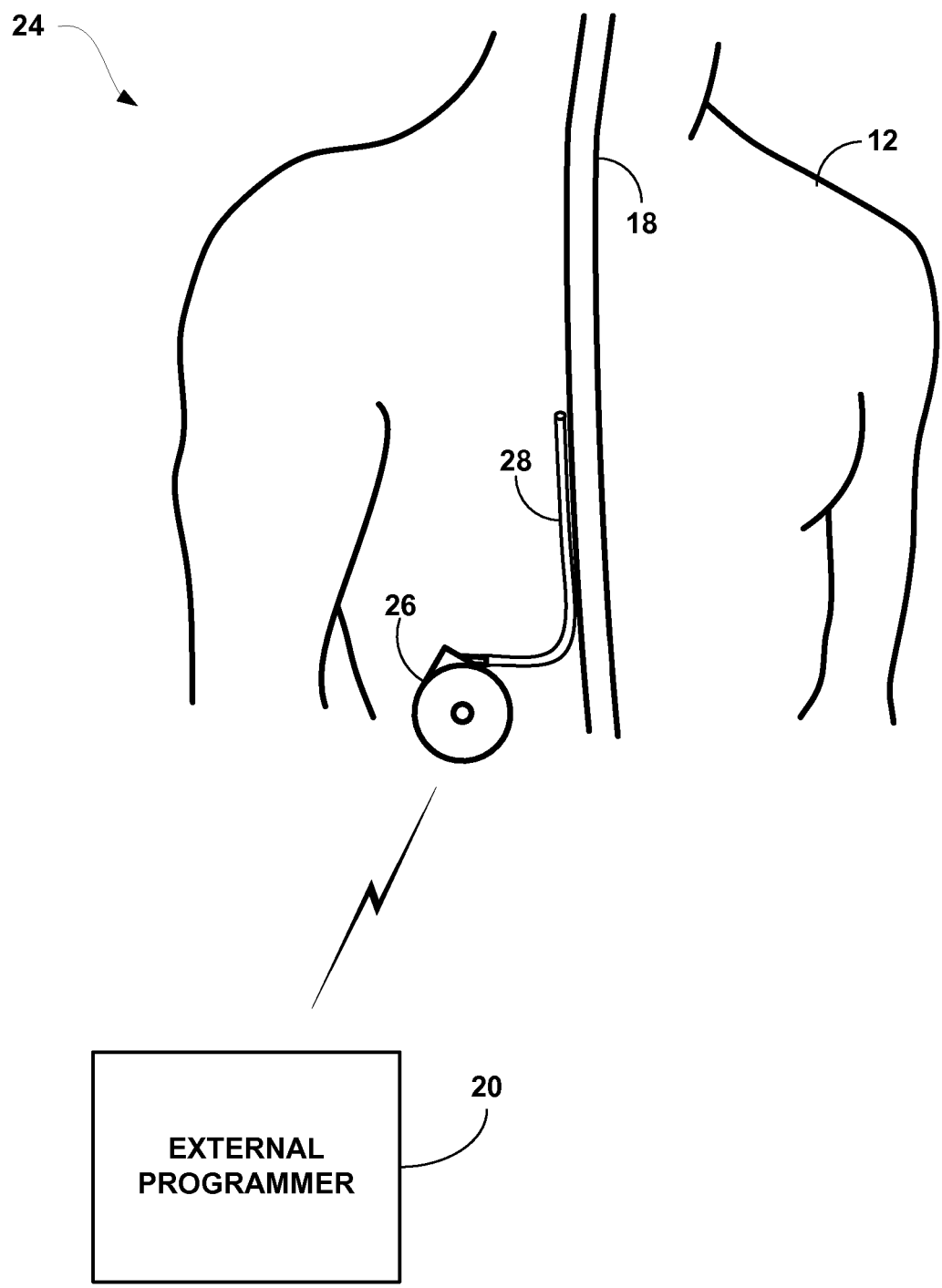
FIG. 1C is a conceptual diagram illustrating an implantable drug delivery system including a delivery catheter.

FIG. 1C is a conceptual diagram illustrating an implantable drug delivery system 24 including one delivery catheter 28 coupled to IMD 26. As shown in the example of FIG 1C, drug delivery system 24 is substantially similar to systems 10 and 22. However, drug delivery system 24 performs the similar therapy functions via delivery of drug stimulation therapy instead of electrical stimulation therapy. IMD 26 functions as a drug pump in the example of FIG 1C, and IMD 26 communicates with external programmer 20 to initialize therapy or modify therapy during operation. In addition, IMD 26 may be refillable to allow chronic drug delivery.

Although IMD 26 is shown as coupled to only one catheter 28 positioned along spinal cord 18, additional catheters may also be coupled to IMD 26. Multiple catheters may deliver drugs or other therapeutic agents to the same anatomical location or the same tissue or organ. Alternatively, each catheter may deliver therapy to different tissues within patient 12 for the purpose of treating multiple symptoms or conditions. In some embodiments, IMD 26 may be an external device which includes a percutaneous catheter that forms catheter 28 or that is coupled to catheter 28, e.g., via a fluid coupler. In other embodiments, IMD 26 may include both electrical stimulation as described in IMD 14 and drug delivery therapy.

IMD 26 may also operate using parameters that define the method of drug delivery. IMD 26 may include programs, or groups of programs, that define different delivery methods for patient 14. For example, a program that controls delivery of a drug or other therapeutic agent may include a titration rate or information controlling the timing of bolus deliveries. Patient 14 may use external programmer 20 to adjust the programs or groups of programs to regulate the therapy delivery.

Similar to IMD 14, IMD 26 may include a posture state module that monitors the patient posture state. IMD 26 may adjusts therapy based on posture state. For example, the posture state module may indicate that patient 12 transitions from lying down to standing up. IMD 26 may automatically increase the rate of drug delivered to patient 12 in the standing position if patient 12 has indicated that pain increased when standing. This automated adjustment to therapy based upon posture state may be activated for all or only a portion of the programs used by IMD 26 to deliver therapy.

Figure 2:
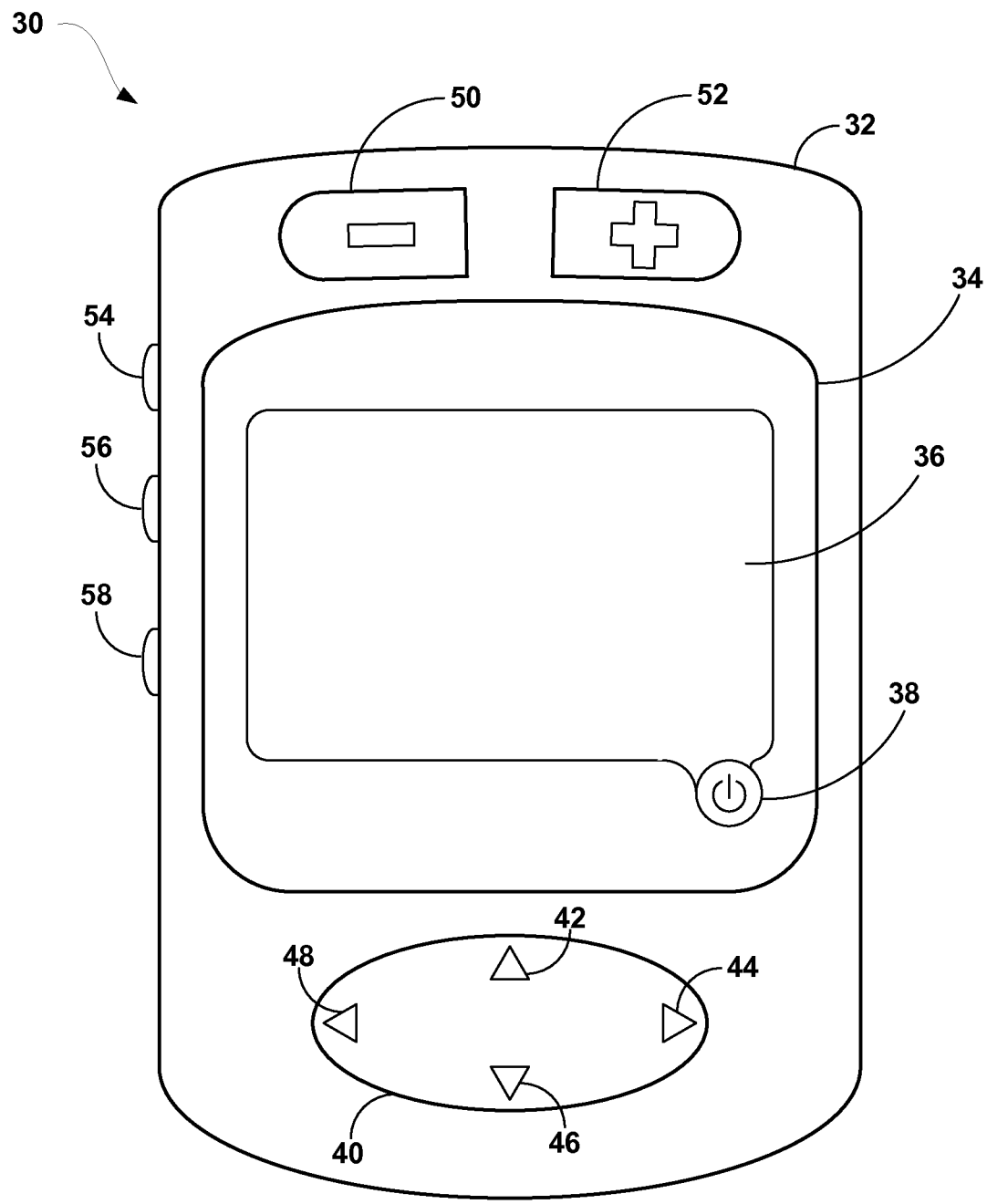
FIG. 2 is a conceptual diagram illustrating an example patient programmer for programming stimulation therapy delivered by an implantable medical device.

FIG. 2 is a conceptual diagram illustrating an example patient programmer 30 for programming stimulation therapy delivered by an implantable medical device. Patient programmer 30 is an example embodiment of external programmer 20 illustrated in FIGS. 1A, 1B and 1C and may be used with either IMD 14 or IMD 26. In alternative embodiments, patient programmer 30 may be used with an external medical device. As shown in FIG. 2, patient programmer 30 provides a user interface (not shown) for a user, such as patient 12, to manage and program stimulation therapy. In addition, patient programmer 30 presents a posture state indication to patient 12 in order to represent the patient posture state. Patient programmer 30 is protected by housing 32, which encloses circuitry necessary for patient programmer 30 to operate.

Patient programmer 30 also includes display 36, power button 38, increase button 52, decrease button 50, sync button 58, stimulation ON button 54, and stimulation OFF button 56. Cover 34 protects display 36 from being damaged during use of patient programmer 30. Patient programmer 30 also includes control pad 40 which allows a user to navigate through items displayed on display 36 in the direction of arrows 42, 44, 46, and 48. In some embodiments, the buttons and pad 40 may take the form of soft keys (e.g., with functions and contexts indicated on display 36), with functionality that may change, for example, based on current programming operation or user preference. In alternative embodiments, display 36 may be a touch screen in which patient 12 may interact directly with display 36 without the use of control pad 40 or even increase button 52 and decrease button 50.

In the illustrated embodiment, patient programmer 30 is a hand held device. Patient programmer 30 may accompany patient 12 throughout a daily routine. In some cases, patient programmer 30 may be used by a clinician when patient 12 visits the clinician in a hospital or clinic. In other embodiments, patient programmer 30 may be a clinician programmer that remains with the clinician or in the clinic and is used by the clinician and/or patient 12 when the patient is in the clinic. In the case of a clinician programmer, small size and portability may be less important. Accordingly, a clinician programmer may be sized larger than a patient programmer, and it may provide a larger screen for more full-featured programming.

Housing 32 may be constructed of a polymer, metal alloy, composite, or combination material suitable to protect and contain components of patient programmer 30. In addition, housing 32 may be partially or completely sealed such that fluids, gases, or other elements may not penetrate the housing and affect components therein. Power button 38 may turn patient programmer 30 ON or OFF as desired by patient 12. Patient 12 may control the illumination level, or backlight level, of display 36 by using control pad 40 to navigate through the user interface and increase or decrease the illumination level with decrease and increase buttons 50 and 52, respectively. In some embodiments, illumination of display 36 may be controlled by a knob that rotates clockwise and counter-clockwise. Patient programmer 30 may be prevented from turning OFF during telemetry with IMD 14 or another device to prevent the loss of transmitted data or the stalling of normal operation. Alternatively, patient programmer 30 and IMD 14 may include instructions that handle possible unplanned telemetry interruption, such as battery failure or inadvertent device shutdown.

Display 36 may be a liquid crystal display (LCD), dot matrix display, organic light-emitting diode (OLED) display, touch screen, or similar monochrome or color display capable of providing visible information to patient 12. Display 36 may provide a user interface regarding current stimulation therapy, posture state information, provide a user interface for receiving feedback or medication input from patient 12, display an active group of stimulation programs, and display operational status of patient programmer 30 or IMDs 14 or 26. For example, patient programmer 30 may provide a scrollable list of groups, and a scrollable list of programs within each group, via display 36. In addition, display 36 may present a visible posture state indication based on the posture state detection. Further, display 36 may present therapy adjustment information stored during a record mode of IMD 14, in which IMD 14 records posture state transitions, therapy adjustments, or other information, and even present nominal or suggested therapy parameters for a plurality of programs. Patient 12 may then selectively set the plurality of programs to the respective nominal or suggested therapy parameters via a single confirmation input. As described herein, patient programmer 30 may be configured to perform any tasks described with respect to clinician programmer 60 or another external programmer 20.

Control pad 40 allows patient 12 to navigate through items displayed on display 36. Patient 12 may press control pad 40 on any of arrows 42, 44, 46, and 48 in order to move to another item on display 36 or move to another screen not currently shown on the display. In some embodiments, pressing the middle of control pad 40 may select any item highlighted in display 36. In other embodiments, scroll bars, a scroll wheel, individual buttons, or a joystick may perform the complete or partial functions of control pad 40. In alternative embodiments, control pad 40 may be a touch pad that allows patient 12 to move a cursor within the user interface displayed on display 36 to manage therapy.

Decrease button 50 and increase button 52 provide an input mechanism for patient 12. In general, decrease button 50 may decrease the value of a highlighted stimulation parameter every time the decrease button is pressed. In contrast, increase button 52 may increase the value of a highlighted stimulation parameter one step every time the increase button is pressed. While buttons 50 and 52 may be used to control the value of any stimulation parameter, buttons 50 and 52 may also control patient feedback input. When either of buttons 50 and 52 is selected, patient programmer 30 may initialize communication with IMD 14 or 26 to change therapy accordingly.

When depressed by patient 12, stimulation ON button 54 directs programmer 30 to generate a command for communication to IMD 14 that turns on stimulation therapy. Stimulation OFF button 56 turns off stimulation therapy when depressed by patient 12. Sync button 58 forces patient programmer 30 to communicate with IMD 14. When patient 12 enters an automatic posture response screen of the user interface, pressing sync button 58 turns on the automatic posture response to allow IMD 14 to automatically change therapy according to the posture state of patient 12. Pressing sync button 58 again, when the automatic posture response screen is displayed, turns off the automatic posture response. In the example of FIG. 2, patient 12 may use control pad 40 to adjust the volume, contrast, illumination, time, and measurement units of patient programmer 30.

In some embodiments, buttons 54 and 56 may be configured to perform operational functions related to stimulation therapy or the use of patient programmer 30. For example, buttons 54 and 56 may control the volume of audible sounds produced by patient programmer 30, wherein button 54 increases the volume and button 56 decreases the volume. Button 58 may be pressed to enter an operational menu that allows patient 12 to configure the user interface of patient programmer 30 to the desires of patient 12. For example, patient 12 may be able to select a language, backlight delay time, display 36 brightness and contrast, or other similar options. In alternative embodiments, buttons 50 and 52 may control all operational and selection functions, such as those related to audio volume or stimulation therapy.

Patient programmer 30 may take other shapes or sizes not described herein. For example, patient programmer 30 may take the form of a clam-shell shape, similar to some cellular phone designs. When patient programmer 30 is closed, some or all elements of the user interface may be protected within the programmer. When patient programmer 30 is opened, one side of the programmer may contain a display while the other side may contain input mechanisms. In any shape, patient programmer 30 may be capable of performing the requirements described herein. Alternative embodiments of patient programmer 30 may include other input mechanisms such as a keypad, microphone, camera lens, or any other media input that allows the user to interact with the user interface provided by patient programmer 30.

In alternative embodiments, the buttons of patient programmer 30 may perform different functions than the functions provided in FIG. 2 as an example. In addition, other embodiments of patient programmer 30 may include different button layouts or different numbers of buttons. For example, patient programmer 30 may even include a single touch screen that incorporates all user interface functionality with a limited set of buttons or no other buttons.

Figure 3:
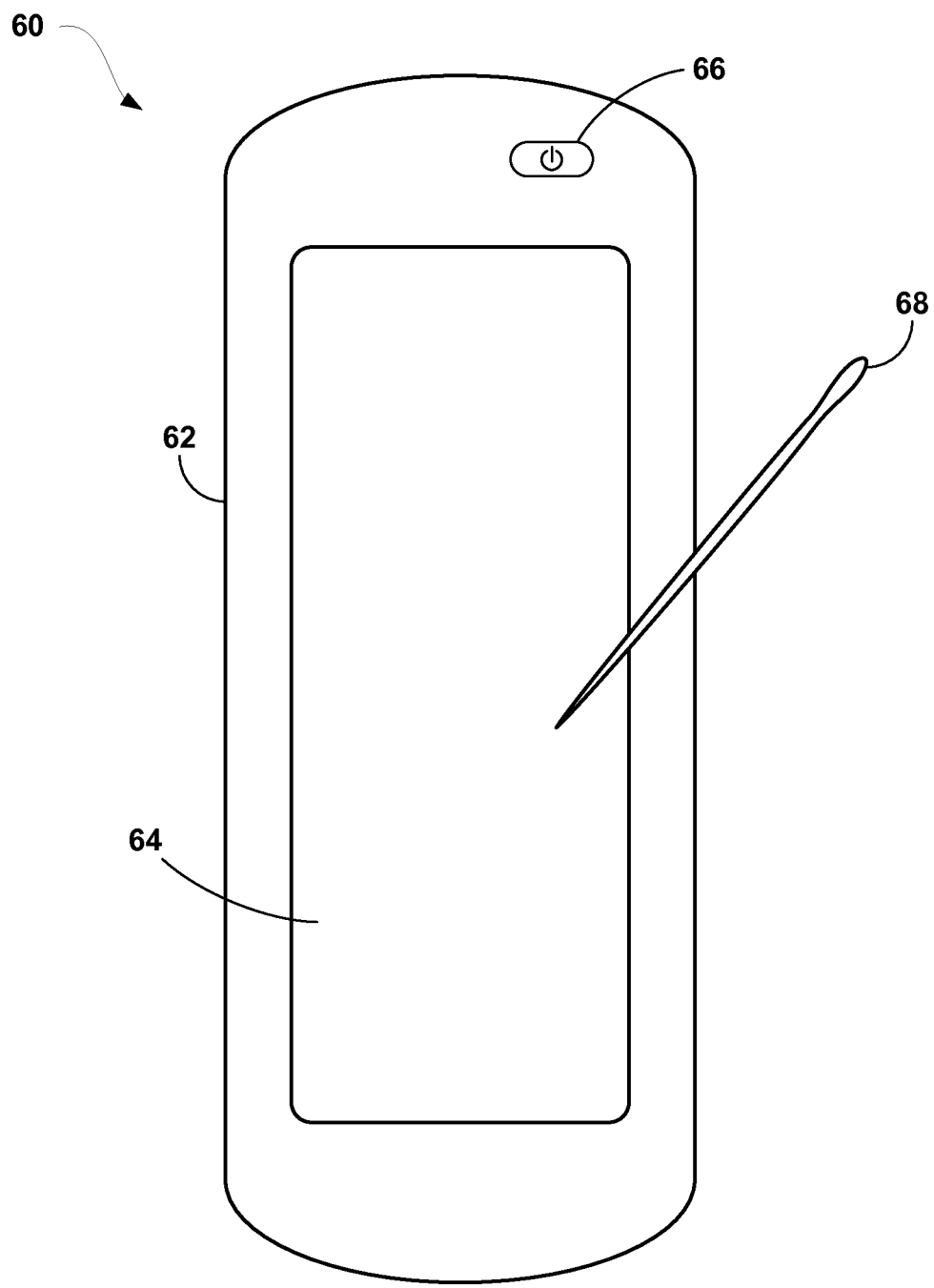
FIG. 3 is a conceptual diagram illustrating an example clinician programmer for programming stimulation therapy delivered by an implantable medical device.

FIG. 3 is a conceptual diagram illustrating an example clinician programmer 60 for programming stimulation therapy delivered by an implantable medical device. Clinician programmer 60 is an example embodiment of external programmer 20 illustrated in FIGS. 1A, 1B and 1C and may be used with either IMD 14 or IMD 26. In alternative embodiments, clinician programmer 60 may be used with an external medical device. As shown in FIG. 3, clinician programmer 60 provides a user interface (not shown) for a user, such as a clinician, physician, technician, or nurse, to manage and program stimulation therapy. In some embodiments, clinician programmer 60 may also be able to present the posture state indication to the user or even select which types of posture state indications will be displayed for patient 12. Clinician programmer 60 is protected by housing 62, which encloses circuitry necessary for operation of clinician programmer 60.

Clinician programmer 60 is used by the clinician or other user to modify and review therapy to patient 12. The clinician may define each therapy parameter value for each of the programs that define stimulation therapy. The therapy parameters, such as amplitude, may be defined specifically for each of the posture states that patient 12 will be engaged in during therapy. In addition, the clinician may use clinician programmer 60 to define each posture state of patient 12 by using posture cones or other posture volumes as described herein or other techniques for associating posture state sensor output to the posture state of patient 12.

Clinician programmer 60 includes display 64 and power button 66. In the example of FIG. 3, display 64 is a touch screen that accepts user input via touching certain areas within display 64. The user may use stylus 68 to touch display 64 and select virtual buttons, sliders, keypads, dials, or other such representations presented by the user interface shown by display 64. In some embodiments, the user may be able to touch display 64 with a finger, pen, or any other pointing device. In alternative embodiments, clinician programmer 60 may include one or more buttons, keypads, control pads, touch pads, or other devices that accept user input, similar to patient programmer 30.

In the illustrated embodiment, clinician programmer 60 is a hand held device. Clinician programmer 60 may be used within the clinic or on in-house patient calls. Clinician programmer 60 may be used to communicate with multiple IMDs 14 and 26 within different patients. In this manner, clinician programmer 60 may be capable of communicating with many different devices and retain patient data separate for other patient data. In some embodiments, clinician programmer 60 may be a larger device that may be less portable, such as a notebook computer, workstation, or even a remote computer that communicates with IMD 14 or 26 via a remote telemetry device.

Most, if not all, of the functions of clinician programmer may be completed via the touch screen of display 64. The user may program stimulation therapy, modify programs or groups, retrieve stored therapy data, retrieve posture state information, define posture states and other activity information, change the contrast and backlighting of display 64, or any other therapy related function. In addition, clinician programmer 60 may be capable of communicating with a networked server in order to send or receive an email or other message, retrieve programming instructions, access a help guide, send an error message, or perform any other function that may be beneficial to prompt therapy.

In some cases, all processing may be performed in IMD 14 and distributed to clinician programmer 60 only for presentation to the clinician. Alternatively, two or more of IMD 14, clinician programmer 60, patient programmer 30, or another computing device may share in the processing duties of processing therapy adjustment information and any other data prior to presenting the information on clinician programmer 60.

Housing 62 may be constructed of a polymer, metal alloy, composite, or combination material suitable to protect and contain components of clinician programmer 60. In addition, housing 62 may be partially or completely sealed such that fluids, gases, or other elements may not penetrate the housing and affect components therein. Power button 66 may turn clinician programmer 60 ON or OFF as desired by the user. Clinician programmer 60 may require a password, biometric input, or other security measure to be entered and accepted before the user can use clinician programmer 60.

Clinician programmer 60 may take other shapes or sizes not described herein. For example, clinician programmer 60 may take the form of a clam-shell shape, similar to some cellular phone designs. When clinician programmer 60 is closed, at least a portion of display 64 is protected within housing 62. When clinician programmer 60 is opened, one side of the programmer may contain a display while the other side may contain input mechanisms. In any shape, clinician programmer 60 may be capable of performing the requirements described herein.

Figure 4:
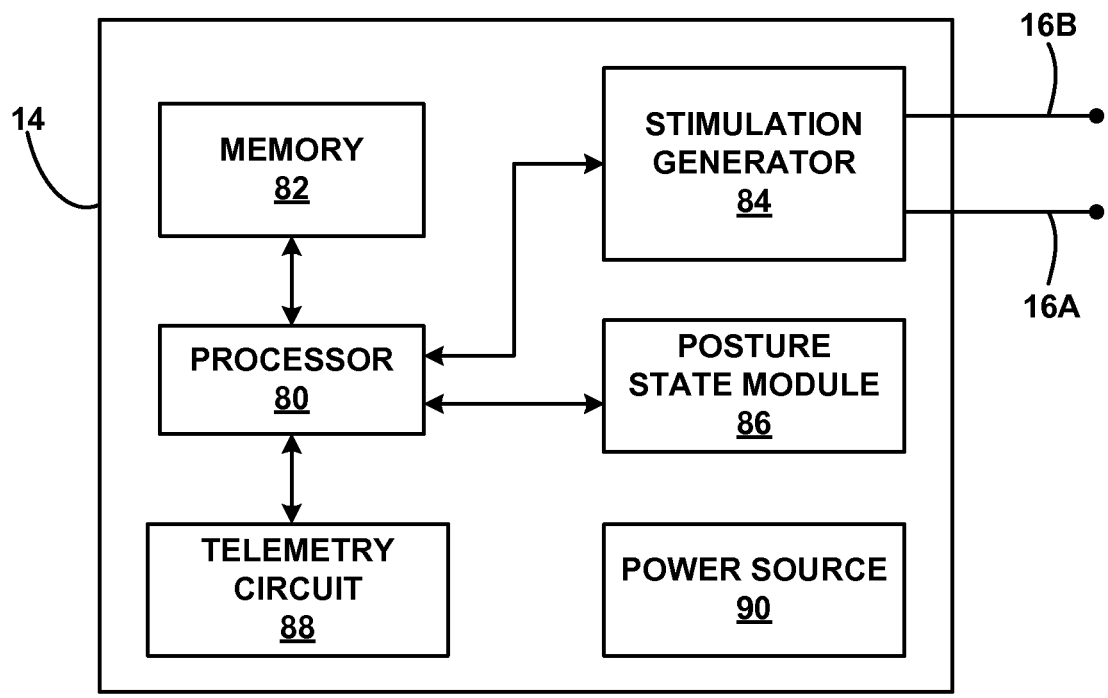
FIG. 4 is a functional block diagram illustrating various components of an implantable electrical stimulator.

FIG. 4 is a functional block diagram illustrating various components of an IMD 14. In the example of FIG. 4, IMD 14 includes a processor 80, memory 82, stimulation generator 84, posture state module 86, telemetry circuit 88, and power source 90. Memory 82 may store instructions for execution by processor 80, stimulation therapy data, posture state information, posture state indications, and any other information regarding therapy or patient 12. Therapy information may be recorded for long-term storage and retrieval by a user, and the therapy information may include any data created by or stored in IMD 14. Memory 82 may include separate memories for storing instructions, posture state information, program histories, and any other data that may benefit from separate physical memory modules.

Processor 80 controls stimulation generator 84 to deliver electrical stimulation via electrode combinations formed by electrodes in one or more electrode arrays. For example, stimulation generator 84 may deliver electrical stimulation therapy via electrodes on one or more leads 16, e.g., as stimulation pulses or continuous waveforms. Components described as processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Stimulation generator 84 may include stimulation generation circuitry to generate stimulation pulses or waveforms and switching circuitry to switch the stimulation across different electrode combinations, e.g., in response to control by processor 80. In particular, processor 80 may control the switching circuitry on a selective basis to cause stimulation generator 84 to deliver electrical stimulation to selected electrode combinations and to shift the electrical stimulation to different electrode combinations in a first direction or a second direction when the therapy must be delivered to a different location within patient 12. In other embodiments, stimulation generator 84 may include multiple current sources to drive more than one electrode combination at one time. In this case, stimulation generator 84 may decrease current to the first electrode combination and simultaneously increase current to the second electrode combination to shift the stimulation therapy.

An electrode combination may be represented by a data stored in a memory location, e.g., in memory 82, of IMD 14. Processor 80 may access the memory location to determine the electrode combination and control stimulation generator 84 to deliver electrical stimulation via the indicated electrode combination. To change electrode combinations, amplitudes, pulse rates, or pulse widths, processor 80 may command stimulation generator 84 to make the appropriate change or changes to therapy according to instructions within memory 82 and rewrite the memory location to indicate the changed therapy. In other embodiments, rather than rewriting a single memory location, processor 80 may make use of two or more memory locations.

When activating stimulation, processor 80 may access not only the memory location specifying the electrode combination but also other memory locations specifying various stimulation parameters such as voltage or current amplitude, pulse width and pulse rate. Stimulation generator 84, e.g., under control of processor 80, then makes use of the electrode combination and parameters in formulating and delivering the electrical stimulation to patient 12.

According to examples described herein, such stimulation parameters may be adjusted to modify stimulation therapy delivered by IMD 14 based on the detected posture state of patient 12. In some examples, processor 80 may detect a posture state of patient 12 via posture state module 86 that indicates that a modification of the stimulation therapy is appropriate, e.g., according to instructions stored in memory 82. Processor 80 may access instructions for modifying the stimulation therapy based on the patient 12 posture state, e.g., by changing from a stimulation program appropriate for the previous posture state to a stimulation program appropriate for patient's current posture state.

An exemplary range of electrical stimulation parameters likely to be effective in treating chronic pain, e.g., when applied to spinal cord 18, are listed below. While stimulation pulses are described, stimulation signals may be of any of a variety of forms such as sine waves or the like.

1. Pulse Rate: between approximately 0.5 Hz and 1200 Hz, more preferably between approximately 5 Hz and 250 Hz, and still more preferably between approximately 30 Hz and 130 Hz.

2. Amplitude: between approximately 0.1 volts and 50 volts, more preferably between approximately 0.5 volts and 20 volts, and still more preferably between approximately 1 volt and 10 volts. In other embodiments, a current amplitude may be defined as the biological load in the voltage that is delivered. For example, the range of current amplitude may be between 0.1 milliamps (mA) and 50 mA.

3. Pulse Width: between about 10 microseconds and 5000 microseconds, more preferably between approximately 100 microseconds and 1000 microseconds, and still more preferably between approximately 180 microseconds and 450 microseconds.

In other applications, different ranges of parameter values may be used. For deep brain stimulation (DBS), as one example, alleviation or reduction of symptoms associated with Parkinson's disease, essential tremor, epilepsy or other disorders may make use of stimulation having a pulse rate in the range of approximately 0.5 to 1200 Hz, more preferably 5 to 250 Hz, and still more preferably 30 to 185 Hz, and a pulse width in the range of approximately 10 microseconds and 5000 microseconds, more preferably between approximately 60 microseconds and 1000 microseconds, still more preferably between approximately 60 microseconds and 450 microseconds, and even more preferably between approximately 60 microseconds and 150 microseconds. Amplitude ranges such as those described above with reference to SCS, or other amplitude ranges, may be used for different DBS applications.

Processor 80 accesses stimulation parameters in memory 82, e.g., as programs and groups of programs. Upon selection of a particular program group, processor 80 may control stimulation generator 84 to deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate. In addition, each program may specify a particular electrode combination for delivery of stimulation. Again, the electrode combination may specify particular electrodes in a single array or multiple arrays, e.g., on a single lead or among multiple leads. Processor 80 also may control telemetry circuit 88 to send and receive information to and from external programmer 20. For example, telemetry circuit 88 may send information to and receive information from patient programmer 30.

Posture state module 86 allows IMD 14 to sense or detect the current patient posture state, e.g., posture, activity or any other static position or motion of patient 12. In the example of FIG. 4, posture state module 86 may include one or more accelerometers, such as three-axis accelerometers, capable of detecting static orientation or vectors in three-dimensions. The three-axis accelerometer may be a micro-electro-mechanical accelerometer. In other examples, posture state module 86 may alternatively or additionally include one or more gyroscopes, pressure transducers or other sensors to sense the current posture state occupied by patient 12. Posture state information generated by posture state module 86 and processor 80 may correspond to an activity and/or posture undertaken by patient 12 or a gross level of physical activity, e.g., activity counts based on footfalls or the like.

Posture state information from posture state module 86 may be stored in memory 82 for later review by a clinician, used to adjust therapy, present a posture state indication to patient 12, or some combination thereof. As an example, processor 80 may record the posture state parameter value, or output, of the 3-axis accelerometer and assign the posture state parameter value to a certain predefined posture indicated by the posture state parameter value. In this manner, IMD 14 may be able to track how often patient 12 remains within a certain posture state. IMD 14 may also store which group or program was being used to deliver therapy when patient 12 was in the sensed posture. Further, processor 80 may also adjust therapy for a new posture when posture state module 86 indicates that patient 12 has in fact changed postures. Therefore, IMD 14 may be configured to provide posture responsive stimulation therapy to patient 12. Stimulation adjustments in response to posture state may be automatic or semi-automatic (subject to patient approval). In many cases, fully automatic adjustments may be desirable so that IMD 14 may react more quickly to posture state changes.

A posture state parameter value from posture state module 86 that indicates the posture state may constantly vary throughout the day of patient 12. However, a certain activity (e.g., walking, running, or biking) or a posture (e.g., standing, sitting, or lying (front, back, left, right)) may include multiple posture state parameter values from posture state module 86. Memory 82 may include definitions for each posture state of patient 12. In one example, the definitions of each posture state may be illustrated as a cone in three-dimensional space. Whenever the posture state parameter value, e.g., a vector, from the three-axis accelerometer of posture state module 86 resides within a predefined cone or volume, processor 80 indicates that patient 12 is in the posture state of the cone or volume. In other examples, a posture state parameter value from the 3-axis accelerometer may be compared to values in a look-up table or equation to determine the posture state in which patient 12 currently resides.

Posture state-responsive stimulation may allow IMD 14 to implement a certain level of automation in therapy adjustments. Automatically adjusting stimulation may free patient 12 from the constant task of manually adjusting therapy each time patient 12 changes posture or starts and stops a certain posture state. Such manual adjustment of stimulation parameters can be tedious, requiring patient 14 to, for example, depress one or more keys of patient programmer 30 multiple times during the patient posture state to maintain adequate symptom control. In some embodiments, patient 12 may eventually be able to enjoy posture state responsive stimulation therapy without the need to continue making changes for different postures via patient programmer 30. Instead, patient 12 may transition immediately or over time to fully automatic adjustments based on posture state.

Although posture state module 86 is described as containing the 3-axis accelerometer, posture state module 86 may contain multiple single-axis accelerometers, dual-axis accelerometers, 3-axis accelerometers, or some combination thereof. In some examples, an accelerometer or other sensor may be located within or on IMD 14, on one of leads 16 (e.g., at the distal tip or at an intermediate position), an additional sensor lead positioned somewhere within patient 12, within an independent implantable sensor, or even worn on patient 12. For example, one or more microsensors may be implanted within patient 12 to communicate posture state information wirelessly to IMD 14. In this manner, the patient 12 posture state may be determined from multiple activity sensors placed at various locations on or within the body of patient 12.

In some embodiments, processor 80 processes the analog output of the posture state sensor in posture state module 86 to determine activity and/or posture data. For example, where the posture state sensor comprises an accelerometer, processor 80 or a processor of posture state module 86 may process the raw signals provided by the posture state sensor to determine activity counts. In some embodiments, processor 80 may process the signals provided by the posture state sensor to determine velocity of motion information along each axis.

In one example, each of the x, y, and z signals provided by the posture state sensor has both a DC component and an AC component. The DC components describes the gravitational force exerted upon the sensor and can thereby be used to determine orientation of the sensor within the gravitational field of the earth. Assuming the orientation of the sensor is relatively fixed with respect to the patient, the DC components of the x, y and z signals may be utilized to determine the patient's orientation within the gravitational field, and hence to determine the posture of the patient.

The AC component of the x, y and z signals yields information about patient motion. In particular, the AC component of a signal may be used to derive a value for an activity describing the patient's motion. This activity may involve a level, direction of motion, or acceleration of the patient.

One method for determining the activity is an activity count. An activity count may be used to indicate the activity or activity level of patient 12. For example, a signal processor may sum the magnitudes of the AC portion of an accelerometer signal for N consecutive samples. For instance, assuming sampling occurs as 25 Hz, N may be set to 25, so that count logic provides the sum of the samples that are obtained in one second. This sum may be referred to as an "activity count." The number "N" of consecutive samples may be selected by the processor based on the current posture state, if desired. The activity count may be the activity portion of the activity parameter value that is added to the posture portion. The resulting activity parameter value may then incorporate both activity and posture to generate an accurate indication of the motion of patient 12.

As another example, the activity parameter value may be defined as describing a direction of motion. This activity parameter value may be associated with a vector and an associated tolerance, which may be a distance from the vector. Another example of an activity parameter value relates to acceleration. The value quantifying a level of change of motion over time in a particular direction may be associated with this parameter referenced in the activity parameter value.

In other embodiments, posture state module 86 may additionally or alternatively be configured to sense one or more physiological parameters of patient 12. For example, physiological parameters may include heart rate, electromyography (EMG), an electroencephalogram (EEG), an electrocardiogram (ECG), temperature, respiration rate, or pH. These physiological parameters may be used by processor 80, in some embodiments, to confirm or reject changes in sensed posture state that may result from vibration, patient travel (e.g., in an aircraft, car or train), or some other false positive of posture state.

Wireless telemetry in IMD 14 with external programmer 20, e.g., patient programmer 30 or clinician programmer 60, or another device may be accomplished by radio frequency (RF) communication or proximal inductive interaction of IMD 14 with external programmer 20. Telemetry circuit 88 may send information to and receive information from external programmer 20 on a continuous basis, at periodic intervals, at non-periodic intervals, or upon request from the stimulator or programmer. To support RF communication, telemetry circuit 88 may include appropriate electronic components, such as amplifiers, filters, mixers, encoders, decoders, and the like.

When the posture state parameter value indicates that patient 12 has changed to a different posture state, processor 80 may communicate with patient programmer 30 via telemetry circuitry 88 to indicate the newly detected posture state, i.e., a new posture state detection that indicates the current posture state occupied by patient 12. In this manner, processor 80 may force patient programmer 30 to present a different posture state indication based upon the sensed posture state parameter value of the patient posture state. In particular, processor 80 may transmit a new posture state detection to patient programmer 30 to indicate the currently detected posture state occupied by the patient. Alternatively, processor 80 may periodically or non-periodically send posture state information to patient programmer 30 either unilaterally or in response to a request from patient programmer 30. For example, patient programmer 30 may request the posture state parameter value or currently detected posture state, either of which indicates detected posture state, and independently change the posture state indication when it is appropriate to do so.

Power source 90 delivers operating power to the components of IMD 14. Power source 90 may include a small rechargeable or non-rechargeable battery and a power generation circuit to produce the operating power. Recharging may be accomplished through proximal inductive interaction between an external charger and an inductive charging coil within IMD 14. In some embodiments, power requirements may be small enough to allow IMD 14 to utilize patient motion and implement a kinetic energy-scavenging device to trickle charge a rechargeable battery. In other embodiments, traditional batteries may be used for a limited period of time. As a further alternative, an external inductive power supply could transcutaneously power IMD 14 when needed or desired.

Figure 5:
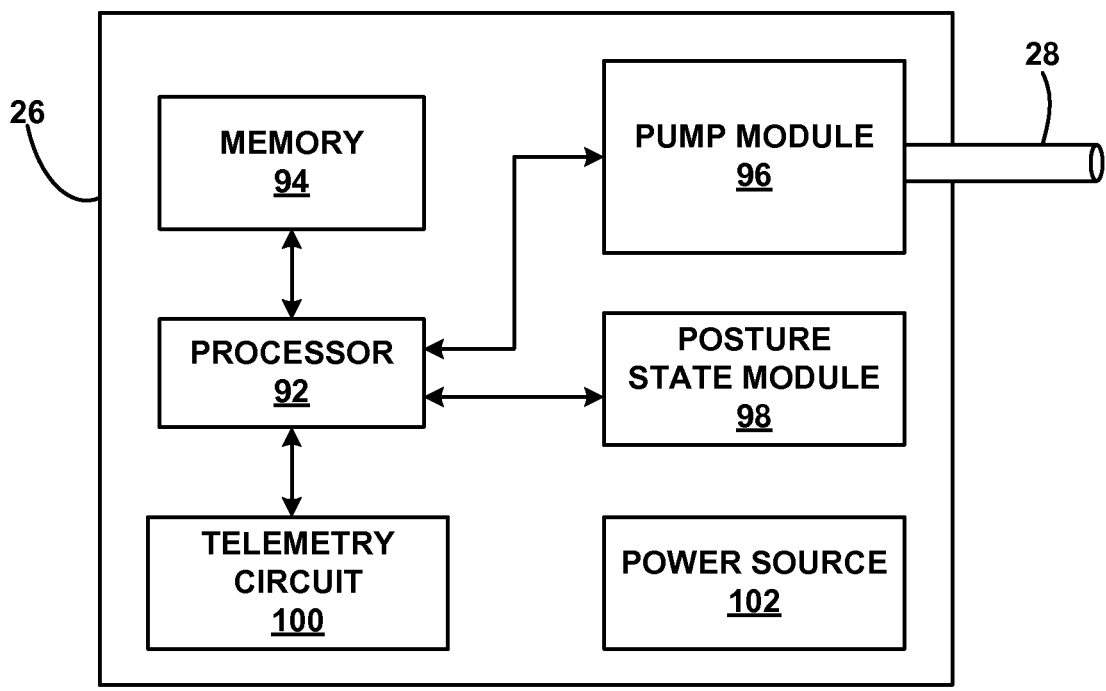
FIG. 5 is a functional block diagram illustrating various components of an implantable drug pump.

FIG. 5 is a functional block diagram illustrating various components of an IMD 26 that is a drug pump. IMD 26 is a drug pump that operates substantially similar to IMD 14 of FIG. 4. IMD 26 includes processor 92, memory 94, pump module 96, posture state module 98, telemetry circuit 100, and power source 102. Instead of stimulation generator 84 of IMD 14, IMD 26 includes pump module 96 for delivering drugs or some other therapeutic agent via catheter 28. Pump module 96 may include a reservoir to hold the drug and a pump mechanism to force drug out of catheter 28 and into patient 12.

Processor 92 may control pump module 96 according to therapy instructions stored within memory 94. For example, memory 94 may contain the programs or groups of programs that define the drug delivery therapy for patient 12. A program may indicate the bolus size or flow rate of the drug, and processor 92 may accordingly deliver therapy. Processor 92 may also use posture state information from posture state module 98 to adjust drug delivery therapy when patient 12 changes posture states, e.g., adjusts their posture.

Figure 6:
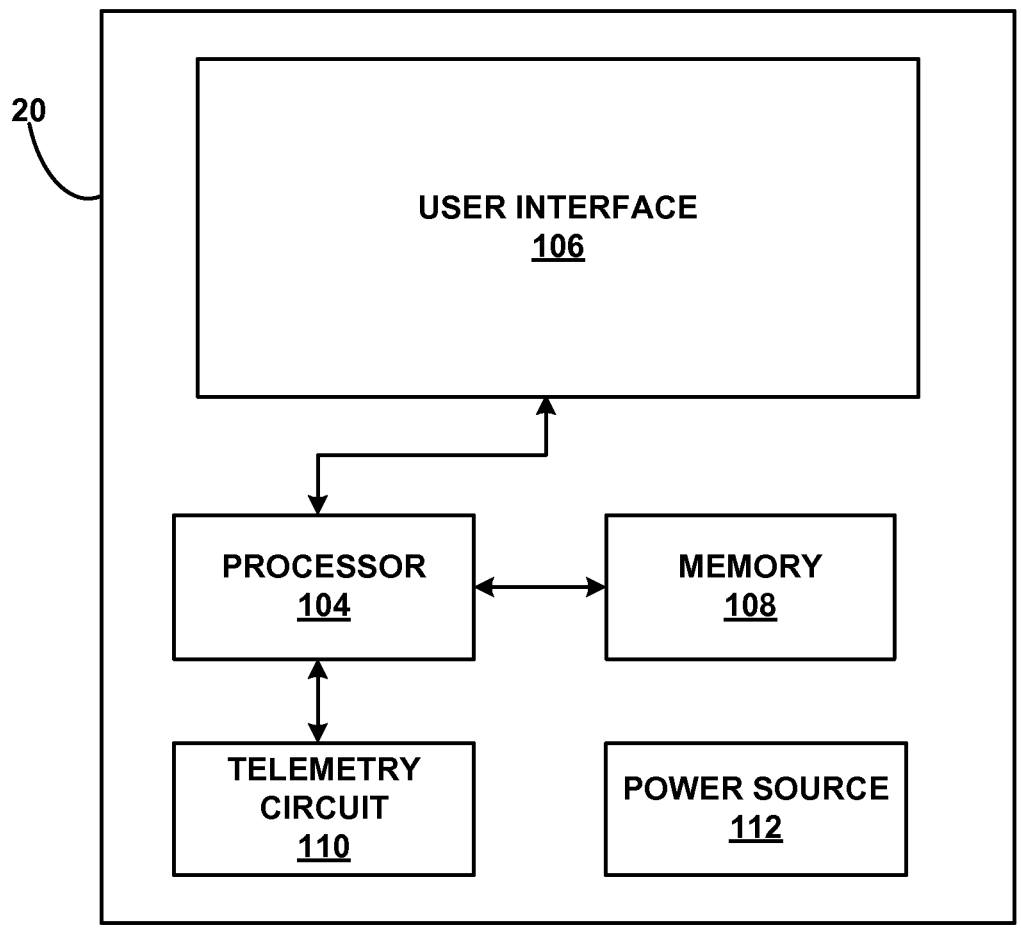
FIG. 6 is a functional block diagram illustrating various components of an external programmer for an implantable medical device.

FIG. 6 is a functional block diagram illustrating various components of an external programmer 20 for IMDs 14 or 26. As shown in FIG. 6, external programmer 20 includes processor 104, memory 108, telemetry circuit 110, user interface 106, and power source 112. External programmer 20 may be embodied as patient programmer 30 or clinician programmer 60. A clinician or patient 12 interacts with user interface 106 in order to manually change the stimulation parameters of a program, change programs within a group, turn posture responsive stimulation ON or OFF, view therapy information, view posture state information, view a posture state indication, or otherwise communicate with IMDs 14 or 26.

User interface 106 may include a screen and one or more input buttons, as in the example of patient programmer 30, that allow external programmer 20 to receive input from a user. Alternatively, user interface 106 may additionally or only utilize a touch screen display, as in the example of clinician programmer 60. The screen may be a liquid crystal display (LCD), dot matrix display, organic light-emitting diode (OLED) display, touch screen, or any other device capable of delivering and/or accepting information. For visible posture state indications, a display screen may suffice. For audible and/or tactile posture state indications, programmer 20 may further include one or more audio speakers, voice synthesizer chips, piezoelectric buzzers, or the like.

Input buttons for user interface 106 may include a touch pad, increase and decrease buttons, emergency shut off button, and other buttons needed to control the stimulation therapy, as described above with regard to patient programmer 30. Processor 104 controls user interface 106, retrieves data from memory 108 and stores data within memory 108. Processor 104 also controls the transmission of data through telemetry circuit 110 to IMDs 14 or 26. Memory 108 includes operation instructions for processor 104 and data related to patient 12 therapy.

Telemetry circuit 110 allows the transfer of data to and from IMD 14, or IMD 26. Telemetry circuit 110 may communicate automatically with IMD 14 at a scheduled time or when the telemetry circuit detects the proximity of the stimulator. Alternatively, telemetry circuit 110 may communicate with IMD 14 when signaled by a user through user interface 106. To support RF communication, telemetry circuit 110 may include appropriate electronic components, such as amplifiers, filters, mixers, encoders, decoders, and the like. Power source 112 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

In some examples, external programmer 20 may be configured to recharge IMD 14 in addition to programming IMD 14. Alternatively, a recharging device may be capable of communication with IMD 14. Then, the recharging device may be able to transfer programming information, data, or any other information described herein to IMD 14. In this manner, the recharging device may be able to act as an intermediary communication device between external programmer 20 and IMD 14. In other cases, the programmer may be integrated with a recharging functionality in the combined programming/recharging device. The techniques described herein may be communicated between IMD 14 via any type of external device capable of communication with IMD 14.

Figure 7:
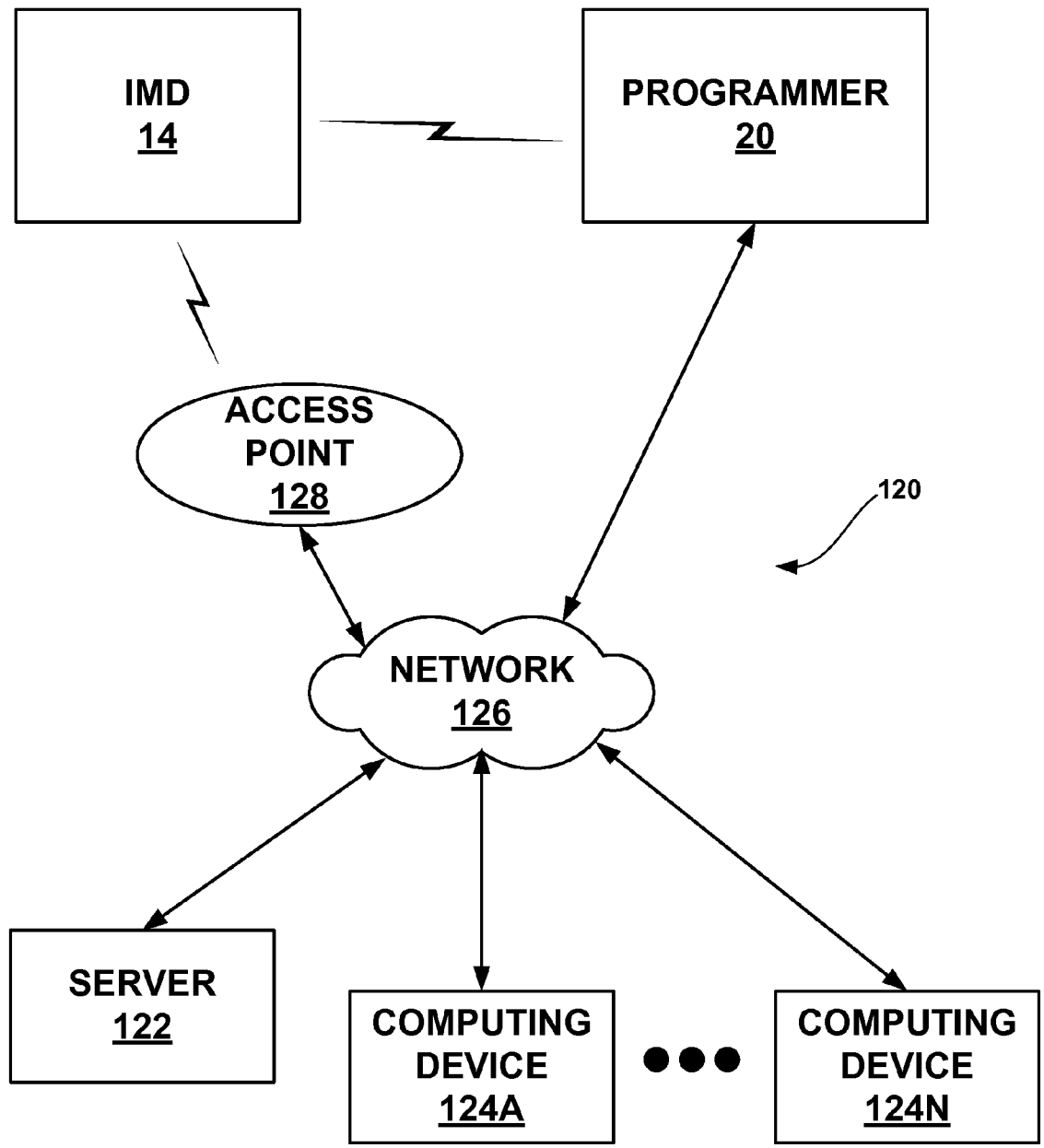
FIG. 7 is a block diagram illustrating an example system that includes an external device, such as a server, and one or more computing devices that are coupled to an implantable medical device and external programmer shown in FIGS. 1A-1C via a network.

FIG. 7 is a block diagram illustrating an example system 120 that includes an external device, such as a server 122, and one or more computing devices 124A-124N, that are coupled to IMD 14 and external programmer 20 shown in FIGS. 1A-1C via a network 126. In this example, IMD 14 may use its telemetry circuit 88 to communicate with external programmer 20 via a first wireless connection, and to communication with an access point 128 via a second wireless connection. In other examples, IMD 26 may also be used in place of IMD 14, and external programmer 20 may be either patient programmer 30 or clinician programmer 60.

In the example of FIG. 7, access point 128, external programmer 20, server 122, and computing devices 124A-124N are interconnected, and able to communicate with each other, through network 126. In some cases, one or more of access point 128, external programmer 20, server 122, and computing devices 124A-124N may be coupled to network 126 through one or more wireless connections. IMD 14, external programmer 20, server 122, and computing devices 124A-124N may each comprise one or more processors, such as one or more microprocessors, digital signal processors (DSPs), application specific integrated circuits (ASICs), field programmable gate arrays (FPGAs), programmable logic circuitry, or the like, that may perform various functions and operations, such as those described in this disclosure.

Access point 128 may comprise a device, such as a home monitoring device, that connects to network 126 via any of a variety of connections, such as telephone dial-up, digital subscriber line (DSL), or cable modem connections. In other embodiments, access point 128 may be coupled to network 126 through different forms of connections, including wired or wireless connections.

During operation, IMD 14 may collect and store various forms of data. For example, IMD 14 may collect sensed posture state information during therapy that indicate how patient 12 moves throughout each day. In some cases, IMD 14 may directly analyze the collected data to evaluate the patient 12 posture state, such as what percentage of time patient 12 was in each identified posture. In other cases, however, IMD 14 may send stored data relating to posture state information to external programmer 20 and/or server 122, either wirelessly or via access point 128 and network 126, for remote processing and analysis.

For example, IMD 14 may sense, process, trend and evaluate the sensed posture state information. This communication may occur in real time, and network 126 may allow a remote clinician to review the current patient posture state by receiving a presentation of a posture state indication on a remote display, e.g., computing device 124A. Alternatively, processing, trending and evaluation functions may be distributed to other devices such as external programmer 20 or server 122, which are coupled to network 126. In addition, posture state information may be archived by any of such devices, e.g., for later retrieval and analysis by a clinician.

In some cases, IMD 14, external programmer 20 or server 122 may process posture state information or raw data and/or therapy information into a displayable posture state report, which may be displayed via external programmer 20 or one of computing devices 124A-124N. The posture state report may contain trend data for evaluation by a clinician, e.g., by visual inspection of graphic data. In some cases, the posture state report may include the number of activities patient 12 conducted, a percentage of time patient 12 was in each posture state, the average time patient 12 was continuously within a posture state, what group or program was being used to deliver therapy during each activity, the number of adjustments to therapy during each respective posture state, or any other information relevant to patient 12 therapy, based on analysis and evaluation performed automatically by IMD 14, external programmer 20 or server 122. A clinician or other trained professional may review and/or annotate the posture state report, and possibly identify any problems or issues with the therapy that should be addressed.

In some cases, server 122 may be configured to provide a secure storage site for archival of posture state information that has been collected from IMD 14 and/or external programmer 20. Network 126 may comprise a local area network, wide area network, or global network, such as the Internet. In other cases, external programmer 20 or server 122 may assemble posture state information in web pages or other documents for viewing by trained professionals, such as clinicians, via viewing terminals associated with computing devices 124A-124N. System 120 may be implemented, in some aspects, with general network technology and functionality similar to that provided by the Medtronic CareLink® Network developed by Medtronic, Inc., of Minneapolis, Minn.

Although some examples of the disclosure may involve posture state information and data, system 120 may be employed to distribute any information relating to the treatment of patient 12 and the operation of any device associated therewith. For example, system 120 may allow therapy errors or device errors to be immediately reported to the clinician. In addition, system 120 may allow the clinician to remotely intervene in the therapy and reprogram IMD 14, patient programmer 30, or communicate with patient 12. In an additional example, the clinician may utilize system 120 to monitor multiple patients and share data with other clinicians in an effort to coordinate rapid evolution of effective treatment of patients. Further, posture state detection may also be used to provide notifications, such as providing notification via a wireless link to a care giver that a patient has potentially experienced a fall.

Furthermore, although the disclosure is described with respect to SCS therapy, such techniques may be applicable to IMDs that convey other therapies in which posture state information is important, such as, e.g., DBS, pelvic floor stimulation, gastric stimulation, occipital stimulation, functional electrical stimulation, and the like. Also, in some aspects, techniques for evaluating posture state information, as described in this disclosure, may be applied to IMDs that are generally dedicated to sensing or monitoring and do not include stimulation or other therapy components. For example, an implantable monitoring device may be implanted in conjunction with an implantable stimulation device, and be configured to evaluate sensing integrity of leads or electrodes associated with the implantable monitoring device based on sensed signals evoked by delivery of stimulation by the implantable stimulation device.

Figure 8A:
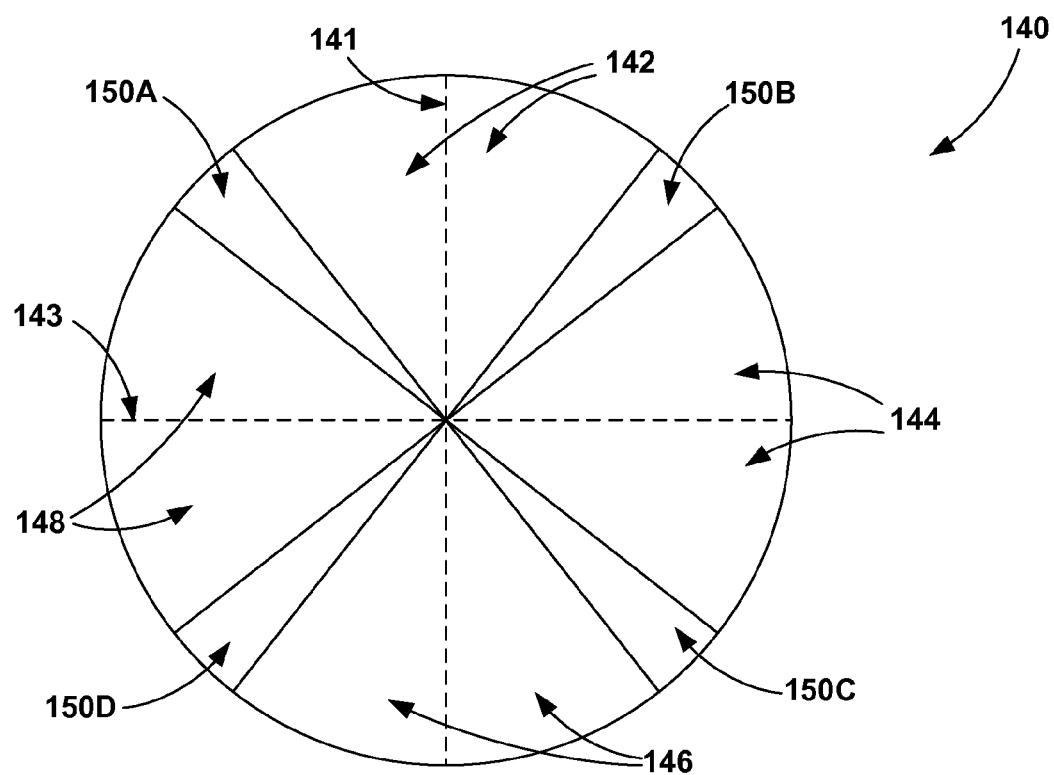
FIGS. 8A-8C are conceptual illustrations of posture cones that may be used to define a posture state of a patient based on signals sensed by a posture state sensor.
Figure 8B:
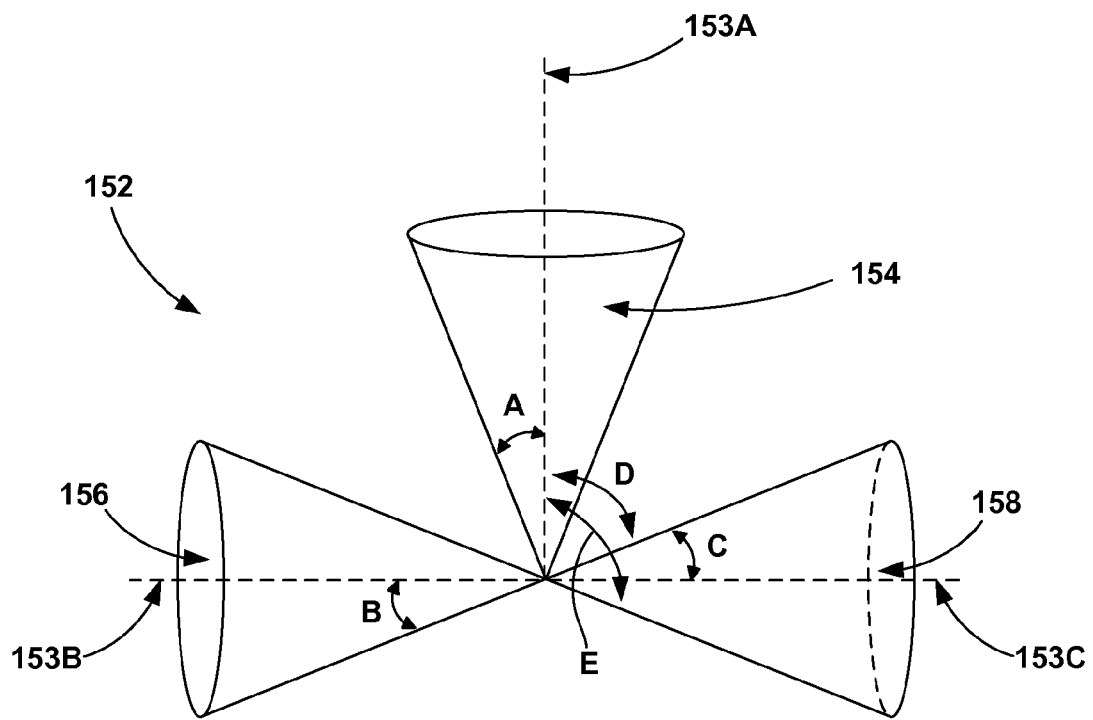
Figure 8C:
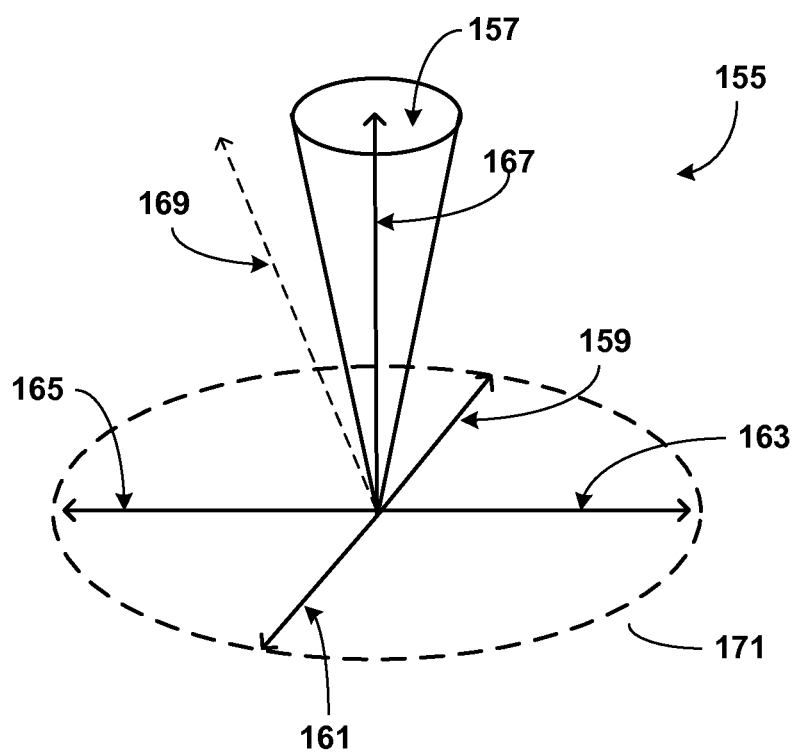

FIGS. 8A-8C are conceptual illustrations of posture state spaces 140, 152, 155 within which posture state reference data may define the posture state of patient 12. Posture state reference data may define certain regions associated with particular posture states of patient 12 within the respective posture state spaces 140, 152, 155. The output of one or more posture state sensors may be analyzed by posture state module 86 with respect to posture state spaces 140, 152, 155 to determine the posture state of patient 12. For example, if the output of one or more posture state sensors is within a particular posture region defined by posture state reference data, posture state module 86 may determine that patient 12 is within the posture state associated with the respective posture state region.

In some cases, one or more posture state regions may be defined as posture state cones. Posture state cones may be used to define a posture state of patient 12 based on the output from a posture state sensor of a posture state according to an example method for posture state detection. A posture state cone may be centered about a posture state reference coordinate vector that corresponds to a particular posture state. In the examples of FIGS. 8A and 8B, the posture state module 86 of IMD 14 or IMD 26 may use a posture state sensor, e.g., a three-axis accelerometer that provides data indicating the posture state of patient 12, to sense posture vectors. While the sensed data may be indicative of any posture state, postures of patient 12 will generally be used below to illustrate the concept of posture cones. As shown in FIG. 8A, posture state space 140 represents a vertical plane dividing patient 12 from left and right sides, or the sagittal plane. A posture state parameter value from two axes of the posture state sensor may be used to determine the current posture state of patient 12 according to the posture state space 140. The posture state data may include x, y and z coordinate values.

A posture cone may be defined by a reference coordinate vector for a given posture state in combination with a distance or angle defining a range of coordinate vectors within a cone surrounding the posture reference coordinate vector. Alternatively, a posture cone may be defined by a reference coordinate vector and a range of cosine values computed using the reference coordinate vector as an adjacent vector and any of the outermost vectors of the cone as a hypotenuse vector. If a sensed posture state vector is within an applicable angle or distance of the reference coordinate vector, or if the sensed posture state vector and the reference coordinate vector produce a cosine value in a specified cosine range, then posture state vector is determined to reside within the posture cone defined by the reference coordinate vector.

Posture state space 140 is segmented into different posture cones that are indicative of a certain posture state of patient 12. In the example of FIG. 8A, upright cone 142 indicates that patient 12 is sitting or standing upright, lying back cone 148 indicates that patient 12 is lying back down, lying front cone 144 indicates that patient 12 is lying chest down, and inverted cone 146 indicates that patient 12 is in an inverted position. Other cones may be provided, e.g., to indicate that patient 12 is lying on the right side or left side. For example, a lying right posture cone and a lying left posture cone may be positioned outside of the sagittal plane illustrated in FIG. 8A. In particular, the lying right and lying left posture cones may be positioned in a coronal plane substantially perpendicular to the sagittal plane illustrated in FIG. 8A. For ease of illustration, lying right and lying left cones are not shown in FIG. 8A.

Vertical axis 141 and horizontal axis 143 are provided for orientation of posture state area 140, and are shown as orthogonal for purposes of illustration. However, posture cones may have respective posture reference coordinate vectors that are not orthogonal in some cases. For example, individual reference coordinate vectors for cones 142 and 146 may not share the same axis, and reference coordinate vectors for cones 144 and 148 may not share the same axis. Also, reference coordinate vectors for cones 144 and 148 may or may not be orthogonal to reference coordinates vectors for cones 142, 146. Moreover, the reference coordinate vectors need not reside in the same plane. Therefore, although orthogonal axes are shown in FIG. 8A for purposes of illustration, respective posture cones may be defined by individualized reference coordinate vectors for the cones.

IMD 14 may monitor the posture state parameter value of the posture state sensor to produce a sensed coordinate vector and identify the current posture of patient 12 by identifying which cone the sensed coordinated vector of the posture state sensor module 86 resides. For example, if the posture state parameter value corresponds to a sensed coordinate vector that falls within lying front cone 144, IMD 14 determines that patient 12 is lying down on their chest. IMD 14 may store this posture information as a determined posture state or as raw output from the posture state sensor, change therapy according to the posture, or both. Additionally, IMD 14 may communicate the posture information to patient programmer 30 so that the patient programmer can present a posture state indication to patient 12.

In addition, posture state area 140 may include hysteresis zones 150A, 150B, 150C, and 150D (collectively "hysteresis zones 150"). Hysteresis zones 150 are positions within posture state area 140 where no posture cones have been defined. Hysteresis zones 150 may be particularly useful when IMD 14 utilizes the posture state information and posture cones to adjust therapy automatically. If the posture state sensor indicates that patient 12 is in upright cone 142, IMD 14 would not detect that patient 12 has entered a new posture cone until the posture state parameter value indicates a different posture cone. For example, if IMD 14 determines that patient 12 moves to within hysteresis zone 150A from upright cone 142, IMD 14 retains the posture as upright. In this manner, IMD 14 does not change the corresponding therapy until patient 12 fully enters a different posture cone. Hysteresis zones 150 prevent IMD 14 from continually oscillating between different therapies when patient 12's posture state resides near a posture cone boundary.

Each posture cone 142, 144, 146, 148 may be defined by an angle in relation to a reference coordinate vector defined for the respective posture cone. Alternatively, some posture cones may be defined by an angle relative to a reference coordinate vector for another posture cone. For example, lying postures may be defined by an angle with respect to a reference coordinate vector for an upright posture cone. In each case, as described in further detail below, each posture cone may be defined by an angle in relation to a reference coordinate posture vector defined for a particular posture state. The reference coordinate vector may be defined based on posture sensor data generated by a posture state sensor while patient 12 occupies a particular posture state desired to be defined using the reference coordinate vector. For example, a patient may be asked to occupy a posture so that a reference coordinate vector can be sensed for the respective posture. In this manner, vertical axis 141 may be specified according to the patient's actual orientation. Then, a posture cone can be defined using the reference coordinate vector as the center of the cone.

Vertical axis 141 in FIG. 8A may correspond to a reference coordinate vector sensed while the patient was occupying an upright posture state. Similarly, a horizontal axis 143 may correspond to a reference coordinate vector sensed while the patient is occupying a lying posture state. A posture cone may be defined with respect to the reference coordinate vector. Although a single axis is shown extending through the upright and inverted cones 142, 146, and another single axis is shown extending through the lying down and lying up cones 144, 148, individual reference coordinate vectors may be used for respective cones, and the reference coordinate vectors may not share the same axes, depending on differences between the reference coordinate vectors obtained for the posture cones.

Posture cones may be defined by the same angle or different angles, symmetrical to either axis, or asymmetrical to either axis. For example, upright cone 142 may have an angle of eighty degrees, +40 degrees to −40 degrees from the positive vertical axis 141. In some cases, lying cones may be defined relative to the reference coordinate vector of the upright cone 142. For example, lying up cone 148 may have an angle of eighty degrees, −50 degrees to −130 degrees from the positive vertical axis 141. Inverted cone 146 may have an angle of eighty degrees, −140 degrees to +140 degrees from vertical axis 141. In addition, lying down cone 144 may have an angle of eighty degrees, +50 degrees to +130 degrees from the positive vertical axis 141. In other examples, each posture cone may have varying angle definitions, and the angles may change during therapy delivery to achieve the most effective therapy for patient 12.

Alternatively or additionally, instead of an angle, posture cones 144, 146, 148, 148 may be defined by a cosine value or range of cosine values in relation to vertical axis 141, horizontal axis 143, or some other axis, such as, e.g., individual reference coordinate vectors for the respective cones. For example, a posture cone may be defined by a cosine value that defines the minimum cosine value, calculated using a reference coordinate vector and a respective coordinate vector sensed by a posture state sensor at any point in time. In the cosine computation, the value (adjacent/hypotenuse) can be computed using the magnitude of the coordinate reference vector as the adjacent and a vector at the outermost extent of the cone as the hypotenuse to define a range of cosine values consistent with the outer bound of the cone.

For upright cone 142, the cosine range may extend from the maximum cosine value of 1.0, corresponding to a sensed vector that matches the reference coordinate vector of the upright cone, to a minimum cosine value that corresponds to a sensed vector at the outer limit of the upright cone. As another example, for lying cone 144, the cosine range may extend from the maximum cosine value of 1.0, corresponding to a sensed vector that matches the reference coordinate vector of the lying cone, to a minimum cosine value that corresponds to a sensed vector at the outer limit of the lying cone. Alternatively, the lying cone 144 may be defined with reference to the upright cone 142, such that the cosine range may extend between a maximum and minimum values determined relative to the reference coordinate vector for the upright cone.

In other examples, posture state area 140 may include additional posture cones than those shown in FIG. 8A. For example, a reclining cone may be located between upright cone 142 and lying back cone 148 to indicate when patient 12 is reclining back (e.g., in a dorsal direction). In this position, patient 12 may need a different therapy to effectively treat symptoms. Different therapy programs may provide efficacious therapy to patient 12 when patient 12 is in each of an upright posture (e.g., within upright cone 142), lying back posture (e.g., within lying back cone 148), and a reclining back posture. Thus, a posture cone that defines the reclining back posture may be useful for providing efficacious posture-responsive therapy to patient 12. In other examples, posture state area 140 may include fewer posture cones than cones 142, 144, 146, 148 shown in FIG. 8A. For example, inverted cone 146 may be replaced by a larger lying back cone 148 and lying front cone 144.

FIG. 8B illustrates an example posture state space 152 that is a three-dimensional space in which the posture state parameter value from the posture state sensor is placed in relation to the posture cones. Posture state space 152 is substantially similar to posture state area 140 of FIG. 8A. However, the posture state parameter value derived from all three axes of a 3-axis accelerometer may be used to accurately determine the posture state of patient 12. In the example of FIG. 8B, posture state space 152 includes upright cone 154, lying back cone 156, and lying front cone 158. Posture state space 152 also includes hysteresis zones (not shown) similar to those of posture state area 140. In the example of FIG. 8B, the hysteresis zones are the spaces not occupied by a posture cone, e.g., upright cone 154, lying back cone 156, and lying front cone 158.

Posture cones 154, 156 and 158 also are defined by a respective center line 153A, 153B, or 153C, and associated cone angle A, B or C. For example, upright cone 154 is defined by center line 153A that runs through the center of upright cone 154. Center line 153A may correspond to an axis of the posture state sensor or some other calibrated vector. In some embodiments, each center line 153A, 153B, 153C may correspond to a posture reference coordinate vectors defined for the respective postures, e.g., the upright posture. For instance, assuming that patient 12 is standing, the DC portion of the x, y, and z signals detected by the posture state sensor of posture state module 86 define a posture vector that corresponds to center line 153A.

The x, y, and z signals may be measured while patient 12 is known to be in a specified position, e.g., standing, and the measured vector may be correlated with the upright posture state. Thereafter, when the DC portions of the posture state sensor signal are within some predetermined cone tolerance or proximity, e.g., as defined by an angle, distance or cosine value, of the posture reference coordinate vector (i.e., center line 153A), it may be determined that patient 12 is in the upright posture. In this manner, a sensed posture coordinate vector may be initially measured based on the output of one or more posture state sensors of posture state module 86, associated with a posture state, such as upright, as a reference coordinate vector, and then later used to detect a patient's posture state.

As previously indicated, it may be desirable to allow some tolerance to be associated with a defined posture state, thereby defining a posture cone or other volume. For instance, in regard to the upright posture state, it may be desirable to determine that a patient who is upright but leaning slightly is still in the same upright posture state. Thus, the definition of a posture state may generally include not only a posture reference coordinate vector (e.g., center line 153A), but also a specified tolerance. One way to specify a tolerance is by providing an angle, such as cone angle A, relative to coordinate reference vector 153A, which results in posture cone 154 as described herein. Cone angle A is the deflection angle, or radius, of upright cone 154. The total angle that each posture cone spans is double the cone angle. The cone angles A, B, and C may be generally between approximately 1 degree and approximately 70 degrees. In other examples, cone angles A, B, and C may be between approximately 10 degrees and 30 degrees. In the example of FIG. 8B, cone angles A, B, and C are approximately 20 degrees. Cone angles A, B, and C may be different, and center lines 153A, 153B, and 153C may not be orthogonal to each other.

In some examples, a tolerance may be specified by a cosine value or range of cosine values. The use of cosine values, in some cases, may provide substantial processing efficiencies. As described above, for example, a minimum cosine value, determined using the reference coordinate vector as adjacent and sensed coordinate vector as hypotenuse, indicates the range of vectors inside the cone. If a sensed coordinate vector, in conjunction with the reference coordinate vector for a posture cone, produces a cosine value that is less than the minimum cosine value for the posture cone, the sensed coordinate vector does not reside within the pertinent posture cone. In this manner, the minimum cosine value may define the outer bound of a range of cosine values within a particular posture cone defined in part by a reference coordinate vector.

While center lines 153A, 153B, 153C of each of the posture cones 154, 156, 158, respectively, are shown in FIG. 8B as being substantially orthogonal to each other, in other examples, center lines 153A, 153B, and 153C may not be orthogonal to each other, and need not even reside within the same plane. Again, the relative orientation of center lines 153A, 153B, 153C may depend on the actual reference coordinate vector output of the posture state sensor of posture state module 86 of IMD 14 when patient 12 occupies the respective postures.

In some cases, all of the posture cones may be individually defined based on actual reference coordinate vectors. Alternatively, in some cases, some posture cones may be defined with reference to one or more reference coordinate vectors for one or more other posture cones. For example, lying reference coordinate vectors could be assumed to be orthogonal to an upright reference coordinate vector. Alternatively, lying reference coordinate vectors could be individually determined based on sensed coordinate vectors when the patient is in respective lying postures. Hence, the actual reference coordinate vectors for different postures may be orthogonal or non-orthogonal with respect to one another, and need not reside within a same plane.

In addition to upright cone 154, lying back cone 156, and lying front cone 158, posture state space 152 may include additional posture cones. For example, a lying right cone may be provided to define a patient posture in which patient 12 is lying on his right side and a lying left cone may be provided to define a patient posture in which patient 12 is lying on his left side. In some cases, the lying right cone and lying left cone may be positioned approximately orthogonal to upright cones 154, in approximately the same plane as lying back cone 156 and lying front cone 158. Moreover, posture state space 152 may include an inverted cone positioned approximately opposite of upright cone 154. Such a cone indicates that the patient's posture is inverted from the upright posture, i.e., upside down.

In some examples, to detect the posture state of a patient, posture state module 86 of IMD 14 may determine a sensed coordinate vector based on the posture sensor data generated by one or more posture state sensors, and then analyze the sensed coordinate vector with respect to posture cones 154, 156, 158 of FIG. 8B. For example, in a case in which a posture cone is defined by a reference coordinate vector and a tolerance angle, e.g., tolerance angle "A," posture state module 86 may determine whether the sensed coordinate vector is within upright posture cone 154 by calculating the angle between the sensed coordinate vector and reference coordinate vector, and then determine whether the angle is less than the tolerance angle "A." If so, posture state module 86 determines that the sensed coordinate vector is within upright posture cone 154 and detects that patient 12 is in the upright posture. If posture state module 86 determines that sensed coordinate vector is not within upright posture cone 154, posture state module 86 detects that patient 12 is not in the upright posture.

Posture state module 86 may analyze the sensed coordinate vector in posture state space 152 with respect to each individual defined posture cone, such as posture cones 156 and 158, in such a manner to determine the posture state of patient 12. For example, posture state module 86 may determine the angle between the sensed coordinate vector and reference coordinate vector of individual posture cones defined for the posture state, and compare the determined angle to the tolerance angle defined for the respective posture cone. In this manner, a sensed coordinate vector may be evaluated against each posture cone until a match is detected, i.e., until the sensed coordinate vector is found to reside in one of the posture cones. Hence, a cone-by-cone analysis is one option for posture detection.

In other examples, different posture detection analysis techniques may be applied. For example, instead of testing a sensed coordinate vector against posture cones on a cone-by-cone basis, a phased approach may be applied where the sensed coordinate vector is classified as either upright or not upright. In this case, if the sensed coordinate vector is not in the upright cone, posture state module 86 may determine whether the sensed coordinate vector is in a lying posture, either by testing the sensed coordinate vector against individual lying posture cones or testing the sensed coordinate vector against a generalized lying posture volume, such as a donut- or toroid-like volume that includes all of the lying postures, and may be defined using an angle or cosine range relative to the upright vector, or relative to a modified or virtual upright vector as will be described. In some cases, if lying postures are defined by cones, the lying volume could be defined as a logical OR of the donut- or toroid-like volume and the volumes of the lying posture cones. If the cones are larger such that some portions extend beyond the lying volume, then those portions can be added to the lying volume using the logical OR-like operation.

If the sensed coordinate vector resides within the donut- or toroid-like lying volume, then the sensed coordinate vector may be tested against each of a plurality of lying posture cones in the lying volume. Alternatively, the posture detection technique may not use lying cones. Instead, a posture detection technique may rely on a proximity test between the sensed coordinate vector and each of the reference coordinate vectors for the respective lying postures. The proximity test may rely on angle, cosine value or distance to determine which of the lying posture reference coordinate vectors is closest to the sensed coordinate vector. For example, the reference coordinate vector that produces the largest cosine value with the sensed coordinate vector as hypotenuse and the reference coordinate vector as adjacent is the closest reference coordinate vector. In this case, the lying posture associated with the reference coordinate vector producing the largest cosine value is the detected posture. Hence, there are a variety of ways to detect posture, such as using posture cones, using an upright posture cone with lying volume and lying posture cone test, or using an upright posture cone with lying volume and lying vector proximity test.

As a further illustration of an example posture detection technique, posture state module 86 may first determine whether patient 12 is generally in a lying posture state or upright posture state by analyzing the sensed coordinate vector in posture state space 152 with respect to an axis 153A for the upright posture state. Axis 153A may correspond to the upright reference coordinate vector. For example, angle "A" may be used to define upright posture cone 154, as described above, and angles "D" and "E" may be used to define the vector space in which patient 12 may be generally considered to be in the lying posture state, regardless of the particular posture state cone, e.g., lying front cone 158, lying back cone 156, lying right cone (not shown), or lying left cone (not shown), in which the sensed coordinate vector falls.

If it is determined that a sensed coordinate vector is not within an angle A of the axis 153A, then it may be determined that the patient is not in the upright posture indicated by the upright posture cone. In this case, it may next be determined whether a sensed coordinated vector is generally in a lying posture space volume, which may be considered somewhat donut- or toroid-like, and may be defined relative to the upright reference coordinate vector 153A. As shown, angles "D" and "E" define the minimum and maximum angle values, respectively, that a sensed vector may form with respect to axis 153A of patient 12 for a determination to be made that the patient is generally in the lying posture state. Again, cosine values may be used instead of angles to determine the positions of sensed coordinate vectors relative to posture cones or other posture volumes, or relative to reference coordinate vectors.

As illustrated, angles "D" and "E" may be defined with respect to vertical axis 153A (which may correspond to an upright reference coordinate vector), which is the reference coordinate vector for the upright posture cone, rather than with respect to a reference coordinate vector of a lying posture state cone. If a sensed vector is within the angular range of D to E, relative to axis 153A, then it can be determined by posture state module 86 that the patient is generally in a lying posture. Alternatively, in some examples, an angle C could be defined according to a generally horizontal axis 153C (which may correspond to one of the lying reference coordinate vectors). In this case, if a sensed vector is within angle C of axis 153C, it can be determined by posture state module 86 that the patient is in a lying posture. In each case, the region generally defining the lying posture state may be referred to as a posture donut or posture toroid, rather than a posture cone. The posture donut may generally encompass a range of vectors that are considered to be representative of various lying down postures.

As an alternative, posture state module 86 may rely on cosine values or a range of cosine values to define the posture donut or toroid with respect to axis 153A. When the sensed vector falls within the vector space defined by axis 153A and angles "D" and "E", or produces a cosine value with the reference coordinate vector 153A in a prescribed range, posture state module 86 may determine that patient 12 is generally in a lying posture state. For example, if the sensed vector and reference coordinate vector 153 produce a cosine value in a first range, the posture is upright. If the cosine value is in a second range, the posture is lying. If the cosine value is outside of the first and second ranges, the posture may be indeterminate. The first range may correspond to the range of cosine values that would be produced by vectors in posture cone 154 defined by angle A, and the second range may be correspond to cosine values that would be produced by vectors in the posture donut defined by angles D and E.

When the sensed vector fall within the vector space defined by axis 153A and angles "D" and "E", as indicated by angle or cosine value, posture state module 86 may then determine the particular lying posture state occupied by patient 12, e.g., lying front, lying back, lying right, or lying left. To determine the particular lying posture state occupied by patient 12, posture state module 86 may analyze the sensed vector with respect to reference coordinate vectors for individual lying posture state cones, e.g., lying front cone 156, lying back cone 158, lying right cone (not shown), and lying left cone (not shown), using one more techniques previously described, such as angle or cosine techniques. For example, posture state module 86 may determine whether the sensed coordinated vector resides within one of the lying posture state cones and, if so, select the posture state corresponding to that cone as the detected posture state.

FIG. 8C illustrates an example posture state space 155 that is a three-dimensional space substantially similar to posture state space 152 of FIG. 8B. Posture state space 155 includes upright posture cone 157 defined by reference coordinate vector 167. The tolerance that defines upright posture cone 157 with respect to reference coordinate vector 167 may include a tolerance angle or cosine value, as described above. In contrast to determining whether a sensed coordinate vector resides in a lying cone, FIG. 8C illustrates a method for detecting a lying posture based on proximity of a sensed coordinate vector to one of the reference coordinate vectors for the lying postures.

As shown in FIG. 8C, posture state space 155 includes four reference coordinate vectors 159, 161, 163, 165, which are associated with lying left, lying right, lying front, and lying back posture states, respectively. Posture state module 86 may have defined each of the four reference coordinated vector 159, 161, 163, 165 based on the output of one or more posture sensors while patient 12 occupied each of the corresponding posture states. Unlike lying front and lying back posture cones 158, 156 in the example of FIG. 8B, the posture state reference data for the four defined posture states corresponding to reference vectors 159, 161, 163, 165 need not include angles defined relative to the respective reference vector in a manner that defines a posture cone. Rather, as will be described below, the respective posture state reference vectors may be analyzed with respect to one another in terms of cosine values to determine which particular reference coordinate vector is nearest in proximity to a sensed coordinate vector.

In some examples, to determine the posture state of patient 12, posture state module 85 may determine whether a sensed coordinate vector is within upright posture cone 157 by analyzing the sensed coordinate vector in view of the tolerance angle or cosine value(s) defined with respect to upright posture reference coordinate vector 167, or whether the sensed vector is within a posture donut or toroid defined by a range of angles (as in FIG. 8B) or cosine values with respect to upright posture reference coordinate vector 167, in which case posture state module 86 may determine that patient 12 is in a general lying posture state.

If posture state module 86 determines that patient 12 is occupying a general lying posture state, posture state module 86 may then calculate the cosine value of the sensed coordinate vector with respect to each lying reference coordinate vectors 159, 161, 163, 165. In such a case, posture state module 86 determines the particular lying posture state of patient 12, i.e., lying left, lying right, lying front, lying back, based on which cosine value is the greatest of the four cosine values. For example, if the cosine value calculated with the sensed vector as the hypotenuse and the lying front reference vector 163 as the adjacent vector is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

In some examples, posture state module 86 may determine whether patient 12 is generally in a lying posture state based on the relationship of a sensed vector to upright reference vector 167. For example, as described above, a lying posture donut or toroid may be defined with respect to upright posture reference vector 167, e.g., using angles D and E as in FIG. 8B. Such a technique may be appropriate when lying posture reference vectors 159, 161, 163, 165 define a common plane substantially orthogonal to upright posture reference vector 167. However, the lying posture reference vectors 159, 161, 163, 165 may not in fact be orthogonal to the upright reference coordinate vector 167. Also, the lying posture reference vectors 159, 161, 163, 165 may not reside in the same plane.

To account for non-orthogonal reference vectors, in other examples, a lying posture donut or toroid may be defined with respect to a modified or virtual upright reference vector 169 rather than that actual upright posture reference vector 167. Again, such a technique may be used in situations in which the lying reference vectors 159, 161, 163, 165 are not in a common plane, or the common plane of reference vector 159, 161, 163, 165 is not substantially orthogonal to upright reference vector 167. However, use of the example technique is not limited to such situations.

To define virtual upright reference vector 169, posture state module 86 may compute the cross-products of various combinations of lying reference vectors 159, 161, 163, 165 and average the cross product values. In the example of FIG. 8C, posture state module 86 may compute four cross products and average the four cross product vectors to yield the virtual upright vector. The cross product operations that may be performed are: lying left vector 159 x lying back vector 165, lying back vector 165 x lying right vector 161, lying right vector 161 x lying front vector 163, and lying front vector 163 x lying left vector 159. Each cross product yields a vector that is orthogonal to the two lying reference vectors that were crossed. Averaging each of the cross product vectors yields a virtual upright reference vector that is orthogonal to lying plane 171 approximately formed by lying reference vectors 159, 161, 163, 165.

Using virtual upright reference vector 169, posture state module 86 may define a lying posture donut or toroid in a manner similar to that described with respect to upright reference vector 167, but instead with respect to virtual upright reference vector 169. In particular, when posture state module 86 determines that the patient is not in the upright posture, the posture state module determines whether the patient is in a lying posture based on an angle or cosine value with respect to the virtual upright reference vector 169.

Posture state module 86 may still determine whether patient 12 is in an upright posture state using upright posture cone 157. If posture state module 86 determines that patient 12 is occupying a general lying posture state based on the analysis of the sensed coordinate vector with respect to virtual upright reference vector 169, posture state module 86 may then calculate the cosine value of the sensed coordinate vector (as hypotenuse) with respect to each lying reference coordinate vectors 159, 161, 163, 165 (as adjacent).

In such a case, posture state module 86 determines the particular lying posture state of patient 12, i.e., lying left, lying right, lying front, lying back, based on which cosine value is the greatest of the four cosine values. For example, if the cosine value calculated with the lying front reference vector 163 is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

Additionally, posture state definitions are not limited to posture cones. For example, a definition of a posture state may involve a posture vector and a tolerance, such as a maximum distance from the posture vector. So long as a detected posture vector is within this maximum distance from the posture vector that is included in the definition of the posture state, patient 12 may be classified as being in that posture state. This alternative method may allow posture states to be detected without calculating angles, as is exemplified above in the discussion related to posture cones.

Further to the foregoing, posture states may be defined that are specific to a particular patient's activities and/or profession. For instance, a bank teller may spend a significant portion of his working day leaning forward at a particular angle. A patient-specific "Leaning Forward" posture state including this angle may be defined. The cone angle or other tolerance value selected for this posture state may be specific to the particular posture state definition for this patient. In this manner, the defined posture states may be tailored to a specific user, and need not be "hard-coded" in the IMD.

In some examples, individual posture states may be linked together, thereby tying posture states to a common set of posture reference data and a common set of therapy parameter values. This may, in effect, merge multiple posture cones for purposes of posture state-based selection of therapy parameter values. For example, all lying posture state cones (back, front, left, right) could be treated as one cone or a donut/toroid, e.g., using a technique the same as or similar to that described with respect to FIGS. 8B and 8C to define a donut, toroid or other volume. One program group or common set of therapy parameter values may apply to all posture states in the same merged cone, according to the linking status of the posture states, as directed via external programmer 20.

Merging posture cones or otherwise linking a plurality of posture states together may be useful for examples in which a common set of therapy parameter values provides efficacious therapy to patient 12 for the plurality of posture states. In such an example, linking a plurality of posture states together may help decrease the power consumption required to provide posture-responsive therapy to patient 12 because the computation required to track patient posture states and provide responsive therapy adjustments may be minimized when a plurality of posture states are linked together.

Linking of posture states also may permit a therapy parameter value adjustment in one posture state to be associated with multiple posture states at the same time. For example, the same amplitude level for one or more programs may be applied to all of the posture states in a linked set of posture states. Alternatively, the lying down posture states may all reside within a "donut" or toroid that would be used instead of separate comes 156 and 158, for example. The toroid may be divided into sectional segments that each correspond to different posture states, such as lying (back), lying (front), lying (right), lying (left) instead of individual cones. In this case, different posture reference data and therapy parameter values may be assigned to the different sectional segments of the toroid.

Figure 9:
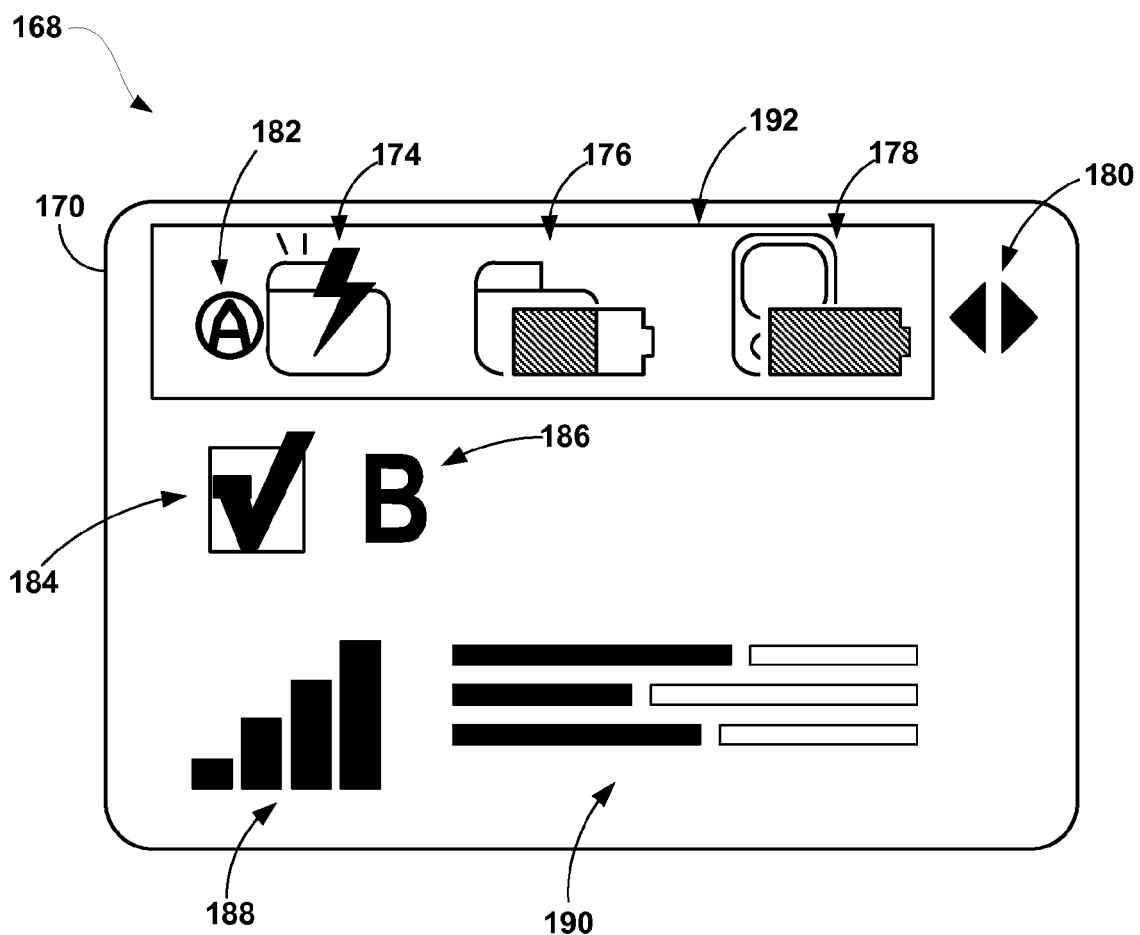
FIG. 9 is a conceptual diagram illustrating an example user interface of a patient programmer for delivering therapy information to the patient.

FIG. 9 is a conceptual diagram illustrating an example user interface 168 of a patient programmer 30 for delivering therapy and posture state information to patient 12. In other examples, a user interface similar to user interface 168 may also be shown on clinician programmer 60. In the example of FIG. 9, display 36 of patient programmer 30 provides user interface 168 to the user, such as patient 12, via screen 170. Screen 170 includes stimulation icon 174, IMD battery icon 176, programmer battery icon 178, navigation arrows 180, automatic posture response icon 182, group selection icon 184, group identifier 186, program identifier 188, amplitude graph 190, and selection box 192. User interface 168 provides information to patient 12 regarding group, program, amplitude, and automatic posture response status. User interface 168 may be configurable, such that more or less information may be provided to patient 12, as desired by the clinician or patient 12.

Selection box 192 allows patient 12 to navigate to other screens, groups, or programs using navigation arrows 180 to manage the therapy. In the example, of screen 170, selection box 192 is positioned so that patient 12 may use arrows 44 and 48 to move to the automatic posture response screen, the volume screen, the contrast or illumination screen, the time screen, and the measurement unit screen of patient programmer 30. In these screens, patient 12 may be able to control the use of the automatic posture response feature and adjust the patient programmer 30 features. Patient 12 may only adjust the features surrounded by selection box 192.

Group identifier 186 indicates one of possibly several groups of programs that can be selected for delivery to patient 12. Group selection icon 184 indicates whether the displayed group, e.g., group B in FIG. 9, is actually selected for delivery to patient 12. If a presently displayed group is selected, group selection icon 184 includes a box with a checkmark. If a presently displayed group is not selected, group selection icon 184 includes a box without a checkmark. To navigate through the program groups, a user may use control pad 40 to move selection box 192 to select the group identifier 186 and then use control pad 40 to scroll through the various groups, e.g., A, B, C, and so forth. IMD 14 may be programmed to support a small number of groups or a large number of groups, where each group contains a small number of programs or a large number of programs that are delivered simultaneously, in sequence, or on a time-interleaved basis.

For each group, group selection icon 184 indicates the appropriate status. For a given group, program identifier 188 indicates one of the programs associated with the group. In the example of FIG. 9, no program number is indicated in program identifier 188 because all of the programs' amplitudes are shown in each bar of amplitude graph 190. Solid portions of the bars indicate the relative amplitude IMD 14 currently is using to deliver stimulation therapy to patient 12, while open portions of the bars indicate the remaining amplitude available to each program. In some embodiments, numerical values of each program's amplitude may be show in addition to or in place of amplitude graph 190. In other embodiments of user interface 168 specific to drug delivery using IMD 26, amplitude graph 190 may show the flow rate of drugs or frequency of bolus delivery to patient 12. This information may be shown in numerical format as well. Patient 12 may encompass group selection icon 184 with selection box 192 to scroll between the different programs of the selected group.

Programmer 30 may be used to define posture state-responsive therapy delivered to a patient based on a sensed posture state of the patient. However, some therapy programs or program groups may not be configured or activated to support posture state-responsive therapy. Automatic posture response icon 182 indicates that IMD 14 is generally activated to automatically change therapy to patient 12 based upon the posture state detected by posture state module 86, i.e., to deliver posture state-responsive therapy in which one or more stimulation parameters are adjusted according to posture state of the patient. In particular, automatic posture responsive therapy may involve adjusting one or more therapy parameter values, selecting different programs or selecting different program groups based on the detected posture state of the patient. However, automatic posture response icon 182 is not present next to group identifier 186. Therefore, group "B" does not have automatic posture responsive therapy activated for any of the programs within group "B." Instead, group "B" may include programs that are not posture state-responsive. Rather, parameters associated with programs of group "B" may be generally static such that they are not adjusted based on detected posture state.

Some groups or individual programs in groups may support automatic posture responsive therapy, while others may not. For example, automatic adjustment of one or more therapy parameters in response to posture state detection may be selectively activated or deactivated based on settings entered by a clinician, or possibly patient 12. Hence, some programs or groups may be configured for use with posture responsive therapy while other programs or groups may not be configured for use with posture responsive therapy. A programmer such as programmer 30 or 60 may be configured to present automatic posture response icon 182 to indicate to a user whether particular programs or program groups, such as groups selected by a user and identified by group identifier 186, are configured to support posture state-responsive therapy. In some cases, if posture state-responsive therapy supported by the automatic posture response feature is desired, patient 12 may need to switch therapy to a different group that has automatic posture responsive therapy activated for IMD 14 to adjust therapy according to the patient 12 posture state.

Automatic posture response icon 182 provides an immediate indication as to whether a selected program or group of programs is posture state-responsive. With automatic posture response icon 182 presented by programmer 30, it is not necessary for the user to wonder about the posture state-responsive status of a program or group, or memorize such status. Instead, the status may be immediately displayed to the user via the user interface of programmer 30, permitting the user to switch to a different therapy on the basis of whether posture state-responsive therapy is desired or not. Although described as an icon, automatic posture response icon 182 may alternatively be presented by any textual, graphical, tactile, audible or visible indication suitable to convey the posture state-responsive status of the selected therapy program or group to the user.

Figure 10:
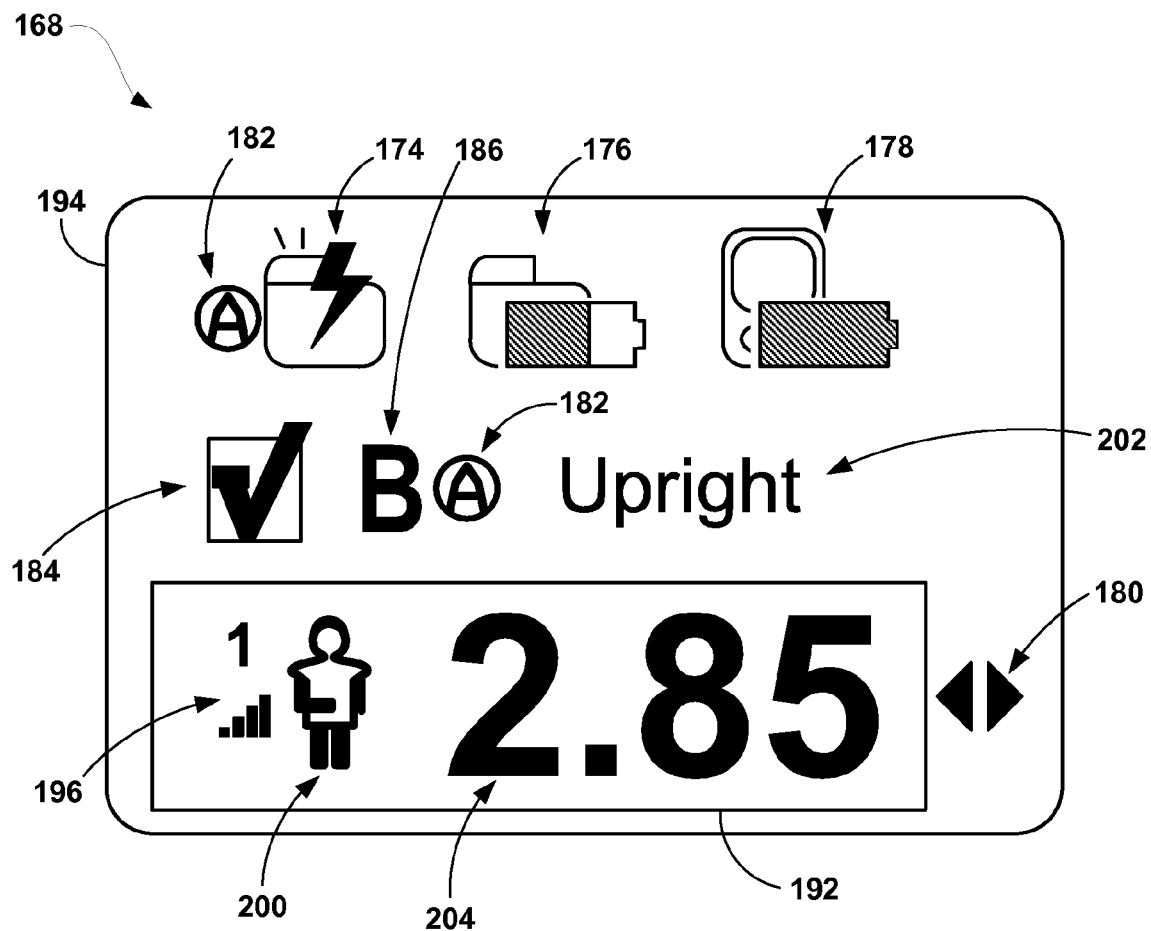
FIG. 10 is a conceptual diagram illustrating an example user interface of a patient programmer for delivering therapy information that includes posture information to the patient.

FIG. 10 is a conceptual diagram illustrating an example user interface 168 of a patient programmer 30 for delivering therapy information that includes posture information to the patient. In other examples, user interface 168 may also be shown on clinician programmer 60. In the example of FIG. 10, display 36 of patient programmer 30 provides user interface 168 to the user, such as patient 12, via screen 194. Screen 194 includes stimulation icon 174, IMD battery icon 176, programmer battery icon 178, and automatic posture response icon 182, similar to screen 170 of FIG. 9. In addition, screen 194 includes group selection icon 184, group identifier 186, supplementary posture state indication 202, program identifier 196, posture state indication 200, amplitude value 204, selection box 192, and selection arrows 180. User interface 168 provides information to patient 12 regarding group, program, amplitude, automatic posture response status, and posture state information. More or less information may be provided to patient 12, as desired by the clinician or the patient.

In FIG. 10, group identifier 186 indicates that group "B" is active, and automatic posture response icon 182 indicates group "B" (containing one or more programs) is activated to allow IMD 14 to automatically adjust therapy according to the patient 12 posture state. Specifically, the posture state is the posture state of patient 12 in the example of FIG. 10. Program identifier 196 illustrates that information regarding program "1" of group "B" is displayed on screen 194, such as amplitude value 204 illustrating the current voltage amplitude of program "1" is 2.85 Volts. Patient 12 may scroll through different programs of the group by using navigation arrows 180 via arrows 44 and 48 of control pad 40.

In addition, posture state indication 200 shows that IMD 14 is detecting that patient 12 is in the upright or standing posture. Supplementary posture state indication 202 supplements posture state indication 200 by explaining in words to patient 12 the exact posture being detected by posture state module 86 of IMD 14. Posture state indication 200 and supplementary posture state indication 202 change according to the sensed, or detected, posture state detected by IMD 14. The posture state may be communicated to the external programmer immediately when IMD 14 detects a posture change, or communicated periodically or non-periodically by IMD 14 unilaterally or upon receiving a request from the programmer. Accordingly, the posture state indication 200 and/or supplementary posture state indication 202 may represent a current, up-to-the minute status, or a status as of the most recent communication of posture state from IMD 14. Posture state indication 200 is shown as a graphical representation, but the posture state indication may alternatively be presented as any one of a symbolic icon, a word, a letter, a number, an arrow, or any other representation of the posture state. In some cases, posture state indication 200 may be presented without supplementary posture state indication 202.

Selection box 192 indicates that patient 12 view other programs within group "B" using selection arrows 180. Selection box 192 may be moved to select other screen levels with control pad 40 in order to navigate through other stimulation groups or adjustable elements of the therapy. When patient 12 selects a different program with control pad 40, program identifier 196 will change number to correctly identify the current program viewed on screen 194

As mentioned above, in addition to graphical, textual or other visible indications of posture state, the external programmer may present audible and/or tactile indications of posture state via any of a variety of audible or tactile output media. Again, an audible indication may be spoken words stating a posture state, or different audible tones, different numbers of tones, or other audible information generated by the programmer to indicate posture state. A tactile indication may be different numbers of vibratory pulses delivered in sequence or vibratory pulses of different lengths, amplitudes, or frequencies.

FIGS. 11A-11E are conceptual diagrams illustrating examples of different posture state indications that may be graphically displayed on a user interface, e.g., user interface 168. As shown in FIGS. 11A-11E, posture state indications 208A-208E (collectively "posture state indications 208") are different posture state indications that are representative of different patient posture states. Posture state indications 208 are alternative embodiments of posture state indication 200 of FIG. 10. Specifically, posture state indications 208 are graphic representations that may be representative of static posture patient 12 typically assumes during daily routines, such as standing and sleeping. Although posture state indications 208 are shown in conjunction with program identifier 210, similar to program identifier 196 of FIG. 10, posture state indications 208 may be presented alone. Posture state indications 208 are one type of posture state indication, in that all posture state indications 208 may be considered to be a set of posture state indications. Posture state indications 208 are shown in black and white, but the indications may be presented with multiple colors, sizes, or other creative alternatives.

FIG. 11A illustrates a posture state indication 208A which is representative of an upright posture of patient 12. Posture state indication 208A is an example representation of a person standing in an upright position, perpendicular to the plane of the ground. In some examples, posture state indication 208A may be a symbolic icon that patient 12 would associate with their standing posture state.

FIG. 11B illustrates posture state indication 208B which is representative of a patient posture state lying down on their back. When patient 12 lies on their back, the posture state parameter value, generated by the posture state module, will indicate that the patient posture state of the patient lying on their back corresponds to posture state indication 208B. FIG. 11C illustrates posture state indication 208C which is representative of the patient posture state lying on their right side, and FIG. 11D illustrates posture state indication 208D which is representative of the patient posture state lying on their left side. Additionally, FIG. 11E shows posture state indication 208E, which is representative of the patient posture state lying front, e.g., lying on their stomach.

When patient 12 changes, or transitions, to a different posture state, processor 104 may force user interface 168 to change the presented posture state indication to correctly indicate the current posture state that is detected. The new posture state indication may be presented immediately upon detection, after a transition delay until the new detected posture state is stable, as soon as IMD 14 can communicate with patient programmer 30, when patient programmer 30 requests the current posture state parameter value or posture state, or at any other time after patient 12 assumes the new posture state.

When the new posture state indication is presented, patient programmer 30 may indicate that the posture state indication has changed. For example, the new posture state indication may blink on and off for ten seconds before the posture state indication is presented as a solid indication. Alternatively, patient programmer 30 may present a pop-up window for a short time that indicates that the posture state has changed. In other embodiments, patient programmer 30 may provide an audible alert so that patient 12 recognizes that IMD 14 has detected the change in posture state. These and other transitional alerts may be implemented to further increase the efficacy of therapy via patient 12 feedback and interaction with patient programmer 30.

Posture state indications 208 are only one type of posture state indications. In other examples, there may be additional posture state indications 208 not illustrated herein. For example, posture state indications 208 may also include an inverted posture state indication, a reclining posture state indication, specific activities, or any other posture state indications that may be representative of the patient posture state. The clinician or patient 12 may even select other posture state indications from a catalog to describe certain posture states that patient 12 commonly uses.

Figure 12:
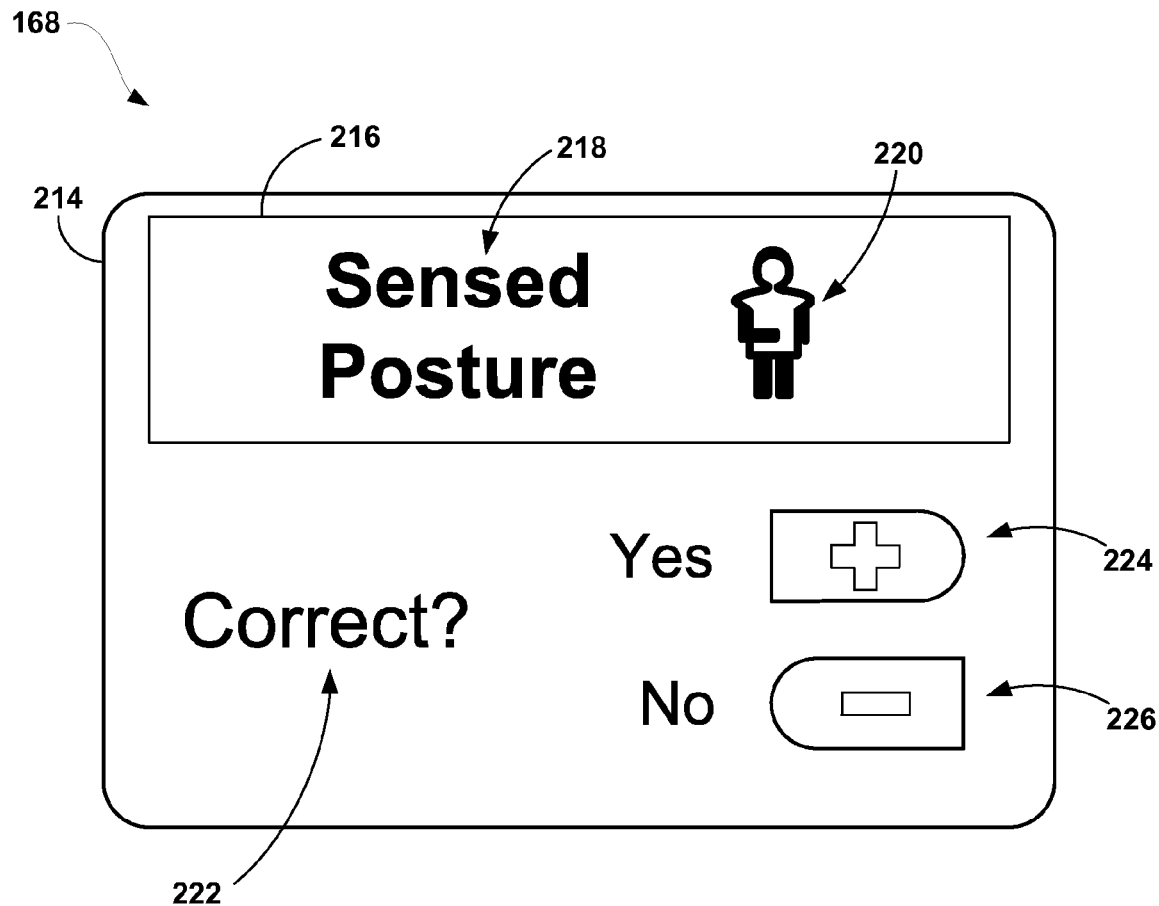
FIG. 12 is a conceptual diagram illustrating an example user interface for prompting the user to indicate if the sensed patient posture state is correct.

FIG. 12 is a conceptual diagram illustrating an example screen 214 of user interface 168 for prompting the user to indicate if the sensed patient posture state is correct. As shown in FIG. 12, screen 214 presents selection box 216, mode text 218, posture state indication 220, prompt text 222, yes prompt 224, and no prompt 226. If posture state indication 200 of FIG. 10 is not representative of the current posture state, patient 12 may use control pad 40 to enter screen 214 to confirm the correct posture state. Mode text 218 displays "sensed posture" to indicate that the current sensed posture state is that posture state shown by posture state indication 220.

Figure 13:
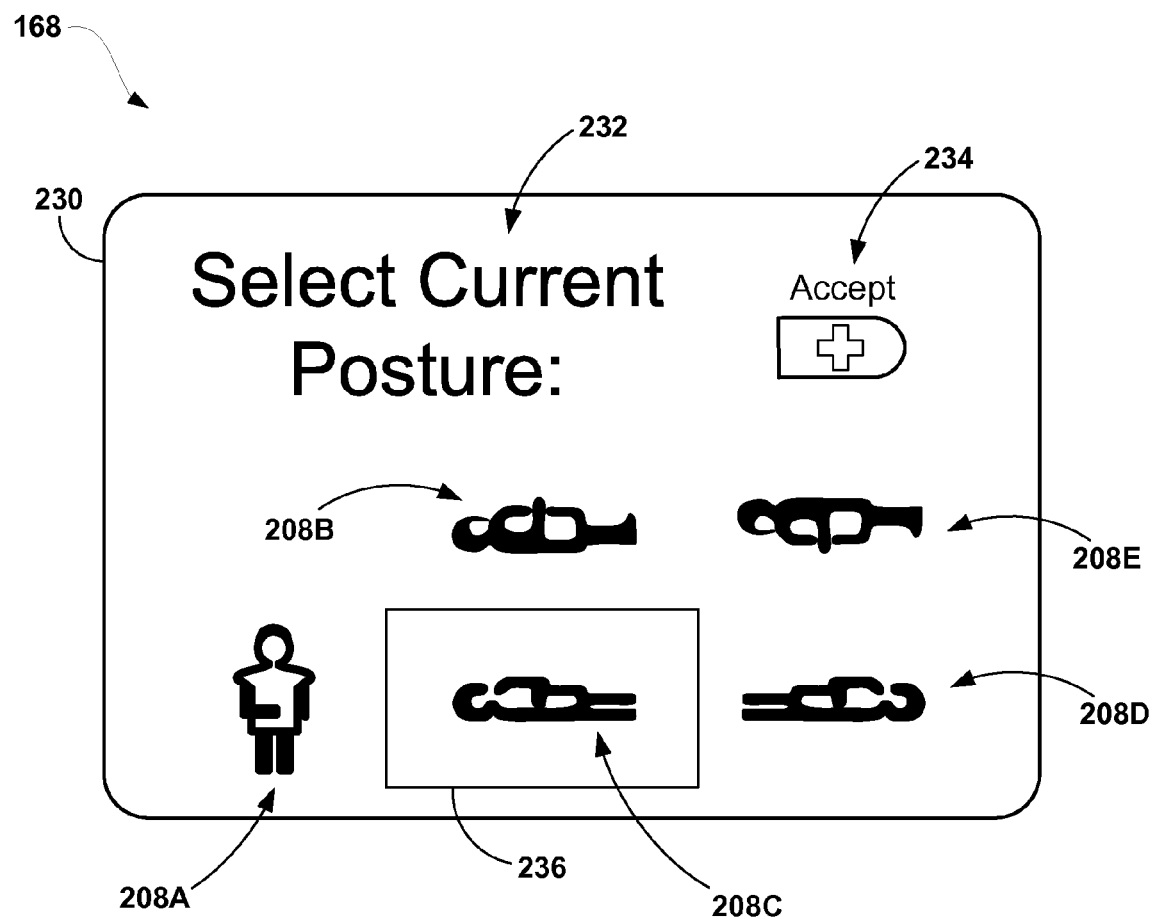
FIG. 13 is a conceptual diagram illustrating an example user interface for receiving a confirmed posture state from the user.

If the presented posture state indication 220 is not correct, patient 12 may move selection box 216 on screen 214 from mode text 218 to highlight prompt text 222. Patient 12 may confirm that the sensed posture of posture state indication 220 is the correct current posture state of patient 12 by pressing increase button 52 of patient programmer 30 as shown by yes prompt 224. If the presented posture state indication 220 is incorrect, then patient 12 may select decrease button 50 of patient programmer 30 as shown by no prompt 226. Alternatively, patient 12 may use control pad 40 to highlight either yes prompt 224 or no prompt 226 with selection box 216. If the sensed posture shown by posture state indication 220 is correct, patient 12 may be returned to the normal operating screen of the user interface. If patient 12 indicates that the sensed posture state is incorrect, processor 104 may prompt patient 12 to select the appropriate posture state indication to allow IMD 14 to re-orient the activity sensor, or posture state module, as shown in FIG. 13. Any of a variety of techniques for presenting sensed posture and eliciting patient feedback concerning accuracy of the sensed posture may be used. Accordingly, the particular example provided in FIG. 12 is provided for purposes of illustration and without limitation to other approaches or techniques.

FIG. 13 is a conceptual diagram illustrating an example screen 230 of user interface 168 for receiving a confirmed posture state from the user. As shown in FIG. 13, screen 230 presents mode text 232, accept prompt 234, posture state indications 208, and selection box 236. Mode text 232 displays "select current posture" to indicate to patient 12 that the correct current posture state indication needs to be confirmed by patient 12. Patient 12 may confirm the posture state by moving selection box 236 over the current one of posture state indications 208 and pressing increase button 52 suggested by accept prompt 234. Alternatively, patient 12 may press the center of control pad 40 or depress a different enter key. In the example of FIG. 13, patient 12 is lying on their right side, so the current patient posture state is represented by posture state indication 208C. In other examples, if a touch screen is provided, patient 12 may use a stylus to select a desired posture state indication.

In some examples, IMD 14 may require the selection of more than one confirmed posture state to be able to re-orient the posture sensor module after patient 12 has indicated that the presented posture state indications are incorrect. Patient 12 may need to assume two different posture states and select the corresponding posture state indications, as prompted by user interface 168. Alternatively, IMD 14 may prompt patient 12 to confirm three or more posture states, up to all of the possible posture states represented by the posture state indications. Hence, user interface 168 may guide the patient 12 through a process of occupying particular postures and receiving user input indicating the posture state indications that correspond to such postures.

Figure 14A:
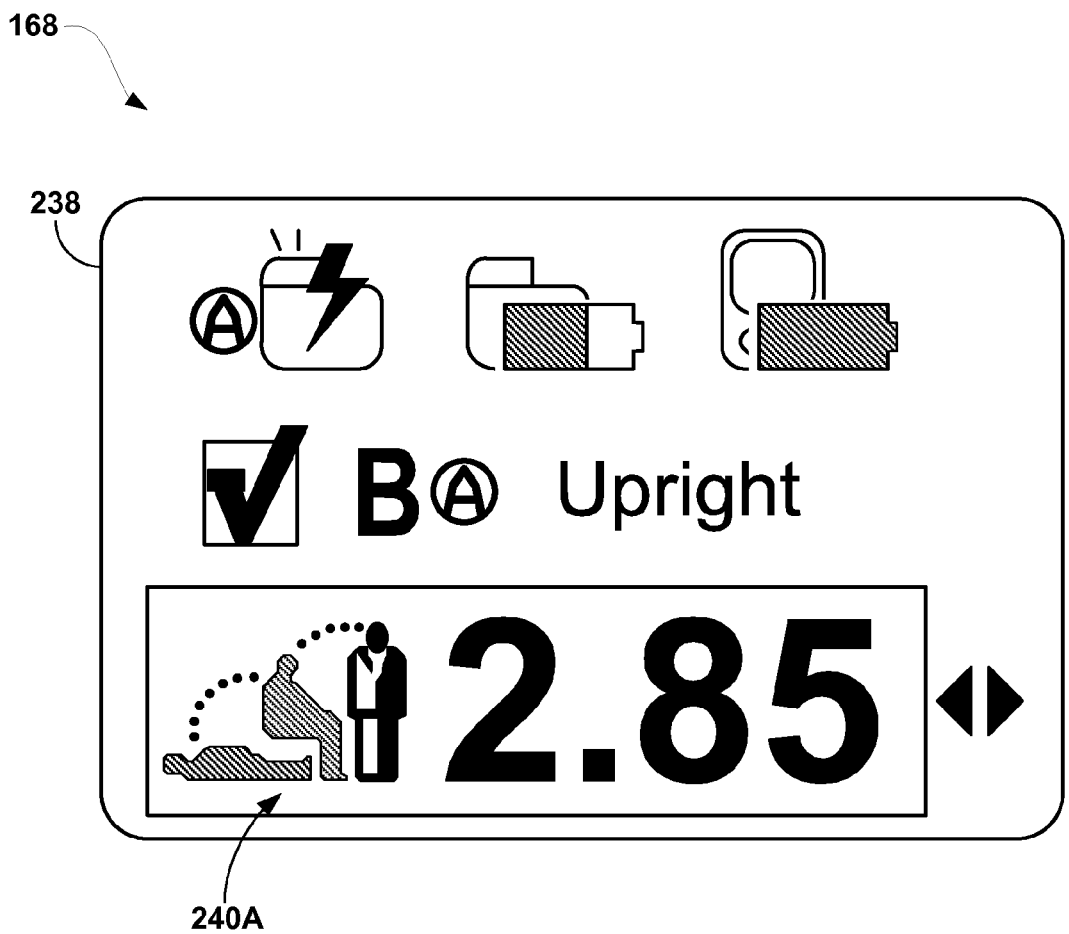
FIGS. 14A-14D are conceptual diagrams illustrating different posture state indications that may represent the patient posture state on a user interface.

FIGS. 14A-14D are conceptual diagrams illustrating different posture state indications 240A-D that may represent the patient posture state on screen 238 of user interface 168. As shown in FIG. 14A, screen 238 presents therapy information to patient 12 in the form of group indicators and amplitude indicators. In addition, screen 238 presents posture state indication 240A, an embodiment of posture state indication 200, to represent the current patient posture state sensed by the activity sensor. In the example of FIG. 14A, posture state indication 240A represents that patient 12 is in an upright posture state. Posture state indication 240A also presents two other posture states that patient 12 could assume, but these posture states are not currently detected. These additional posture states may be helpful to patient 12 to ensure that the patient is aware of the other possible posture states detectable by IMD 14 before patient 12 decides that the incorrect posture state is being sensed. All of posture state indications 240A-D are one type of posture state indication, and the type may be selectable by the clinician or patient 12.

Figure 14B:
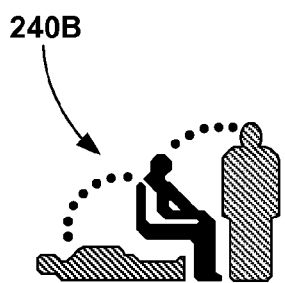
Figure 14C:
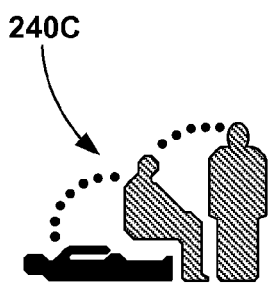
Figure 14D:
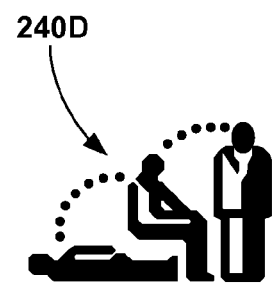

FIG. 14B illustrates posture state indication 240B, which represents patient 12 in a sitting or reclining posture state. Posture state indication 240B shows the upright and lying down posture states as grayed out because they are not currently detected by the activity sensor. FIG. 14C illustrates posture state indication 240C, which represents patient 12 in a lying down posture state. In cases where the activity sensor does not differentiate between different postures when patient 12 is lying down, posture state indication 240C may be sufficient. If the activity sensor and IMD 14 can indicate the exact posture of patient 12, the supplemental posture state indication, may describe the posture state with text, e.g., lying back, lying front, lying right, and lying left. Posture state indication 240D illustrated in FIG. 14D shows all three posture states. Patient programmer 30 may present posture state indication 240D when patient 12 continuously transitions between multiple posture states within a certain period of time. Alternatively, or additionally, user interface 168 may blink posture state indication 240D when there is a problem with the activity sensor that needs user input or remote attention.

Figure 15A:
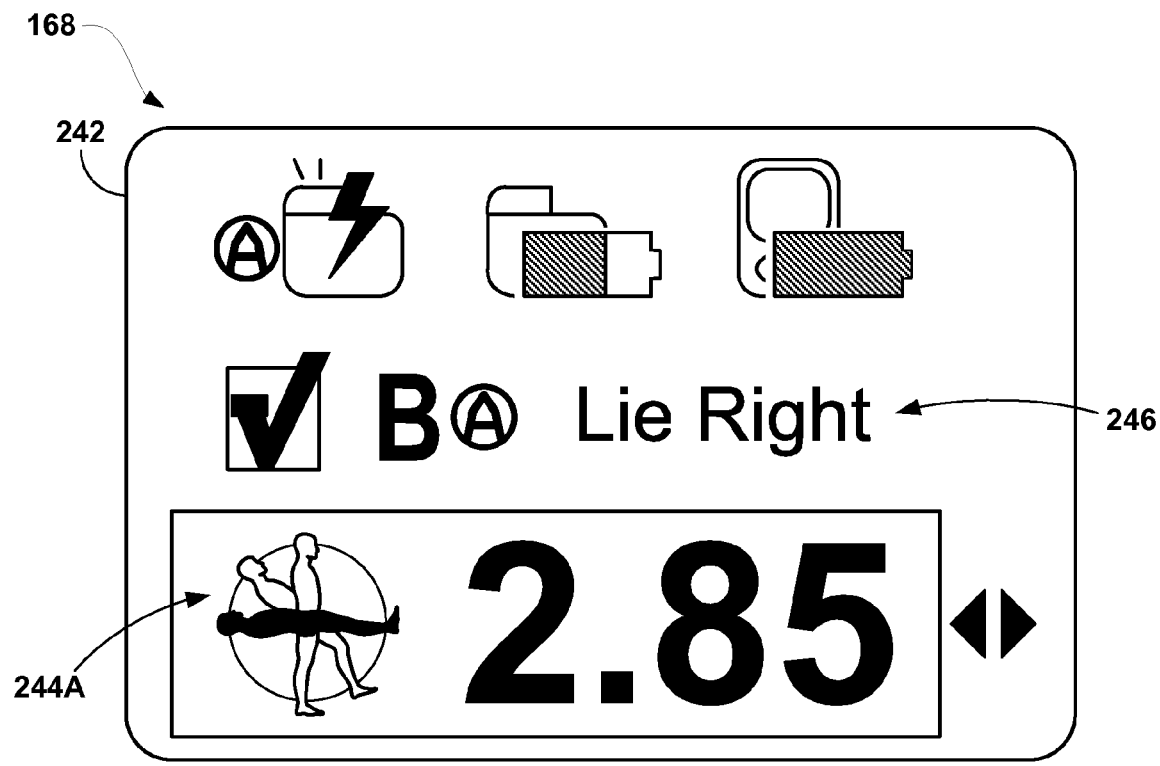
FIGS. 15A-15C are conceptual diagrams illustrating different posture state indications that show the current patient posture state and other non-current patient posture states.
Figure 15B:
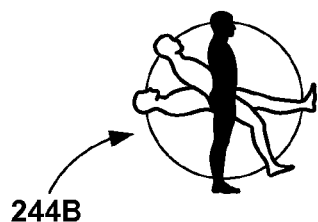
Figure 15C:
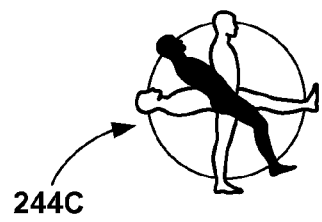

FIGS. 15A-15C are conceptual diagrams illustrating different posture state indications 244A-C that show the current patient posture state and other non-current patient posture states in user interface 168. As shown in FIG. 15A, screen 242 presents therapy information to patient 12 in the form of group indicators and amplitude indicators. In addition, screen 242 presents posture state indication 244A, an embodiment of posture state indication 200, to represent the current patient posture state sensed by the activity sensor. In the example of FIG. 15A, posture state indication 244A represents that patient 12 is in a lying down posture state. All of posture state indications 244A-C of FIGS. 15A-C are one type of posture state indication, and the type may be selectable by the clinician or patient 12. However, posture state indication 244A does not present all of the posture state information to patient 12.

Supplementary posture state indication 246 supplements posture state indication 244A by additionally describing the lying down posture as "lie right," i.e., patient 12 is lying on their right side. Supplementary posture state indication 246 may be particularly useful if the therapy programmed by the clinician benefits from subtle changes in posture state. These subtle changes to the patient posture state may be detectable with narrow posture cones configured by either the clinician or patient 12 during the course of therapy. For example, supplementary posture state indication 246 may describe an activity that is being performed while patient 12 is engaged in the posture shown in posture state indication 244A. In this manner, posture state indication 244A may show the general posture state of patient 12 and supplementary posture state indication 246 may further define the specific posture state detected by IMD 14. Supplementary posture state indication 246 may be text in the language of patient 12, a letter, a number, another graphical representation, an icon, an arrow, or even an audible alert delivered by a speaker of patient programmer 30.

FIG. 15B illustrates posture state indication 244B, which represents patient 12 in an upright posture state. Posture state indication 244B shows the reclining and lying down posture states as just an outline because they are not currently detected by the activity sensor. FIG. 15C illustrates posture state indication 244C, which represents patient 12 in a reclining posture state. Posture state indication 244C may be representative of sitting in a chair, driving, or some other posture or activity that includes patient 12 assuming that posture state. In other embodiments, there may be additional posture state indications of the same type as posture state indications 244A-C.

Figure 16A:
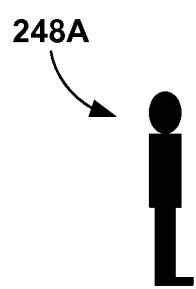
FIGS. 16A-16F are conceptual diagrams illustrating different posture state indications representative of a posture and/or an activity.
Figure 16B:
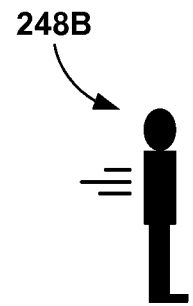

FIGS. 16A-16F are conceptual diagrams illustrating a type of different posture state indications 248A-F (collectively "posture state indications 248") representative of a posture or an activity. Posture state indications 248 are embodiments of posture state indication 200 and example posture state indications that may include representations of activity as well as a static posture. FIG. 16A illustrates posture state indication 248A that is representative of patient 12 standing upright. FIG. 16B illustrates posture state indication 248B that is representative of patient 12 engaged in an activity while assuming the upright posture. IMD 14 may detect the activity by monitoring the posture state parameter value from the activity sensor. The vector direction of the posture state parameter value may be within the same posture cone between both posture state indications 248A and 248B. However, the magnitude of the vector may change in magnitude over a predetermined threshold that indicates a further activity. In this case, the posture state parameter value may associate with posture cone 154B, for example, which is represented by posture state indication 248B instead of posture state indication 248A.

Figure 16C:
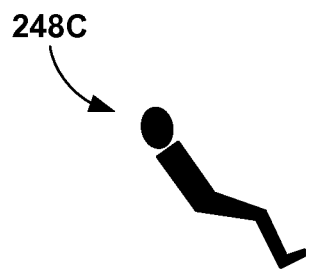
Figure 16D:
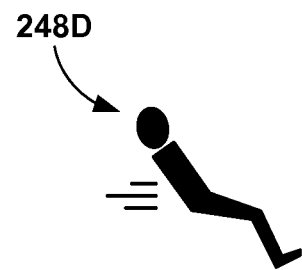
Figure 16E:
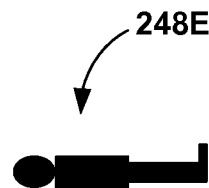
Figure 16F:
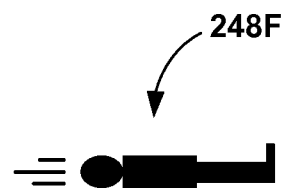

FIG. 16C illustrates posture state indication 248C, which is representative of patient 12 assuming a reclining posture. FIG. 16D illustrates posture state indication 248D, which is similar to posture state indication 248C. However, posture state indication 248D represents activity of patient 12 in addition to the detected reclining posture. FIG. 16E illustrates posture state indication 248E, which is representative of patient 12 lying down. In contrast, FIG. 16F illustrates posture state indication 248F to represent that patient 12 is lying down and also engaged in some activity, e.g., swimming, lifting weights, or some other activity. In alternative embodiments, posture state indications 248 may include text in addition to the graphical representation shown in FIGS. 16A-F.

FIGS. 17A-17E are conceptual diagrams illustrating a type of different posture state indications 250A-E (collectively "posture state indications 250") that may represent different patient postures. Posture state indications 250 are embodiments of posture state indication 200 and show the orientation of the head of patient 12 in relation to the ground. In this manner, posture state indications 250 may tell patient 12 what posture state IMD 14 is detecting. Posture state indication 250A includes head 252A oriented upright with respect to ground 254. Posture state indication 250A is an example representation of a person standing or sitting in an upright position, perpendicular to the plane of the ground.

Figure 17A:
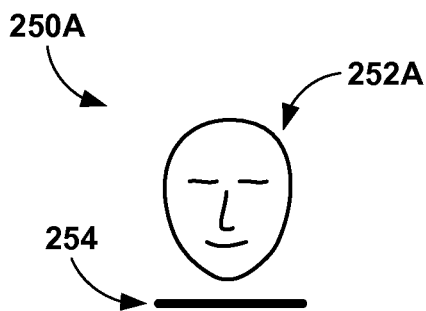
FIGS. 17A-17E are conceptual diagrams illustrating different posture state indications that may represent different patient postures.
Figure 17B:
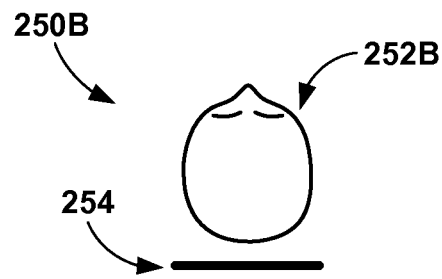
Figure 17C:
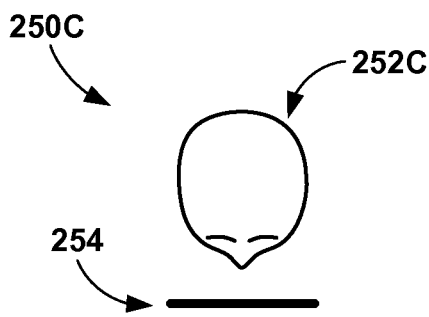
Figure 17D:
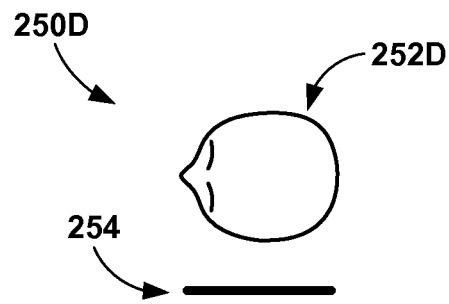
Figure 17E:
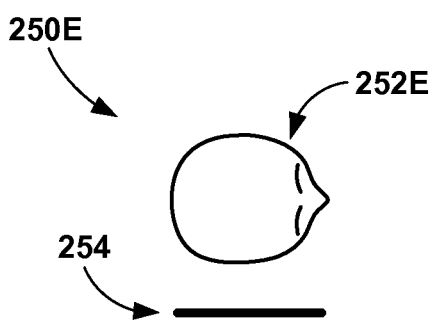

FIG. 17B illustrates posture state indication 250B which is representative of a patient posture state lying down on their back. Head 252B is oriented with the eyes and nose pointed away from ground 254 in posture state indication 250B. FIG. 17C illustrates posture state indication 250C which shows head 252C oriented facing ground 254. Posture state indication 250C is representative of the patient posture state of lying down on their chest, or lying front. FIG. 17D illustrates posture state indication 250D which includes head 252D oriented with the eyes and nose pointed to the left of ground 24. Posture state indication 250D is representative of the patient posture state when patient 12 lies down on their left side. Additionally, FIG. 17E illustrates posture state indication 250E which includes head 252E oriented to the right of ground 254. Posture state indication 250E is representative of patient 12 lying on their right side.

Posture state indications 250 may include any other attributes, actions, or presentation methods described herein with regard to any embodiments of posture state indication 200. Posture state indications 250 may be animated when transitioning between different posture state indications or to indicate the patient 12 that an input or attention is needed to address a problem with IMD 14 or patient programmer 30. Further, posture state indications 250 are only one type of posture state indications. In other examples, there may be additional posture state indications 250 not illustrated herein. For example, posture state indications 250 may also include an inverted posture state indication, a reclining posture state indication, specific activities, or any other posture state indications that may be representative of the patient posture state.

Figure 18A:
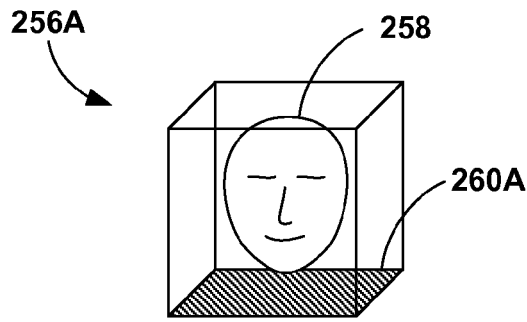
FIGS. 18A-18F are conceptual diagrams illustrating different posture state indications that utilize a changing ground for orientation.

FIGS. 18A-18F are conceptual diagrams illustrating different posture state indications 256A-F (collectively "posture state indications 256") that utilize a changing reference ground for orientation. Posture state indications 256 are embodiments of posture state indication 200 and show a static orientation of head 258 within a three-dimensional space around which a reference ground moves to show the posture state of patient 12. FIG. 18A shows posture state indication 256A which includes head 258 and reference ground 260A oriented below head 258 to indicate that patient 12 is in an upright posture state.

Figure 18B:
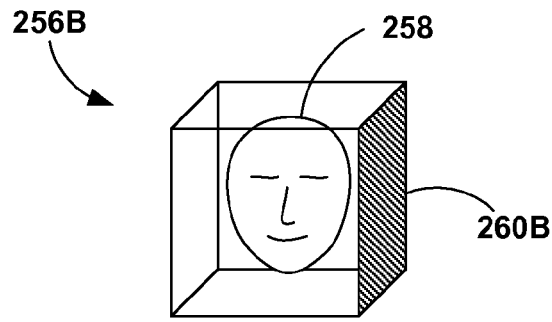
Figure 18C:
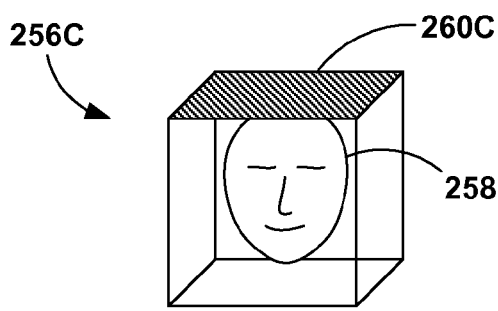
Figure 18D:
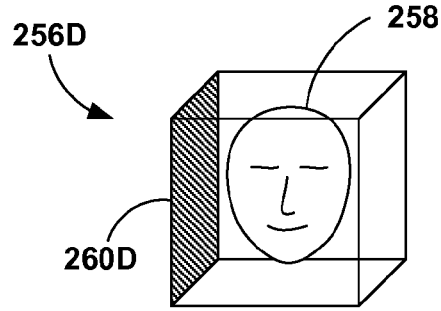
Figure 18E:
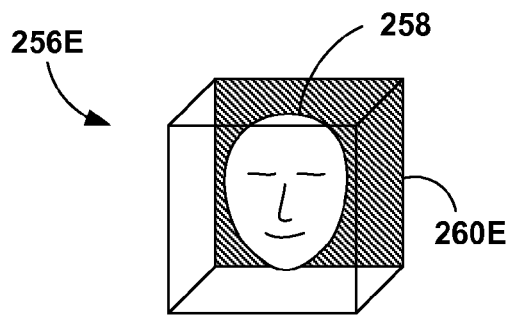
Figure 18F:
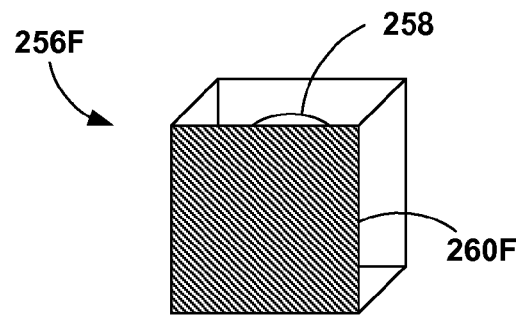

FIG. 18B illustrates posture state indication 256B which is representative of a patient posture state lying down on their left side. Reference ground 260B is positioned on the left side of patient 12. FIG. 18C illustrates posture state indication 256C which shows reference ground 260C as positioned above head 258. Posture state indication 256C is representative of patient 12 being in an inverted posture state. FIG. 18D shows posture state indication 256D which includes reference ground 260D positioned to the right of head 258. Posture state indication 256D is representative of patient 12 lying down on their right side. Further, FIG. 18E illustrates posture state indication 256E which shows reference ground 260E positioned behind head 258. Posture state indication 256E is representative of the posture state parameter value detecting that patient 12 is lying down on their back. In addition, FIG. 18F illustrates posture state indication 256F which includes reference ground 260F positioned in front of head 258 to represent that the patient posture state is lying on the chest of patient 12.

Posture state indications 256 may include any other attributes, actions, or presentation methods described herein with regard to any embodiments of posture state indication 200. Further, posture state indications 256 are only one type of posture state indications. In other examples, there may be additional posture state indications 256 not illustrated herein. For example, posture state indications 256 may also include an element or icon indicating the activity of patient 12 instead of only showing a static posture.

Figure 19A:
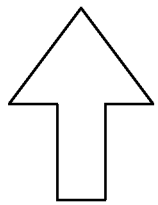
FIGS. 19A-19F are conceptual diagrams illustrating different posture state indications that utilize an arrow.

FIGS. 19A-19F are conceptual diagrams illustrating different posture state indications 262A-F (collectively "posture state indications 262") that utilize arrows. Posture state indications 262 are embodiments of posture state indication 200 and show an arrow that points in the direction of the posture state of patient 12. FIG. 19A shows posture state indication 262A which is an arrow pointing up to represent that patient 12 is in the upright posture state.

Figure 19B:
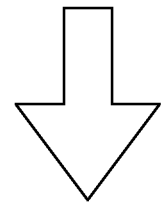
Figure 19C:
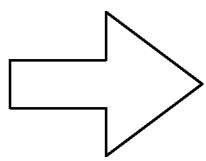
Figure 19D:
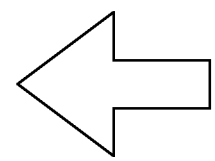
Figure 19E:
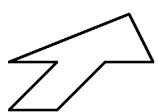
Figure 19F:
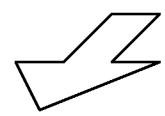

FIG. 19B illustrates posture state indication 262B which is an arrow pointing down to represent that patient 12 inverted. FIG. 19C illustrates posture state indication 262C which is an arrow pointing to the right to represent that the posture state parameter value detects that patient 12 is lying down on their right side. FIG. 19D shows posture state indication 262D which shows an arrow pointing to the left to represent that patient 12 is lying down on their left side. Further, FIG. 19E illustrates posture state indication 262E which is an arrow pointing back into the screen to represent that patient 12 is lying down on their back. Additionally, FIG. 19F illustrates posture state indication 262F which is an arrow pointing towards the user to indication that patient 12 is lying down on their chest, or lying front.

Posture state indications 262 may include additional arrows or arrows that change in size depending on the activity of patient 12 detected by IMD 12. Posture state indications 262 may also include any other attributes, actions, or presentation methods described herein with regard to any embodiments of posture state indication 200. Further, posture state indications 262 are only one type of posture state indications. In other examples, there may be additional posture state indications 262 not illustrated herein. For example, posture state indications 262 may also include an element or icon indicating the activity of patient 12 instead of only showing a static posture.

FIGS. 20A-20F are conceptual diagrams illustrating different posture state indications 264A-F (collectively "posture state indications 264") that represent activities of the patient. Posture state indications 264 are embodiments of posture state indication 200 and show activities of patient 12 that are patient posture state. The posture state parameter value from the activity sensor may indicate that the posture state of patient 12 includes an activity as measured by the changing magnitude of the posture state parameter value, or some other measurement. Just as patient 12 may benefit from changing therapy parameters due to static posture, patient 12 may benefit from an adjustment in therapy parameters due to the recognition that patient 12 is engaged in a particular activity.

Figure 20A:
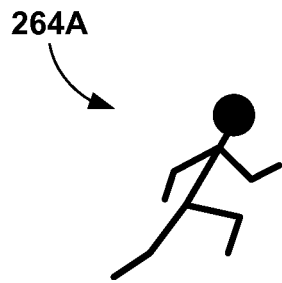
FIGS. 20A-20F are conceptual diagrams illustrating different posture state indications that represent activities of the patient.
Figure 20B:
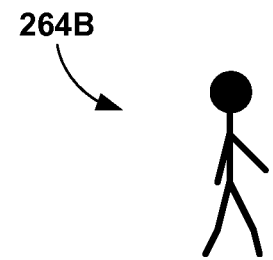
Figure 20C:
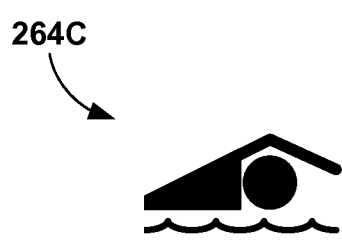
Figure 20D:
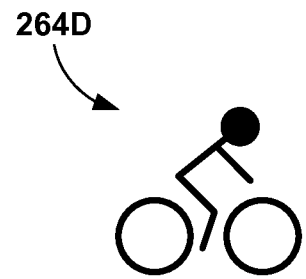
Figure 20E:
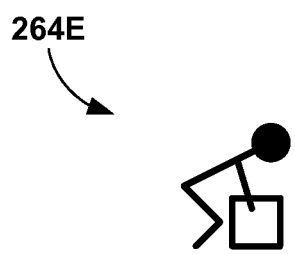
Figure 20F:
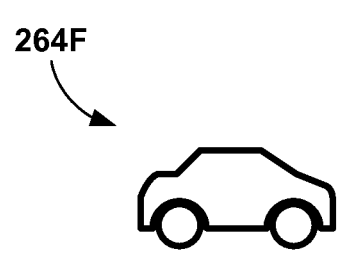

FIG. 20A shows posture state indication 264A which is a representation of patient 12 running. FIG. 20B illustrates posture state indication 264B which is a representation of patient 12 walking. FIG. 20C illustrates posture state indication 264C which is a representation of patient 12 swimming. FIG. 20D shows posture state indication 264D which is a representation of patient 12 engaged in the activity of riding a bike. Moreover, FIG. 20E illustrates posture state indication 264E which is a representation of patient 12 lifting items or doing other work in which patient 12 is bending over frequently. Additionally, FIG. 20F illustrates posture state indication 264F which is a representation of patient 12 riding in a car. All of posture state indications 264 are representative of some posture state that includes an activity that involves repetitious or sporadic movement that may benefit from a change in therapy parameters.

Posture state indications 264 may also include any other attributes, actions, or presentation methods described herein with regard to any embodiments of posture state indication 200. Moreover, posture state indications 264 are only one type of posture state indications, e.g., activity posture state indications. In other examples, there may be additional posture state indications 264 not illustrated herein. For example, posture state indications 264 may also include typing, rowing, washing dishes, gardening, playing a musical instrument, or any other activity patient 12 may be engaged.

Figure 21:
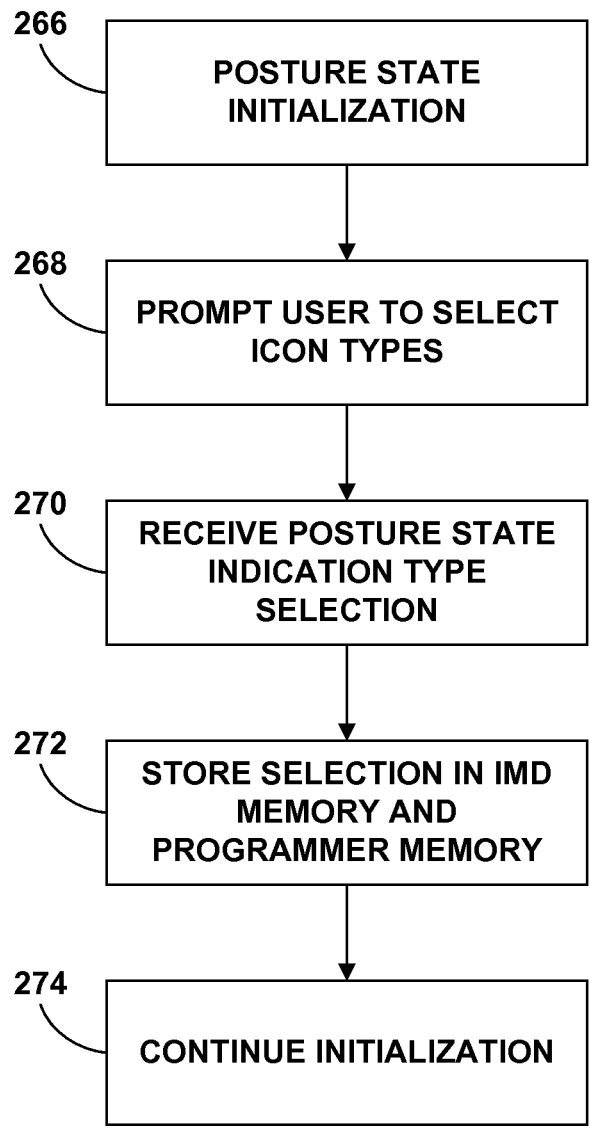
FIG. 21 is a flow chart illustrating an example method for initially selecting the type of posture state indications to be presented on the user interface.

FIG. 21 is a flow chart illustrating an example method for initially selecting the type of posture state indications for the user interface to present on the user interface. As shown in FIG. 21, the user, e.g., the clinician, physician, technician, or patient 12, enters the posture state initialization screen or menu that allows IMD 14, or IMD 26, to detect the posture state of patient 12 from the sensed posture state parameter value from the activity sensor (266). Generally, the user will perform the posture state initialization on clinician programmer 60, but the user may use patient programmer 30 or a different external programmer 20. Next, clinician programmer 60 prompts the user to select the type of posture state indication to use when presenting the posture state representation to patient 12 (268). The user may select from any of the posture state indication types described herein, such as posture state indications 200, 208, 240, 244, 248, 250, 256, 262, or 264. In some embodiments, the user may select a type of posture state indication for the posture and different type of posture state indication for the activity of patient 12.

After the user has selected the desired type of posture state indication, clinician programmer 60 receives the posture state indication type selection (270) and stores the selection in programmer 60 memory and IMD 14 memory (272). IMD 14 may communicate the selection to patient programmer 30 or clinician programmer 60 may directly communicate the selection of posture state indication type to patient programmer 30. In some embodiments, the posture state indication type selection may only be stored in the memory of IMD 14 and communicated to the appropriate external programmer 20 as needed. After the posture state indication type is selected, the user continues initialization via the clinician programmer 60 (274).

Figure 22:
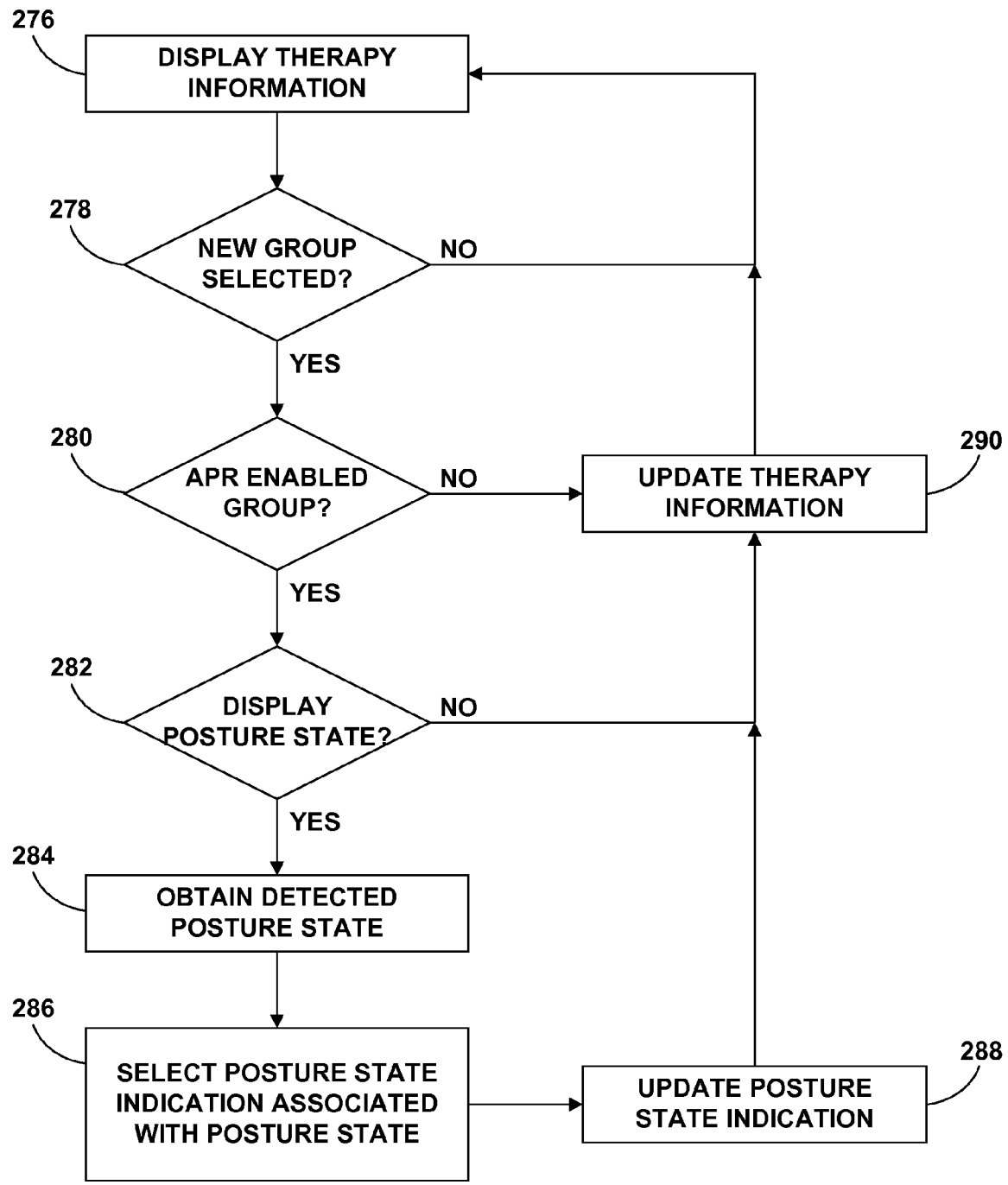
FIG. 22 is a flow chart illustrating an example method for selecting the representative posture state indication and presenting the posture state indication on the user interface.

FIG. 22 is a flow chart illustrating an example method for selecting the representative posture state indication and presenting the posture state indication on the user interface. In general, a programmer receives a posture state detection indicating a posture state currently occupied by a patient, obtains a posture state indication representative of the detected posture state, and presents the posture state indication via a user interface of a medical device programmer. The detected posture state may be detected by IMD 14 and communicated to an external programmer.

The example of FIG. 22 is described with respect to patient programmer 30, but any external programmer, such as clinician programmer 60 may alternatively be used. As shown in FIG. 22, patient programmer 30 displays therapy information to patient 12 (276). Therapy information may be any combination of stimulation amplitude, pulse width, pulse frequency, electrode combination, drug delivery rate, bolus size, active program, active group, battery levels, stimulation activity, automatic posture response, posture state indications, or any other information that is related to the therapy received by patient 12.

If a new group has been selected by patient 12 for stimulation therapy (278), processor 104 of patient programmer 30 checks to see if the automatic posture state response (APR) has been enabled (280). If the automatic posture response has not been enabled, processor 104 updates the therapy information (290) and continues to display the therapy information (276). If the automatic posture response has been enabled for the selected group of stimulation programs (280), then processor 104 determines if the posture state indication is to be displayed on user interface 168, for example (282). If the posture state indication is not to be displayed, then processor 104 updates the therapy information (290) and displays the therapy information (276).

If processor 104 is to display the posture state indication for the selected group (282), the processor 104 may obtain the posture state indication by retrieving, or obtaining, a current posture state detection posture state parameter value (284) from posture state module 86 or processor 80 of IMD 16 and selecting the posture state indication that is associated with the detected posture state (286). The detected posture state indicates the posture stated currently occupied by the patient. Processor 104 then updates the posture state indication (288), updates the therapy information (290), and displays the therapy information (276).

While in the selected group for which the posture state indication is to be displayed, processor 104 continues to update the posture state indication according to the posture state parameter value and the instructions stored within memory 108. For example, processor 104 may periodically communicate with IMD 14 to receive the current posture state parameter value or currently detected posture state. Alternatively, IMD 14 may send an update communication to patient programmer 30 whenever the posture state has changed. In any case, processor 104 may continue to update the posture state indication according to the currently detected posture state during therapy with the selected group of stimulation therapy programs.

In other embodiments, any automatic posture response enabled group may automatically trigger processor 104 to display the posture state indication that corresponds to the detected posture state or posture state parameter value. In addition, the posture state indication may be provided at all times, even if the selected group does not deliver therapy based upon the sensed posture state of patient 12. This embodiment may be beneficial when IMD 14 is configured to collect and record posture state information that is used to determine the effectiveness of therapy or evaluate the potential of automatic posture response to increase therapy efficacy.

Figure 23:
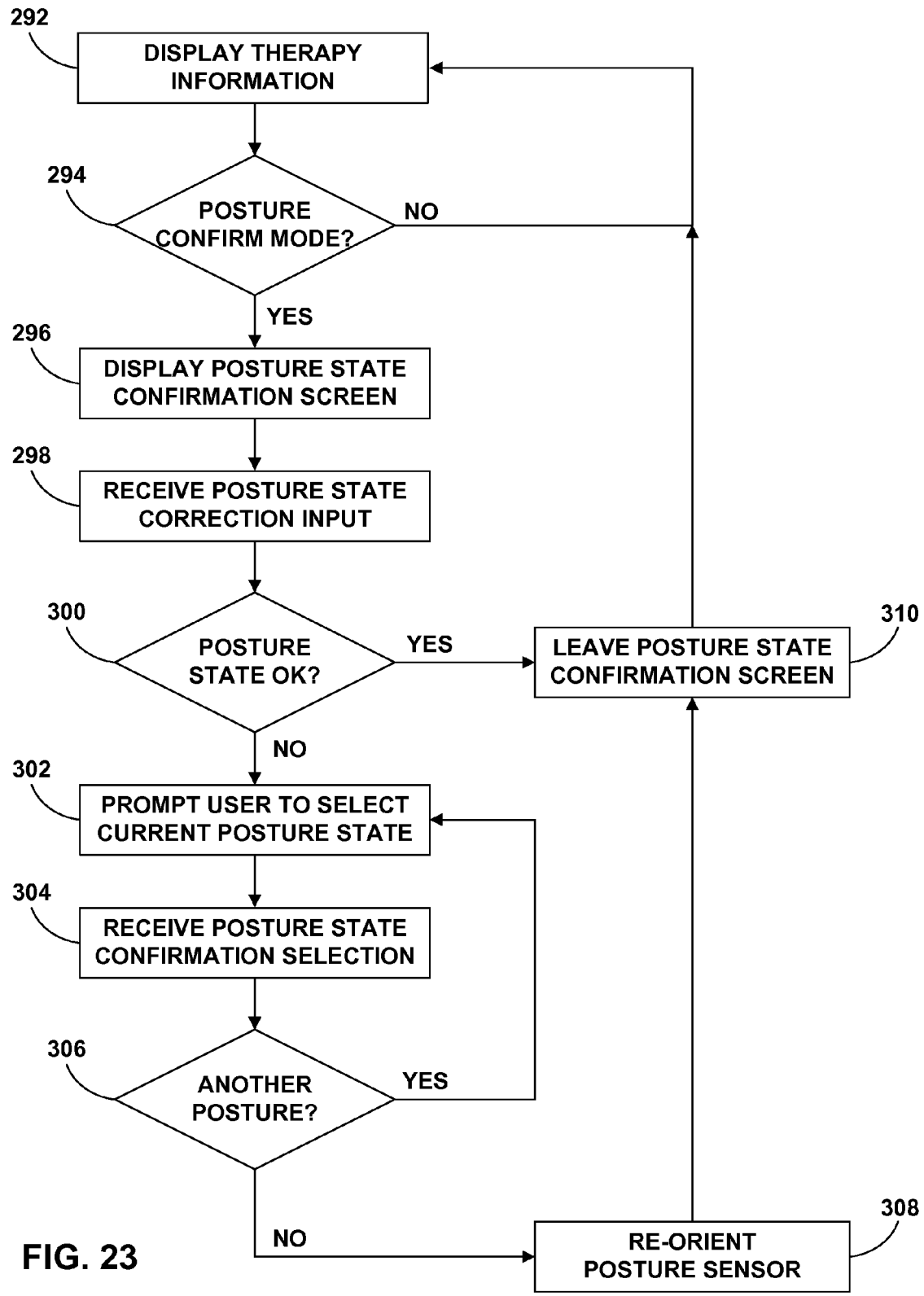
FIG. 23 is a flow chart illustrating an example method for the user to confirm that the correct patient posture state is represented by the posture state indication.

FIG. 23 is a flow chart illustrating an example method for the user to confirm the correct patient posture state is represented by the posture state indication. The example of FIG. 23 is described with respect to patient programmer 30, but any external programmer, such as clinician programmer 60 may alternatively be used. As shown in FIG. 23, patient programmer 30 displays therapy information to patient 12 (292). If patient 12 enters the posture confirm mode (294), as illustrated in FIG. 12, processor 104 displays the posture state confirmation screen (296). User interface 106 then receives the posture state correction input from patient 12 (298).

If the posture state is correct because the posture state indication is correctly representative of the patient 12 posture state (300), then processor 104 leaves the posture state confirmation screen (310) and user interface 106 continues to display therapy information (292). If the posture state is not correct (300), processor 104 prompts patient 12 to select the posture state indication that is representative of the current correct posture state via user interface 106 (302), as illustrated in the example of FIG. 13. User interface 106 then receives the posture sate confirmation selection (304). If processor 104 requires another posture state confirmation (306), user interface 106 again prompts patient 12 to select the current posture state with a posture state indication (302). Otherwise, processor 104 re-orients the activity sensor and/or the posture state parameter value to the new posture state confirmation selection made by patient 12 (308). Processor 104 then leaves the posture state confirmation screen (310) and continues to display therapy information (292).

The disclosure may be capable of providing many features to a user. For example, the patient may continually monitor automated therapy based on sensed posture states by viewing the sensed posture state as represented by the posture state indication. If there is any problem with the automated adjustment to therapy, the patient can first determine if the system is correctly sensing the posture state. In addition, the patient may confirm or change the sensed posture state by selecting the correct posture state indication. In turn, the system may re-orient the activity sensor to more accurately detect the posture state of the patient.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

In addition, it should be noted that the systems described herein may not be limited to treatment of a human patient. In alternative embodiments, these systems may be implemented in non-human patients, e.g., primates, canines, equines, pigs, and felines. These animals may undergo clinical or research therapies that may benefit from the subject matter of this disclosure.

Many embodiments of the disclosure have been described. Various modifications may be made without departing from the scope of the claims. These and other embodiments are within the scope of the following claims.

The invention claimed is:

1. A method comprising:
   receiving, by a processor, a detected posture state indicating a posture state currently occupied by a medical patient;
   presenting, by a user interface of a medical device programmer, a posture state indication representative of the detected posture state currently occupied by the medical patient;
   presenting an automatic posture response icon with at least one of a therapy program or a group of therapy programs, wherein the automatic posture response icon indicates therapy is delivered automatically according to the posture state of the medical patient; and
   controlling delivery of therapy to the medical patient.

2. The method of claim 1, wherein presenting the posture state indication comprises generating a visible, audible or tactile representation of the posture state indication.

3. The method of claim 1, wherein presenting the posture state indication comprises presenting a visible representation of the posture state indication.

4. The method of claim 3, wherein presenting the posture state indication comprises presenting the posture state indication on a display associated with the user interface of the medical device programmer.

5. The method of claim 1, further comprising presenting, via the user interface of the medical device programmer, therapy information relating to therapy delivered to the medical patient by a medical device.

6. The method of claim 5, wherein receiving the detected posture state comprises receiving the detected posture state from the medical device.

7. The method of claim 1, wherein the posture state indication includes at least one of a plurality of posture state indications that represents a respective posture of the medical patient or a respective activity of the patient.

8. The method of claim 1, wherein the posture state indication includes at least one of an upright indication, a lying back indication, a lying front indication, a lying right indication, a lying left indication, a walking indication, a running indication, a biking indication, a swimming indication, a car riding indication, a lifting indication, or a typing indication.

9. The method of claim 1, wherein the posture state indication includes at least one of a graphical representation, a word, a letter, a number, or an arrow.

10. The method of claim 1, further comprising presenting a supplementary posture state indication with the posture state indication, wherein the supplementary posture state indication represents the posture state differently than the posture state indication.

11. The method of claim 10, wherein the posture state indication is a graphical representation and the supplementary posture state indication is a word.

12. The method of claim 1, further comprising receiving, via the user interface, a posture state confirmation selection from the medical patient that confirms the patient is currently engaged in the posture state represented by the presented posture state indication.

13. The method of claim 1, further comprising controlling, according to the posture state of the medical patient, an implantable medical device to deliver electrical stimulation therapy to the medical patient.

14. A programmer for an implantable medical device, the programmer comprising:
a processor configured to receive a detected posture state indicating a posture state currently occupied by a medical patient; and
a user interface configured to:
present a posture state indication representative of the detected posture state currently occupied by the medical patient, and
present an automatic posture response icon with at least one of a therapy program or a group of therapy programs, wherein the automatic posture response icon indicates therapy is delivered automatically according to the detected posture state of the medical patient, and wherein the programmer is configured to control delivery of therapy from the implantable medical device to the medical patient.

15. The programmer of claim 14, further comprising a telemetry circuit that receives the detected posture state from the implantable medical device.

16. The programmer of claim 14, wherein the user interface is configured to present therapy information relating to therapy delivered to the medical patient by the implantable medical device.

17. The programmer of claim 14, further comprising a memory configured to store a plurality of posture state indications, wherein:
the posture state indication is one of the plurality of posture state indications; and the plurality of posture state indication include at least one of an upright indication, a lying back indication, a lying front indication, a lying right indication, a lying left indication, a walking indication, a running indication, a biking indication, a swimming indication, a car riding indication, a lifting indication, or a typing indication.

18. The patient programmer of claim 14, wherein the posture state indications include at least one of a graphical representation, a symbolic icon, a word, a letter, a number, or an arrow.

19. The method of claim 1, further comprising detecting, by an implantable medical device, the posture state currently occupied by the medical patient.

20. The method of claim 1, further comprising selecting the posture state indication from a plurality of posture state indications, wherein each of the posture state indications is associated with a different posture state.

21. The programmer of claim 14, wherein the programmer is configured to select the posture state indication associated with the received posture state.

22. The programmer of claim 14, wherein the user interface is configured to present a supplementary posture state indication with the posture state indication, wherein the supplementary posture state indication represents the posture state differently than the posture state indication.

23. The programmer of claim 22, wherein the posture state indication includes a graphical representation and the supplementary posture state indication includes a word.

24. The programmer of claim 14, wherein the user interface is configured to receive a posture state confirmation from the medical patient that confirms that the medical patient is currently engaged in the posture state represented by the presented posture state indication.

25. The method of claim 5, wherein the therapy information is an indication of electrical stimulation therapy selected for delivery to the medical patient by the medical device.

26. The programmer of claim 16, wherein the therapy information is an indication of electrical stimulation therapy selected for delivery to the medical patient by the implantable medical device.

27. A non-transitory computer-readable storage medium comprising instructions that cause a processor to:
receive a detected posture state indicating a posture state currently occupied by a medical patient;
present, via a user interface of a medical device programmer, a posture state indication representative of the detected posture state currently occupied by the medical patient;
present an automatic posture response icon with at least one of a therapy program or a group of therapy programs, wherein the automatic posture response icon indicates therapy is delivered automatically according to the posture state of the medical patient; and
control delivery of therapy to the medical patient.

28. The non-transitory computer-readable storage medium of claim 27, wherein the instructions that cause the processor to present the posture state indication comprises instructions that cause the processor to present a visible representation of the posture state indication.

29. The non-transitory computer-readable storage medium of claim 27, wherein the posture state indication includes at least one of an upright indication, a lying back indication, a lying front indication, a lying right indication, a lying left indication, a walking indication, a running indication, a biking indication, a swimming indication, a car riding indication, a lifting indication, or a typing indication.

30. The non-transitory computer-readable storage medium of claim 27, wherein the posture state indication includes at least one of a graphical representation, a symbolic icon, a word, a letter, a number, or an arrow.

31. The non-transitory computer-readable storage medium of claim 27, further comprising instructions that cause the processor to receive, via the user interface, a posture state confirmation selection from the medical patient, wherein the posture state confirmation confirms the patient is currently engaged in the posture state represented by the presented posture state indication.

32. The non-transitory computer-readable storage medium of claim 27, further comprising instructions that cause the processor to select the posture state indication from a plurality of posture state indications, wherein each of the posture state indications is associated with a different posture state.

33. The method of claim 1, wherein presenting the posture state indication comprises, responsive to receiving the detected posture state, presenting, by the user interface of the medical device programmer, the posture state indication representative of the detected posture state currently occupied by the medical patient.

34. The method of claim 1, wherein the posture state indication includes a symbolic icon that represents the detected posture state currently occupied by the medical patient.

35. The method of claim 1, wherein the medical device programmer is a patient programmer configured for use by the medical patient.

36. The method of claim 1, wherein the processor includes a processor of the medical device programmer, and wherein:
receiving the detected posture state comprises receiving, by the processor of the medical device programmer and via wireless telemetry between the medical device programmer and an implantable medical device, the detected posture state from the implantable medical device implanted within the medical patient,
the method further comprising, responsive to receiving the detected posture state, selecting, by the medical device programmer, the posture state indication from a plurality of posture state indications stored within a memory of the medical device programmer, wherein each of the posture state indications is associated with a different posture state, and wherein
presenting the posture state indication comprises, responsive to selecting the posture state indication, presenting the posture state indication representative of the detected posture state currently occupied by the medical patient.

37. The method of claim 1, further comprising:
receiving, by the medical device programmer, input indicating that the detected posture state incorrectly identifies a current posture state occupied by the medical patient;
presenting, by the user interface, a plurality of posture state indications associated with different posture states; and
receiving, by the medical device programmer, user selection of one of the plurality of posture state indications representative of the current posture state occupied by the medical patient.

38. The method of claim 37, further comprising re-orienting, based on the user selection of the one of the plurality of posture state indications, a posture state parameter value from which the detected posture state is determined.

39. A method comprising:
receiving, by a processor, a detected posture state indicating a posture state currently occupied by a medical patient;
presenting, by a user interface of a medical device programmer, a posture state indication representative of the detected posture state currently occupied by the medical patient;
receiving, via the user interface, a posture state confirmation selection from the medical patient that confirms the patient is currently engaged in the posture state represented by the presented posture state indication; and
controlling delivery of therapy to the medical patient.

40. A programmer for an implantable medical device, the programmer comprising:
a processor configured to receive a detected posture state indicating a posture state currently occupied by a medical patient; and
a user interface configured to:
present a posture state indication representative of the detected posture state currently occupied by the medical patient, and
receive a posture state confirmation selection from the medical patient that confirms the patient is currently engaged in the posture state represented by the presented posture state indication, wherein the programmer is configured to control delivery of therapy from the implantable medical device to the medical patient.

* * * * *